United States Patent [19]
Scott et al.

[11] Patent Number: 5,770,694
[45] Date of Patent: Jun. 23, 1998

[54] GENETICALLY ENGINEERED BPI VARIANT PROTEINS

[75] Inventors: Randal W. Scott, Cupertino; Marian N. Marra, San Mateo, both of Calif.

[73] Assignee: Incyte Pharmaceuticals, Inc., Palo Alto, Calif.

[21] Appl. No.: 915,720

[22] PCT Filed: Aug. 13, 1991

[86] PCT No.: PCT/US91/05758

§ 371 Date: Jul. 22, 1992

§ 102(e) Date: Jul. 22, 1992

Related U.S. Application Data

[63] Continuation-in-part of Ser. No. 567,016, Aug. 13, 1990, abandoned, and Ser. No. 681,551, Apr. 5, 1991, Pat. No. 5,171,739.

[51] Int. Cl.$^6$ ........................ C07K 14/00; C07K 14/435; A61K 38/03; A61K 38/17
[52] U.S. Cl. ............................ 530/350; 514/12; 514/21; 435/69.1
[58] Field of Search ....................... 424/88, 92; 435/69.1, 435/69.3; 514/12, 2, 21; 530/350

[56] References Cited

U.S. PATENT DOCUMENTS

| | | |
|---|---|---|
| 84,335 | 1/1868 | Elsbach . |
| 5,171,739 | 12/1992 | Scott et al. .................................. 514/12 |

FOREIGN PATENT DOCUMENTS

| | | |
|---|---|---|
| 0272489 | 6/1988 | European Pat. Off. . |
| PCTUS8802700 | 8/1988 | WIPO . |
| WO 89/01486 | 2/1989 | WIPO . |
| PCTUS9000837 | 2/1990 | WIPO . |

OTHER PUBLICATIONS

M.N. Marra, et al. (1990) J. Immunol., 144:662–666.
P. Elsbach, et al. (1988) Bacteria–Host Cell Interaction, pp. 47–60.
P. Gray, et al. (1988) Clinical Research, 36(3):620A.
P. Gray, et al. (1989) The Journal of Biological Chemistry 264(16):9505.
J. Weiss, et al. (1982) The American Society of Clinical Investigation, Inc. 69:959.
J. Weiss, et al. (1985) The American Society of Clinical Investigation, Inc. 76:206.
S. Leong, et al. J. Cell Biochem. Suppl. 13:66 (1989).
J. Weiss, et al., Infection and Immunity, 38:1149–1153 (1982).
K. Muello, et al. Clinical Research, 31:371A.
J. Weiss, et al. J. Clin. Invest., 71:540–549 (1983).
W.M. Shafer, et al. Infection and Immunity, 45:29–35 (1984).
C.J. Hovde, et al. Infection and Immunity, 54:142–148 (1986).
J. Weiss, et al. Infection and Immunity, 51:594–599 (1986).
J.K. Spitznagel, et al. J. Immunol., 139:1291–1296 (1987).
M.M. Shafer, et al. Infection and Immunity, 55:1536–1539 (1987).

G.I. Veld, et al. Infection and Immunity, 56:1203–1208 (1988).
M.M. Farley, et al. Infection and Immunity, 56:1589–1592 (1988).
B.A. Mannion et al., J. Immunol. 142:2807–2812 (1989).
J. Weiss, et al. (1985) ASCI Metabolism, 33(2):567(A).
B.A. Mannion et al., J. Clin. Invest. 85:853–860 (1990).
A.H. Pereira, et al., Blood 76:825–834 (1990).
R.R. Schumann, et al. Science 249:1429–1431 (1990).
Larrick et al., "Complementary DNA Sequence of Rabbit Cap 18—A Unique Lipopolysaccharide Binding Protein," *Biochem. Biophys. Research Communications* (1991) 179:170–175.
Ooi et al., "Endotoxin–Neutralizing Properties of the 25 kD N–Terminal Fragment and a Newly Isolated 30kD C–Terminal Fragment of the 55–60 kD Bactericidal/Permeability–increasing Protein of Human Neutrophils," *J. Exp. Med.* (1991) 174:649–655.
Gray et al., "Cloning of the cDNA of a Human Neutrophil Bactericidal Protein," *J. Biol. Chem.* (1989) 264:9505–9509.
Weiss, J. et al. (1975), "Partial Characterization and Purification of a Rabbit Granulocyte Factor that Increases Permeability of *Escherichia coli,* " *J. Clin. Invest.* 55:33–42.
Morrison et al. (1976), "Binding of Polymyxin B to the Lipid A Portion of Bacterial Lipopolysaccharides," *Immunochemistry* 13:813–818.
Morrison et al. (1978), "The Effects of Bacterial Endotoxins on Host Mediation Systems," *Am. J. Pathol.* 93(2):527–617.
Weiss et al. (1978), "Purification and Characterization of a Potent Bacteriacidal and Membrane Active Protein from the Granules of Human Polymorphonuclear Leukocytes," *J. Biol. Chem.* 253:2664–2672.
Elsbach et al. (1979), "Separation and Purification of a Potent Bactericidal/Permeability–increasing Protein and a Closely Associated Phospholipase $A_2$ from Rabbit Polymorphonuclear Leukocytes," *J. Biol. Chem.* 254:11000–11009.
Weiss et al. (1982), "Killing of Gram–Negative Bacteria by Polymorphonuclear Leukocytes," *Am. Society Clin. Invest.* 69:959–970.
Weiss et al. (1982), "Sensitivity of K1–Encapsulated *Escherichia coli* to Killing by the Bactericidal/Permeability–Increasing Protein of Rabbit and Human Neutrophils," *Infect. Immun.* 38:1149–1153.
Weiss et al. (1983), "Role of Charge and Hydrophobic Interactions in the Action of the Bactericidal/Permeability–Increasing Protein of Neutrophils on Gram–negative Bacteria," *J. Clin. Invest.* 71:540–549.

(List continued on next page.)

*Primary Examiner*—Hazel F. Sidberry
*Attorney, Agent, or Firm*—Carol L. Francis; Bozicevic & Reed LLP

[57] ABSTRACT

The present invention provides a composition comprising a BPI Protein and an anionic compound which composition exhibits (1) no bactericidal activity and (2) endotoxin neu Ooi et al Journ of Exp Med. 174:649–655, 1991. tralizing activity. Also, this invention provides methods for using BPI Proteins.

2 Claims, 26 Drawing Sheets

OTHER PUBLICATIONS

Muello et al. (1983), "The Role Endotoxin in the Action of the Bactericidal/Permeability Increasing Neutrophil Protein on the Bacterial Envelope," *Clinical Research* 31(2):371A.

Shenep et al. (1984), "Kinetics of Endotoxin Release During Antibiotic Therapy For Experimental Gram–Negative Bacterial Sepsis," *J. Infect. Dis.* 150(3):380–388.

Shafer et al. (1984), "Cationic Antimicrobial Proteins Isolated from Human Neutrophil Granulocytes in the Presence of Diisopropyl Fluorophosphate," *Infection and Immunity* 45:29–35.

Weiss et al. (1984), "The Role of Lipopolysaccharides in the Action of the Bactericidal/Permeability–Increasing Neutrophil Protein on the Bacterial Envelope," *J. Immunol.* 132(6):3109–15.

Duma, R.J., (1985), "Gram–Negative Bacillary Infections," *Am. J. of Med.* 78(Suppl. 6A):154–164.

Weiss et al. (1985), "Oxygen–Independent Intracellular and Oxygen–Dependent Extracellular Killing of *Escherichia coli* S15 by Human Polymorphonuclear Leukocytes," *The American Society of Clinical Investigation, Inc.* 76:206–212.

Weiss et al. (1985), "The Bactericidal/Permeability–Increasing Protein of Neutrophils Retains its Biological Activities After Cleavage by Neutrophil Proteases," *Clinical Research* 33(2):567(A).

Tobias et al. (1986), "Isolation of a Lipopolysaccharide––Binding Acute Phase Reactant from Rabbit Serum," *J. Exp. Med.* 164:777–793.

Hovde et al. (1986), "Characterization of a Protein from Normal Human Polymorphonuclear Leukocytes with Bactericidal Activity Against *Pseudomonas Aeruginosa*," *Infection and Immunity* 54:142–148.

Weiss et al. (1986), "Environmental Modulation of Lipopolysaccharide Chain Length . . . ," *Infection and Immunity* 51:594–599.

Ooi et al. (1987), "A 25–KDa $NH_2$–Terminal Fragment Carries all the Antibacterial Activities of the Human Neutrophil 60–KDa Bactericidal/Permeability–Increasing Protein," *J. Biol. Chem.* 262(31):14891–94.

Bone et al. (1987), "A Controlled Clinical Trial of High-–Dose Methylprednisolone in the Treatment of Severe Sepsis and Septic Shock," *N. Engl. J. of Med.* 317(11):653–658.

Weiss et al. (1987), "Cellular and Subcellular Localization of the Bactericidal/Permeability–Increasing Protein of Neutrophils," BA 83(9):86173.

Spitznagel et al. (1987), "A Monoclonal Antibody that Inhibits the Antimicrobial Action of a 57 KD Cationic Protein of Human Polymorphonuclear Leukocytes," *J. Immunol.* 139:1291–1296.

Farley et al. (1987), "Antimicrobial Binding of a Radiolabeled Cationic Neutrophil Granule Protein," *Infection and Immunity* 55:1536–1539.

Weiss et al. (1987), "Cellular and Subcellular Localization of the Bactericidal/Permeability–Increasing Protein of Neutrophils," *Blood* 69(2):652–659.

Harkonen et al. (1988), "Phase I Study of a Murine Monoclonal Anti–Lipid A Antibody in Bacteremic and Nonbacteremic Patients," *Antimicrobial Agents and Chemotherapy* 32:710–716.

Harkonen et al. (1988), "Clinical Studies of Monoclonal Anti–Lipid A Antibody XMMEN–OE5," *Bacterial Endotoxins: Pathophysiological Effects, Clinical Significance, and Pharmacological Control,* Alan R. Liss, Inc., pp. 395–406.

Appelmelk et al. (1988), "Production, Characterization and Biological Effects of Monoclonal Antibodies to Different Parts of the Gram–Negative Lipopolysaccharide Core Region," *Bacterial Endotoxins: Pathophysiological Effects, Clinical Significance, and Pharmacological Control,* Alan R. Liss, Inc., pp. 373–382.

Larrick et al. (1988), "Generation of a Protective Human Monoclonal for the Treatment of Gram–Negative Sepsis," *Bacterial Endotoxins: Pathophysiological Effects, Clinical Significance, and Pharmacological Control,* Alan R. Liss, Inc., pp. 383–393.

Tobias et al. (1988), "A Family of Lipopolysaccharide Binding Proteins Involved in Responses to Gram–Negative Sepsis," *J. Biol. Chem.* 263(27):13479–13481.

Gray et al., (1988), "Cloning of the Gene of the Human BPI Protein," *Clinical Research* 36(3):620A.

Veld et al. (1988), "Effects of the Bactericidal/Permeability–Increasing Protein of Polymorphonuclear Leukocytes on Isolated Bacterial Cytoplasmic Membrane Vesicles," *Infection and Immunity* 56:1203–1208.

Farley et al. (1988), "Lipopolysaccharide Structure Determines Ionic and Hydrophobic Binding of a Cationic Antimicrobial Neutrophil Granule Protein," *Infection and Immunity* 56:1589–1592.

Elsbach et al. (1988), "Bactericidal/Permeability Increasing Protein (BPI) of Granulocytes: Structure and Function," *Bacteria–Host Cell Interaction,* pp. 47–60.

Luckow et al. (1988), "Trends in the Development of Baculovirus Expression Vectors," *Bio/Technology* 6:47–55.

Tobias et al. (1989), "Identification of a Lipid A Binding Site in the Acute Phase Reactant Lipopolysaccharide Binding Protein," *J. Biol. Chem.* 264:10867–10871.

Wright et al. (1989), "Lipopolysaccharide (LPS) Binding Protein opsonizes LPS–Bearing Particles for Recognition by a Novel Receptor on Macrophages," *J. Exp. Med.* 170:1231–1241.

Gray et al. (1989), "Cloning of the cDNA of a Human Neutrophil Bactericidal Protein," *The Journal of Biological Chemistry* 264(16):9505.

Leong et al., (1989), "Cloning of the cDNA of a Human Neutrophil Bactericidal Protein," *J. Cell Biochem. Suppl.* 13:66.

Mannion et al. (1989), "Preferential Binding of the Neutrophil Cytoplasmic Granule–Derived Bactericidal/Permeability Increasing Protein to Target Bacteria: Implications and Use as a Means of Purification," *J. Immuno.* 142:2807–2812.

Marra et al. (1990), "Bactericidal/Permeability–Increasing Protein has Endotoxin–Neutralizing Activity," *J. Immunol.* 144:662–666.

Mannion et al. (1990), "Separation of Sublethal and Lethal Effects of the Bactericidal/Permeability Increasing Protein on *Escherichia coli,* "*J. Clin. Invest.* 85:853–860.

Pereira et al. (1990), "The Ontogeny of a 57–Kd Cationic Antimicrobial Protein of Human Polymorphonuclear Leukocytes: Localization to a Novel Granule Population," *Blood* 76:825–834.

Schumann et al. (1990), "Structure and Function of Lipopolysaccharide Binding Protein," *Science* 249:1429–1431.

Hovde et al Int & Imm 54:142–148, 1986.

Pereira et al Blood 76:825–834 1990.

Cross et al Infect & Imm 61:2741–2747 1993 The Choice of Bacteria in Immune Models of Sepsas.

Gray et al The Journ of Biol Chem 264:9505–9509 1987, Cloning of the cDNA of a Human Neutrophil Bactercida Protein Geisow TIBTECH 10:333–335, 1992.

Ooi et al The Journ of Biol Chem 262: 14891–14894 1987.

Tobias et al The Journ of Biological Chem 263:13479–13481 1988.

BPI MUTAGENIC PRIMERS

C-TERMINAL TRUNCATION OF BPI

25KD Pro 212 TGA

```
AA.  205                210              212
     Ile  Asn  Tyr  Gly  Leu  Val  Ala  Pro  Ter. Bam HI   (SEQ ID NO: 1)

TAG  AAC  TAT  GGT  CTG  GTG  GCA  CCT  TGA  GGATCCGCG   (SEQ ID NO: 2)

COMP
       3'   ATA  CCA  GAC  CAC  CGT  GGA  ACT  CCTAGGCGC  5'   (SEQ ID NO: 3)

OLIGO 459:
       5' CGCGGATCC    TCA  AGG  TGC  CAC  CAG  ACC  ATA  3'   (SEQ ID NO: 4)
```

FIG. 6

BPI MUTAGENIC PRIMERS

C-TERMINAL TRUNCATION OF BPI

38KD Pro 337 TGA

```
AA.  330                    335             337
     Pro Thr Gly Leu Thr Phe Tyr Pro Ter  Bam HI  (SEQ ID NO: 5)
     CCC ACC GGC CTT ACC TTC TAC CCT TGA  GGATCCGCG  (SEQ ID NO: 6)

COMP:      3' CCG  GAA TGG AAG ATG GGA ACT CCTAGGCGC 5'  (SEQ ID NO: 7)

OLIGO 460:
     5' CGCGGATCC  TCA AGG GTA GAA GGT AAG GCC  3'  (SEQ ID NO: 8)
```

FIG. 7

BPI MUTAGENIC PRIMERS

C-TERMINAL TRUNCATION OF BPI:

PREFFERED ATG 5'HIND III:

AA.  -31                    -26
     HINd III  Start  Met Arg Glu Asn Met Arg  (SEQ ID NO: 9)
     CCCAAGCTT GCC ACC ATG AGA GAG AAC ATG GCC  (SEQ ID NO: 10)

OLIGO 458:
5' CCCAAGCTT GCC ACC ATG AGA GAG AAC ATG GCC 3'  (SEQ ID NO: 11)

FIG. 8

```
  -16        -8           +171      +176
   |          |             |         |
AAAAAAACC  CGAGATCCGCGGATC  CTTTCCT  (SEQ ID NO: 12)
           ‾‾‾‾‾‾‾‾‾‾‾‾‾‾‾
           AvaIXho2Sst2   BamHI
```

HUMAN BACTERIAL PROTEIN cDNA CLONING

```
                                                              -30
  1 CAGGCCTTGAGGTTTGGCAGCTCTGGAGG  met arg glu asn met ala arg gly pro cys asn ala pro arg trp val ser
                                   ATG AGA GAG AAC ATG GCC AGG GGC CCT TGC AAC GCG CCG AGA TGG GTG TCC
                         -10                                                           -20
     leu met val leu val ala ile gly thr ala val thr ala ala val Asn Pro Gly Val Val Val Arg Ile Ser Gln
                                                                                                      10
 82  CTG ATG GTG CTC GTC GCC ATA GGC ACC GCA GTG ACA GCC GCC GTG AAC CCT GGC GTC GTG GTC AGG ATC TCC CAG
                                                                        1
                                                                  30                Arg
     Lys Gly Leu Asp Tyr Ala Ser Gln Gly Thr Ala Ala Leu Gln Lys Glu Leu Lys Ile Lys Ile Pro Asp
157  AAG GGC CTG GAC TAC GCC AGC CAG GGG ACG GCC GCT CTG CAG AAG GAG CTG AAG ATC AAG ATT CCT GAC
                                50                                                           60
     Tyr Ser Asp Ser Phe Lys Ile Lys His Leu Gly Lys Gly His Tyr Ser Phe Tyr Ser Met Asp Ile Arg Glu Phe
232  TAC TCA GAC AGC TTT AAG ATC AAG CAT CTT GGG AAG GGG CAT TAT AGC TTC TAC TCC ATG GAC ATC CGT GAA TTC
                           70                                            80
     Gln Leu Pro Ser Ser Gln Ile Ser Met Val Pro Asn Val Gly Leu Lys Phe Ser Ile Ser Asn Ala Asn Ile Lys
307  CAG CTT CCC AGT TCC CAG ATA TCC ATG GTG CCC AAT GTG GGC CTT AAG TTC TCC ATC AGC AAC GCC AAT ATC AAG
```

```
FROM FIG. 12A 90                        100                          110
     Ile Ser Gly Lys Trp Lys Ala Gln Lys Arg Phe Leu Lys Met Ser Gly Asn Phe Asp Leu Ser Ile Glu Gly Met
382  ATC AGC GGG AAA TGG AAG GCA CAA AAG AGA TTC TTA AAA ATG AGC GGC AAT TTT GAC CTG AGC ATA GAA GGC ATG 120                          130
     Ser Ile Ser Ala Asp Leu Lys Leu Gly Ser Asn Pro Thr Ser Gly Lys Pro Thr Ile Thr Cys Ser Ser Cys Ser
457  TCC ATT TCG GCT GAT CTG AAG CTG GGC AGT AAC CCC ACG TCA GGC AAG CCC ACC ATC ACC TGC AGC TCC TGC AGC 140                          150                          160
     Ser His Ile Asn Ser Val His Val His Ile Ser Lys Ser Lys Val Gly Trp Leu Ile Gln Leu Phe His Lys Lys
532  AGC CAC ATC AAC AGT GTC CAC GTG CAC ATC TCA AAG AGC AAA GTC GGG TGG CTG ATC CAA CTC TTC CAC AAA AAA 170                          180
     Ile Glu Ser Ala Leu Arg Asn Lys Met Asn Ser Gln Val Cys Glu Lys Val Thr Asn Ser Val Ser Ser Lys Leu
607  ATT GAG TCT GCG CTT CGA AAC AAG ATG AAC AGC CAG GTC TGC GAG AAA GTG ACC AAT TCT GTA TCC TCC AAG CTG 190                          200                          210
     Gln Pro Tyr Phe Gln Thr Leu Pro Val Met Thr Lys Ile Asp Ser Val Ala Gly Ile Asn Tyr Gly Leu Val Ala
682  CAA CCT TAT TTC CAG ACT CTG CCA GTA ATG ACC AAA ATA GAT TCT GTG GCT GGA ATC AAC TAT GGT CTG GTG GCA 220                     3   230
     Pro Pro Ala Thr Thr Ala Glu Thr Leu Asp Val Gln Met Lys Gly Glu Phe Tyr Ser Glu Asn His His Asn Pro
757  CCT CCA GCA ACC ACG GCT GAG ACC CTG GAT GTA CAG ATG AAG GGG GAG TTT TAC AGT GAG AAC CAC CAC AAT CCA

TO FIG. 12C
```

```
                                    240                         250                              260
      Pro Pro Phe Ala Pro Pro Val Met Glu Phe Pro Ala Ala His Asp Arg Met Val Tyr Gly Leu Ser Asp Tyr
 832  CCT CCC TTT GCT CCA CCA GTG ATG GAG TTT CCC GCT GCT CAT GAC CGC ATG GTA TAC GGC CTC TCA GAC TAC 270                              280
      Phe Phe Asn Thr Ala Gly Leu Val Tyr Gln Glu Ala Lys Met thr Leu Arg Asp Asp Met Ile Pro
 907  TTC TTC AAC ACA GCC GGG CTT GTA TAC CAA GAG GCT AAG ATG ACC CTT AGA GAT GAC ATG ATT CCA 290                              300                              310
      Lys Glu Ser Lys Phe Arg Leu Thr Phe Phe Gly Thr Phe Leu Pro Glu Val Ala Lys Lys Phe Pro Asn
 982  AAG GAG TCC AAA TTT CGA CTG ACA TTC TTT GGA ACC CTA CCT GAG GTG GCC AAG AAG TTT CCC AAC 320                              330
      Met Lys Ile Gln Ile His Val Ser Ala Ser Thr Pro Pro His Leu Ser Val Gln Pro Thr Gly Leu Thr Phe Tyr
1057  ATG AAG ATA CAG ATC CAT GTC TCA GCC TCC ACC CCG CCA CAC CTG TCT GTG CAG CCC ACC GGC CTT ACC TTC TAC 340                                             350                                 360
      Pro Ala Val Asp Val Gln Ala Phe Ala Val Leu Pro Ser Ser Leu Ala Ser Leu Phe Leu Ile Gly Met His
1132  CCT GCC GTG GAT GTC CAG GCC TTT GCC GTG CTC CCC TCC AAC TCC CTG GCT TCC CTC TTC CTG ATT GGC ATG CAC
```

FIG. 12C

FROM FIG. 12C

```
      Thr Thr Gly Ser Met Glu Val Ser Asn Arg Leu Val Gly Glu Leu Lys Leu Asp Arg Leu Leu
                                370                 380
1207  ACA ACT GGT TCC ATG GAG GTC AGC AAC AGG CTT GTT GGA GAG CTC AAG CTG GAT AGG CTC CTG

Glu Leu Lys His Ser Asn Ile Gly Pro Phe Pro Val Glu Leu Leu Gln Asp Ile Met Asn Tyr Ile Val Pro Ile
           390                                 400                                 410
1282  GAA CTG AAG CAC TCA AAT ATT GGC CCC TTC CCG GTT GAA TTG CTG CAG GAT ATC ATG AAC TAC ATT GTA CCC ATT

Leu Val Leu Pro Arg Val Asn Glu Lys Leu Gln Lys Gly Phe Pro Leu Pro Thr Pro Ala Arg Val Gln Leu Tyr
                         420                                 430
1357  CTT GTG CTG CCC AGG GTT AAC GAG AAA CTA CAG AAA GGC TTC CCT CTC CCG ACG CCG GCC AGA GTC CAG CTC TAC

Asn Val Val Leu Gln Pro His Gln Asn Phe Leu Leu Phe Gly Ala Asp Val Val Tyr Lys (SEQ ID NO: 13)
                              440                                 450                    460
1432  AAC GTA GTG CTT CAG CCT CAC CAG AAC TTC CTG CTG TTC GGT GCA GAC GTT GTC TAT AAA TGA AGGCACCAGGGGTGCC

1511  GGGGGCTGTCAGCCGCACCTGTTCCTGATGGGCTGTGTGGGGCACCGGCTGCCTTCCCCAGGAATCCTCTCCAGATCTTAACCAAGAGCCCCTTGCAAAC

1611  TTCTTCGACTCAGATTCAGAAATGATCTAAACACGAGGAGAAACATTATTCATTGGAAAAGTGCATGGTGTATTTTAGGATTATGAGCTTCTTCAAGG

1711  GCTAAGGCTGCAGAGATATTTCCTCCAGGAATCGTGTTTCAATTGTAACCAAGAAATTTCCATTTGTGCTTCATGAAAAAAACTTCTGGTTTTTTCAT

1811  GTG---poly-A tail (SEQ ID NO: 14)
```

FIG. 12D

```
-31  M R E N M A R G P C N A P R W V S L M V L V A I G T A V T A
 -1  A V N P G V V R I S Q K G L D Y A S Q Q G T A A L Q K E L
 30  K R I K I P D Y S D S F K I K H L G K G H Y S F Y S M D I R
 60  E F Q L P S S Q I S M V P N V G L K F S I S N A N I K I S G
 90  K W K A Q K R F L K M S G N F D L S I E G M S I S A D L K L
120  G S N P T S G K P T I T C S S C S S H I N S V H V H I S K S
150  K V G W L I Q L F H K K I E S A L R N K M N S Q V C E K V T
180  N S V S K L Q P Y F Q T L P V M T K I D S V A G I N Y G L
210  V A P P A T T A E T L D V Q M K G E F Y S E N H H N P P P F
240  A P P V M E F P A A H D R M V Y L G L S D Y F F N T A G L V
270  Y Q E A G V L K M T L R D D M I P K E S K F R L T T K F F G
300  T F L P E V A K K F P N M K I Q I H V S A S T P P H L S V Q
330  P T G L T F Y P   (SEQ ID NO: 15)
```

FIG. 13

```
-31  M R E N M A R G P C N A P R W V S L M V L V A I G T A V T A
 -1  A V N P G V V R I S Q K G L D Y A S Q Q G T A A L Q K E L
 30  K R I K I P D Y S D S F K I K H L G K G H Y S F Y S M D I R
 60  E F Q L P S S Q I S M V P N V G L K F S I S N A N I K I S G
 90  K W K A Q K R F L K M S G N F D L S I E G M S I A D L K L
120  G S N P T S G K P T I T C S S C S S H I N S V H V H I S K S
150  K V G W L I Q L F H K K I E S A L R N K M N S Q V C E K V T
180  N S V S S K L Q P Y F Q T L P V M T K I D S V A G I N Y G L
210  V A P  (SEQ ID NO: 16)
```

FIG. 14

A. LBP/BPI Chimera

```
LBP-->     10         20         30         40         50         60
ANPGLVARIT DKGLQYAAQE GLLALQSELL RITLPDFTGD LRIPHVGRGR YEFHSLNIHS
           70         80         90        100        110        120
CELLHSALRP VPGQGLSLSI SDSSIRVQGR WKVRKSFFKL QGSFDVSVKG ISISVNLLLG
          130        140        150        160        170        180
SESSGRPTGY CLSCSSDIAD VEVDMSGDSG WLLNLFHNQI ESKFQKVLES RICEMIQKSV
          190       BPI-->  210        220        230        240
SSDLQPYLQT LPVTTEIDSV AGINYGLVAP PATTAETLDV QMKGEFYSEN HHNPPPFAPP
          250        260        270        280        290        300
VMEFPAAHDR MVYLGLSDYF FNTAGLVYQE AGVLKMTLRD DMIPKESKFR LTTKFFGTFL
          310        320        330        340        350        360
PEVAKKFPNM KIQIHVSAST PPHLSVQPTG LTFYPAVDVQ AFAVLPNSSL ASLFLIGMHT
          370        380        390        400        410        420
TGSMEVSAES NRLVGELKLD RLLLELKHSN IGPFPVELLQ DIMNYIVPIL VLPRVNEKLQ
          430        440        450
KGFPLPTPAR VQLYNVVLQP HQNFLLFGAD VVYK (SEQ ID NO: 17)
```

FIG. 23

B. CHO⁻ BPI

```
          10         20         30         40         50         60
VNPGVVVRIS QKGLDYASQQ GTAALQKELK RIKIPDYSDS FKIKHLGKGH YSFYSMDIRE
          70         80         90        100        110        120
FQLPSSQISM VPNVGLKFSI SNANIKISGK WKAQKRFLKM SGNFDLSIEG MSISADLKLG
         130        140        150        160        170        180
SNPTSGKPTI TCSSCSSHIN SVHVHISKSK VGWLIQLFHK KIESALRNKM NSQVCEKVTN
         190        200        210        220        230        240
SVSSKLQPYF QTLPVMTKID SVAGINYGLV APPATTAETL DVQMKGEFYS ENHHNPPPFA
         250        260        270        280        290        300
PPVMEFPAAH DRMVYLGLSD YFFNTAGLVY QEAGVLKMTL RDDMIPKESK FRLTTKFFGT
         310        320        330        340        350        360
FLPEVAKKFP NMKIQIHVSA STPPHLSVQP TGLTFYPAVD VQAFAVLPNS ÅLASLFLIGM
         370        380        390        400        410        420
HTTGSMEVSA ESNRLVGELK LDRLLLELKH SNIGPFPVEL LQDIMNYIVP ILVLPRVNEK
         430        440        450
LQKGFPLPTP ARVQLYNVVL QPHQNFLLFG ADVVYK (SEQ ID NO: 18)
```

FIG. 24

C. BPI (DP linkage)

```
          10         20         30         40         50         60
VNPGVVVRIS QKGLDYASQQ GTAALQKELK RIKIPDYSDS FKIKHLGKGH YSFYSMDIRE
          70         80         90        100        110        120
FQLPSSQISM VPNVGLKFSI SNANIKISGK WKAQKRFLKM SGNFDLSIEG MSISADLKLG
         130        140        150        160        170        180
SNPTSGKPTI TCSSCSSHIN SVHVHISKSK VGWLIQLFHK KIESALRNKM NSQVCEKVTN
         190        200        210        220        230        240
SVSSKLQPYF QTLPVMTKID PVAGINYGLV APPATTAETL DVQMKGEFYS ENHHNPPPFA
         250        260        270        280        290        300
PPVMEFPAAH DRMVYLGLSD YFFNTAGLVY QEAGVLKMTL RDDMIPKESK FRLTTKFFGT
         310        320        330        340        350        360
FLPEVAKKFP NMKIQIHVSA STPPHLSVQP TGLTFYPAVD VQAFAVLPNS SLASLFLIGM
         370        380        390        400        410        420
HTTGSMEVSA ESNRLVGELK LDRLLLELKH SNIGPFPVEL LQDIMNYIVP ILVLPRVNEK
         430        440        450
LQKGFPLPTP ARVQLYNVVL QPHQNFLLFG ADVVYK (SEQ ID NO: 19)
```

FIG. 25

BPI cDNA Reengineering

```
                      NheI
oligo #98 --> TATCATGCTAG- (SEQ ID NO: 20)
              -CAG GCC TTG AGG TTT TGG CAG  (SEQ ID NO: 21)                                         48
    1          CAG GCC TTG AGG TTT TGG CAG AGG ATG AGA GAG AAC ATG GCC                              6
    1                                       Met Arg Glu Asn Met Ala 49         AGG GGC CCT TGC AAC GCG CCG AGA TGG GTG TCC ATG CTG GTG TCC ATG CTC GTC               96
    7         Arg Gly Pro Cys Asn Ala Pro Arg Trp Val Ser Met Leu Val Ser Met Leu Val              22

... 25K ...

625         AAC AAG ATG AAC AGC CAG GTC TGC GAG AAA GTG ACC AAT TCT GTA TCC                      672
  199         Asn Lys Met Asn Ser Gln Val Cys Glu Lys Val Thr Asn Ser Val Ser                     214
                                                                              ClaI
                                         CTG CCA GTA ATG ACC ATG AAA ATC  (SEQ ID NO: 27)
                              Oligo #89 --> CTG CCA GTA ATG ACC ATG AAA ATC                       720
  673         TCC AAG CTG CAA CCT TAT TTC CAG ACT CTG CCA GTA ATG ACC ATG AAA ATA                 230
  215         Ser Lys Leu Gln Pro Tyr Phe Gln Thr Leu Pro Val Met Thr Lys Ile GAT GCT GGT GTG GCT GGA ATC <-- Oligo #93 (SEQ ID NO: 22)
              GAT TCT GGT GTG GCT GGA ATC <-- Oligo #90 (SEQ ID NO: 23)
  721         GAT TCT GGT GTG GCT GGA ATC AAC TAT GGT CTG TTG GCA CCT CCA GCA ACC                 768
  231         Asp Ser Gly Val Ala Gly Ile Asn Tyr Gly Leu Val Ala Pro Ala Thr                    246

769         ACG GCT GAG ACC CTG GAT GTA CAG ATG AAG GGG GAG TTT TAC AGT GAG                     816
  247         Thr Ala Glu Thr Leu Asp Val Gln Met Lys Gly Glu Phe Tyr Ser Glu                    262

... 30K ...

GT CTG CAA CAG ATA
 1441         CTT CAG CCT CAC CAG AAC TTC CTG TTC GGT GCA GAC GTT TAT                             1488
  471         Leu Gln Pro His Gln Asn Phe Leu Phe Gly Ala Asp Val Tyr                             486

XhoI
              TGAGCTCATGCAG <-- Oligo #97 (SEQ ID NO: 24)
 1489         TTT ACT TGA AGG CAC CAG GGG TGC CGG GGG CTG TCA GCC GCA CCT GTT CCT                 1536
  487         Phe Thr ***                                                                        488
              Lys *** (SEQ ID NO: 25)

1537         GAT GGG CTG TGG GGC ACC GGC TGC CTT TCC CCA GGG AAT CCT CTC CAG                     1584

(SEQ ID NO: 26)
```

FIG. 26

GENETICALLY ENGINEERED BPI VARIANT PROTEINS

This application is a 35 U.S.C 371 of PCT/US91/05758 filed Aug. 13, 1991 and a continuation-in-part of U.S. Ser. No. 567,016, filed Aug. 13, 1990, now abandoned and U.S. Ser. No. 681,551, filed Apr. 5, 1991, U.S. Pat. No. 5,171,739, the contents of all of which are hereby incorporated by reference.

BACKGROUND OF THE INVENTION

Gram negative infections are a major cause of morbidity and mortality especially in hospitalized and immunocompromised patients. [Duma, R. J., Am. J. of Med., 78 (Suppl. 6A): 154–164 (1985); and Kreger B. E., D. E. Craven and W. R. McCabe, Am. J. Med., 68: 344–355 (1980)]. Although available antibiotics are generally effective in containing the infection, they do nothing to neutralize the pathophysiological effects associated with lipopolysaccharide (LPS).

LPS is a major component of the outer membrane of gram negative bacteria and is released when the organisms are lysed. [Shenep, J. L. and K. A. Morgan, J. Infect. Dis., 150 (3): 380–388 (1984)]

LPS released during antibiotic therapy is a potent stimulator of the inflammatory response. Many detrimental effects of LPS in vivo result from soluble mediators released by inflammatory cells. [Morrison D. C. and R. J. Ulevich, Am. J. Pathol., 93 (2): 527–617 (1978)] LPS induces the release of mediators by host inflammatory cells which may ultimately result in disseminated intravascular coagulation (DIC), adult respiratory distress syndrome (ARDS), cardiac dysfunction, organ failure, liver failure (hepatobiliary dysfunction), brain failure (CNS dysfunction), renal failure, multi-organ failure and shock.

Soluble LPS causes decreased neutrophil chemotaxis, increased adhesiveness, elevated hexose monophosphate shunt activity and $O_2$ radical production, upregulation of surface receptors for complement, and release of granule proteins into the surrounding medium. [Morrison and Ulevich (1978)]

Endotoxemia is a condition associated with the presence of endotoxins, i.e. heat stable bacterial toxins, in the blood. Endotoxins elicit an inflammatory response that is beneficial in fighting the infection but can be damaging to the host if uncontrolled. Endotoxemia induces production of endotoxin binding proteins from the liver and causes release of microbicidal proteins from leukocytes. Our studies show that one of these leukocytes proteins, i.e. BPI, previously known only for its bactericidal activity in vitro. inhibits the ability of endotoxin to stimulate neutrophils and monocytes Ln vitro and reduces death due to endotoxin or bacterial challenge when given in vivo. Further, BPI has been shown to possess antibiotic functions but not cytotoxin functions against the host cell.

Monocytes and neutrophilic granulocytes play a key role in host defense against bacterial infections and also participate in the pathology of endotoxemia. These cells ingest and kill microorganisms intracellularly and also respond to endotoxin in vivo and in vitro by releasing soluble proteins with microbicidal, proteolytic, opsonic, pyrogenic, complement activating and tissue damaging effects.

Tumor necrosis factor (TNF), a cytokine released by endotoxin stimulated monocytes mimics some of the toxic effects of endotoxin in vivo. Injecting animals with TNF causes fever, shock and alterations in glucose metabolism. TNF is also a potent stimulator of neutrophils. Other cytokines such as IL-1, IL-6, and IL-8 also mediate some of the pathophysiologic effects of LPS.

Despite improvements in antibiotic therapy, morbidity and mortality associated with endotoxemia remains high. Antibiotics alone are not effective in neutralizing the toxic effects of LPS. Therefore, the need arises for a therapy with direct endotoxin neutralizing activity. Current methods for treatment of endotoxemia use antibiotics and supportive care. Most available adjunct therapies treat symptoms of endotoxic shock such as low blood pressure and fever but do not inactivate endotoxin. Other therapies inhibit inflammatory host responses to LPS. As indicated below, present therapies have major limitations due to toxicity, immunogenicity, or irreproducible efficacy between animal models and human trials.

Polymyxin B (PMB) is a basic polypeptide antibiotic which has been shown to bind to, and structurally disrupt, the most toxic and biologically active component of endotoxin, Lipid A. PMB has been shown to inhibit endotoxin activation of neutrophil granule release in vitro and is a potential treatment for gram negative infections in humans. However, because of its systemic toxicity, this drug has limited use except as a topical agent.

Combination therapy using antibiotics and high doses of methylprednisolone sodium succinate (MPSS) has been shown to prevent death in an experimental model of gram negative sepsis using dogs. Another study using MPSS with antibiotics in a multicenter, double blind, placebo-controlled, clinical study in 223 patients with clinical signs of systemic sepsis concluded that mortality was not significantly different between the treatment and placebo groups. Further, the investigators found that resolution of secondary infection within 14 days was significantly higher in the placebo group.

A relatively new approach to treatment of endotoxemia is passive immunization with endotoxin neutralizing antibodies. Hyperimmune human immunoglobulin against E. Coli J5 has been shown to reduce mortality in patients with gram negative bacteremia and shock by 50%. Other groups have shown promising results in animal models using mouse, chimeric, and human monoclonal antibodies. Although monoclonal antibodies have advantages over hyperimmune sera, e.g. more consistent drug potency and decreased transmission of human pathogens, there are still many problems associated with administering immunoglobulin to neutralize LPS. Host responses to the immunoglobulins themselves can result in hypersensitivity. Tissue damage following complement activation and deposition of immune complexes is another concern in the use of therapies involving anti-endotoxin antibodies in septic patients.

BPI is a neutrophil granule protein first discovered in 1975 [Weiss, J., R. C. Franson, S. Becherdite, K. Schmeidler, and P. Elsbach J. Clin. Invest., 55:33 (1975)]. BPI was obtained in highly purified form from human neutrophils in 1978 and was shown to increase membrane permeability and have bactericidal activity against Gram negative bacteria when assayed in phosphate buffered saline in vitro [Weiss, J., et al. J. Biol. Chem,253(8): 2664–2672 (1978)]. Weiss et al. [J. Biol. Chem. 254(21): 110010–11014 (1979)], further showed that BPI increased phospholipase A2 activity suggesting a proinflammatory activity for BPI in addition to its in vitro bactericidal activity.

Rabbit BPI was purified in 1979 [Elsbach et al. J. Biol. Chem 254(21): 11000–11009] and shown to have identical bactericidal and permeability increasing properties as BPI from humans providing a further source of material for study. Both BPI from rabbit and human were shown to be effective against a variety of Gram negative bacteria in vitro, including K1-encapsulated *E. coli* [Weiss et al. Infection and Immunity 38(3): 1149–1153, (1982)].

A role for lipopolysaccharide in the in vitro bactericidal action of BPI was proposed in 1984 by Weiss et al. [J. Immunol. 132(6): 3109–3115, (1984)]. These investigators demonstrated that BPI bound to the outer membrane of gram-negative bacteria, caused extracellular release of LPS, and selectively stimulated LPS biosynthesis. In 1984 a protein with similar properties was isolated from human neutrophils and designated cationic antimicrobial protein 57 (CAP 57) [Shafer, W. M., C. E. Martin and J. K. Spitznagel, Infect. Immun., 45:29 (1984)] This protein is identical to BPI as determined by the N-terminal amino acid sequence, amino acid composition, molecular weight and source [Spitznagel et al., Blood 76:825–834, 1990]. Another group, Hovde and Gray, reported a bactericidal glycoprotein with virtually identical properties to BPI in 1986 [Hovde and Gray, Infection and Immunity 54(1): 142–148 (1986)].

In 1985 Ooi et al. reported that BPI retains its in vitro bactericidal activity after cleavage with neutrophil proteases suggesting that fragments of the molecule retain activity [Ooi and Elsbach, Clinical Research 33(2) :567A (1985)]. All of the in vitro bactericidal and permeability increasing activities of BPI were present in the N-terminal 25 kD fragment of the protein [Ooi, C.E., et al. J. Biol. Chem. 262: 14891 (1987)]

Evidence that BPI binds to a structure associated with endotoxin on the outer membrane of bacteria is as follows: (1) increased sensitivity of rough strains of *E. coli* relative to smooth strains to the permeability increasing activities of BPI [Weiss, J. et al. Infect. Immun. 51:594 (1986)]; (2) the Prm A mutation which results in altered endotoxin structure caused decreased binding of both polymyzin b. and BPI [Farley, M. M. et al. Infect. Immun. 56:1536–1539 (1987) and Farley et al. Infect. Immun. 58:1589–1592 (1988)]; (3) polymyxin B (PMB) completed with BPI for binding to *S. typhimurium* [Farley 1988]; and (4) BPI shared amino acid sequence homology and immunocrossreactivity to another endotoxin binding protein termed Lipopolysaccharide Binding Protein (LBP) [Tobias et al., J. Biol. Chem. 263(27): 13479–13481 (1988)].

LBP-LPS complexes bind to a cell surface receptor on monocytes (CD 14) which results in increased synthesis and release of the inflammatory cytokine tumor necrosis factor (TNF) [Schumann et al. Science 249:1429–1431]. Thus, LBP promotes the immunostimulatory activities of LPS. BPI has exactly the opposite effect of LBP. BPI binds LPS and inhibits neutrophil and monocyte activation [Marra et al., J. Immunol. 144:662–666 (1990); Marra and Scott, WO90/09183, published 23 August 1990; C. J. Fisher et al. Circulatory Shock 34: 120 (1991)].

A cDNA encoding BPI was obtained and sequenced by Gray et al. [Gray et al. Clin. Res. 36:620A (1988) and Gray et al. J. Biol. Chem. 264(16): 9505–9506 (1989)]. They reported that BPI is a membrane protein which can be cleaved and released in soluble form as a 25 kDa fragment.

BPI binding to gram negative bacteria was reported originally to disrupt LPS structure, alter microbial permeability to small hydrophobic molecules and cause cell death (Weiss, et al., 1978). More recently these same authors have demonstrated that such effects occur only in the absence of serum albumin. BPI has no bactericidal activity when added to bacteria cultured in the presence of serum albumin, thus suggesting that BPI does not kill bacteria in vivo where albumin is ubiquitous [Mannion et al. J. Clin. Invest. 85: 853–860 (1990) and Mannion et al J. clin. Invest. 86: 631–641)]. Thus it has been previously understood in the art that the beneficial effects of BPI are limited to in vitro bactericidal effects.

Here we show that BPI binds endotoxin in the presence of serum and plasma and, unlike other known endotoxin binding proteins such as LBP, BPI inhibits the immunostimulatory and toxic activities of endotoxin both in vitro and in vivo respectively. Thus BPI has a novel and distinct use in the therapeutic and prophylactic treatment of endotoxin-related disorders including endotoxemia and endotoxic shock.

Further, BPI is described by Gray et al. [J. Biol. Chem. 264 (16): 9505–9509 (1989)] as a membrane protein which must be cleaved to the 25 kDa fragment to be released from the neutrophil granule membrane in soluble form. The present invention provides for a method of producing full length soluble BPI in active form. Further the present invention separates for the first time two molecular forms of the molecule apparently unresolved by Gray et al. representing glycosylated and nonglycosylated forms of the molecule which appear to have different serum half-life profiles in vivo and thus different therapeutic potential. BPI from neutrophils is a mixture of the glycoslyated and nonglycosylated forms.

SUMMARY OF THE INVENTION

The present invention provides a composition comprising a BPI Protein and an anionic compound which composition exhibits (1) no bactericidal activity and (2) endotoxin neutralizing activity.

This invention also provides a biologically active variant of BPI which (1) specifically binds to endotoxin, (2) competes with BPI Protein for binding to endotoxin, and (3) inhibits endotoxin-induced lethality.

The present invention further provides a method for producing and secreting a recombinant BPI Protein from a cell. This method comprises (a) constructing a vector comprising DNA encoding BPI Protein; (b) transfecting the cell with the vector; and (c) culturing the cell so transfected in culture medium under conditions such that recombinant BPI Protein is secreted.

Also, the present invention provides a method for producing a recombinant BPI Protein from a bacterial cell. This method comprises (a) constructing a vector without a signal sequence and comprising DNA encoding BPI Protein; (b) transfecting the bacterial cell with the vector; and (c) culturing the bacterial cell so transfected in culture medium under conditions such that recombinant BPI Protein is produced.

The subject invention further provides a method for producing a recombinant BPI Protein from an insect cell. This method comprises (a) constructing a vector comprising DNA encoding BPI Protein; (b) transfecting the insect cell with the vector; and (c) culturing the insect cell so transfected in culture medium under conditions such that BPI Protein is produced.

Also, this invention provides a method for determining the amount of endotoxin in a sample from a subject which comprises contacting the sample with a BPI Protein under conditions such that an endotoxin-BPI Protein complex is formed, detecting the amount of the complex so formed thereby determining the amount of endotoxin in the sample.

Additionally, the present invention provides a method for determining the amount of endotoxin in a sample containing bound and unbound endotoxin from a subject. This method comprises (a) treating the sample so as to denature any endotoxin binding protein to which the endotoxin may be bound thereby obtaining unbound endotoxin; (b) contacting the treated sample with a BPI Protein under conditions such that the BPI Protein binds to unbound endotoxin of step (a) so that a endotoxin-BPI Protein complex is formed; (c) detecting the amount of the complex so formed thereby determining the amount of endotoxin in the sample.

This present invention also provides a method of detecting endotoxin in a sample which comprises contacting the sample with a BPI Protein such that the endotoxin binds to the BPI Protein and forms a complex therewith; and detecting such complex.

The present invention further provides a method for coating a surgical tool with a BPI Protein so that the BPI Protein will complex with endotoxin which method comprises attaching BPI Protein onto a surface of the tool which surface is designed for contact with a biological sample.

Also, this invention provides a method for coating an implantable, invasive device with a BPI Protein so that it will form a complex with endotoxin which method comprises attaching BPI Protein onto a surface of the device which surface is designed for contact with a biological sample.

The present invention further provides a method for decontaminating a fluid containing endotoxin prior to administration of the fluid into a subject which comprises contacting the fluid with BPI Protein prior to administration, under conditions such that endotoxin forms a complex with BPI Protein, thereby decontaminating the fluid. The fluid may be blood, plasma, blood serum, an isotonic solution, a pharmaceutical agent, a cell culture reagent, or bone marrow.

This invention also provides a kit for detecting the presence of BPI Protein in a biological fluid sample which comprises (a) an assay buffer containing polymyxin B which binds unbound endotoxin molecules; (b) a first antibody attached to a surface, which antibody (1) binds to a portion of active BPI Protein and (2) does not compete with BPI Protein for an endotoxin binding domain; and (c) a second antibody labeled with a detectable moiety which antibody (1) does not compete with the first antibody for BPI Protein binding and (2) specifically binds to BPI Protein at or near the endotoxin binding site, so that when the biological fluid sample is contacted with the first and second antibody in assay buffer, an active BPI Protein contained in the biological fluid sample is bound by the first and second antibody thus forming a first antibody-BPI Protein-second antibody complex, detecting such complex, and thereby detecting BPI Protein in the biological fluid sample.

Also, this invention provides a kit for determining the amount of BPI Protein in a biological fluid sample which comprises (a) an assay buffer containing polymyxin B which binds unbound endotoxin molecules; (b) a first antibody attached to a surface, which antibody (1) binds to a portion of active BPI Protein and (2) does not compete with BPI Protein for an endotoxin binding domain; and (c) a second antibody labeled with a detectable moiety which antibody (1) does not compete with the first antibody for BPI Protein binding and (2) specifically binds to BPI Protein at or near the endotoxin binding site, so that when the biological fluid sample is contacted with the first and second antibody in assay buffer, an active BPI Protein contained in the biological fluid sample is bound by the first and second antibody thus forming a first antibody-active BPI Protein-second antibody complex, detecting such complex, and determining the amount of active BPI Protein in the biological fluid sample.

Additionally, this invention provides a method for preventing endotoxemia in a subject which comprises administering to the subject an amount of a BPI Protein effective to bind to endotoxin so as to prevent endotoxemia in the subject.

The present invention provides a method for treating a subject suffering from endotoxemia which comprises administering to the subject an amount of a BPI Protein effective to bind endotoxin so as to treat the subject suffering from endotoxemia.

A. pT7BPI-F (+) contains the full-length BPI Protein sequence (including the signal sequence) placed in the correct orientation behind the T7 promoter for expression.

B. pT7BPI-F (−) contains the full-length BPI Protein sequence (including the signal sequence) placed in the incorrect orientation behind the T7 promoter (resulting protein is a fusion protein with the 260 amino acid leader peptide of T7 gene 10).

C. pT7BPI-S contains the full-length BPI Protein sequence (without the signal sequence) placed in the correct orientation behind the T7 promoter for expression.

D. pT7212-F contains the proline-212 truncated BPI Protein sequence (including the signal sequence) placed in the correct orientation behind the T7 promoter for expression.

E. pT7212-S contains the proline-212 truncated BPI Protein sequence (without the signal sequence) placed in the correct orientation behind the T7 promoter for expression.

Figure 1A:
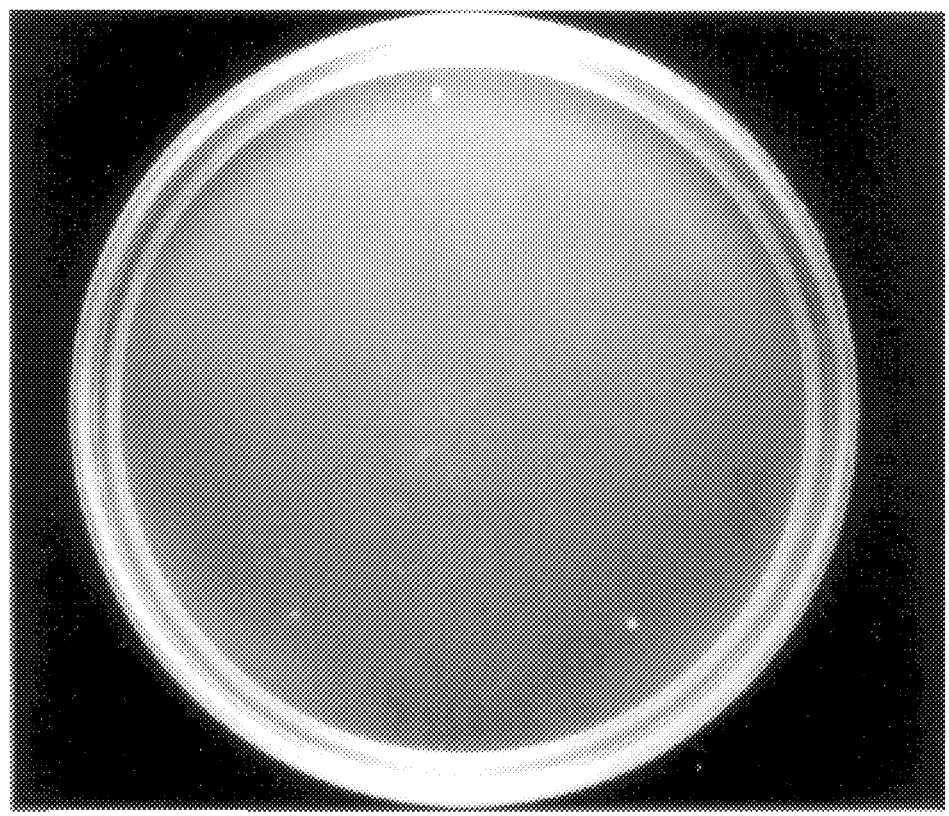
FIG. 1: Photographs of transformed plates of JM109 (DE3) with the T7 promoter/BPI Protein plasmid constructs. Photographs were taken with f8 at $1/125$ second exposure.
Figure 1B:
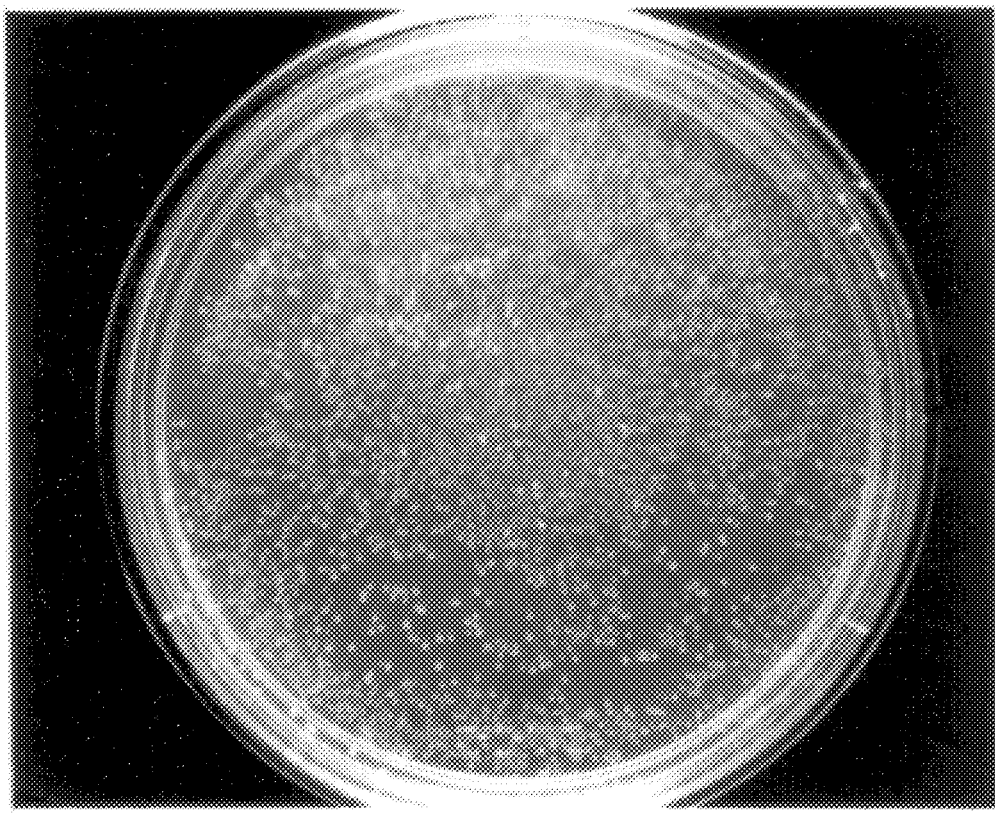
Figure 1C:
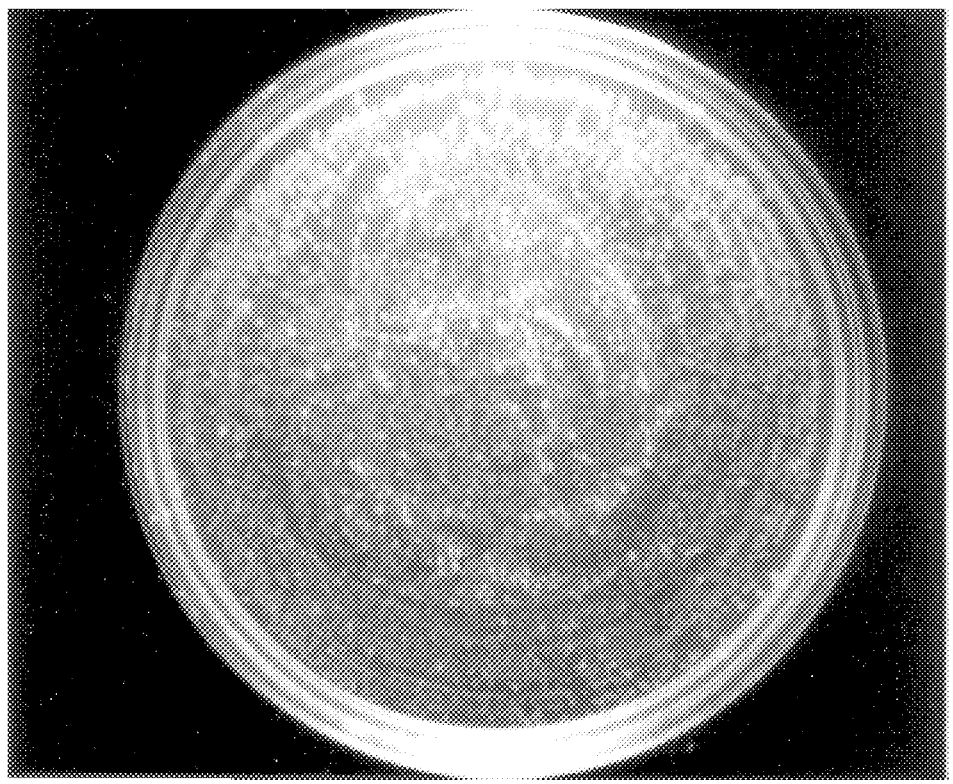
Figure 1D:
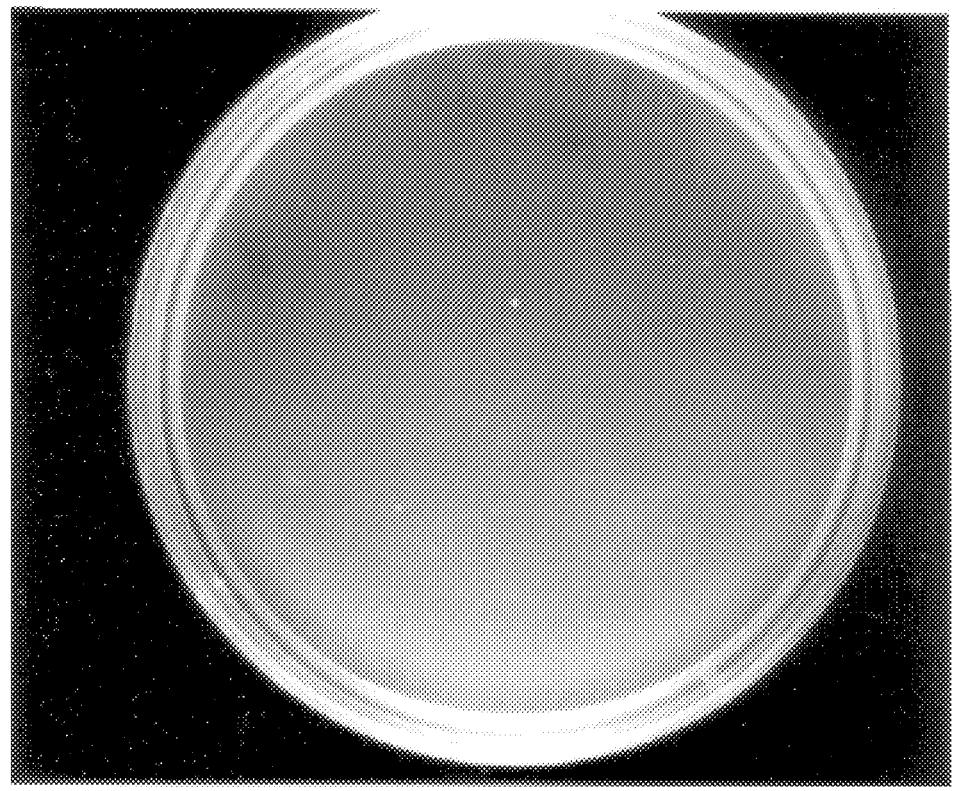
Figure 1E:
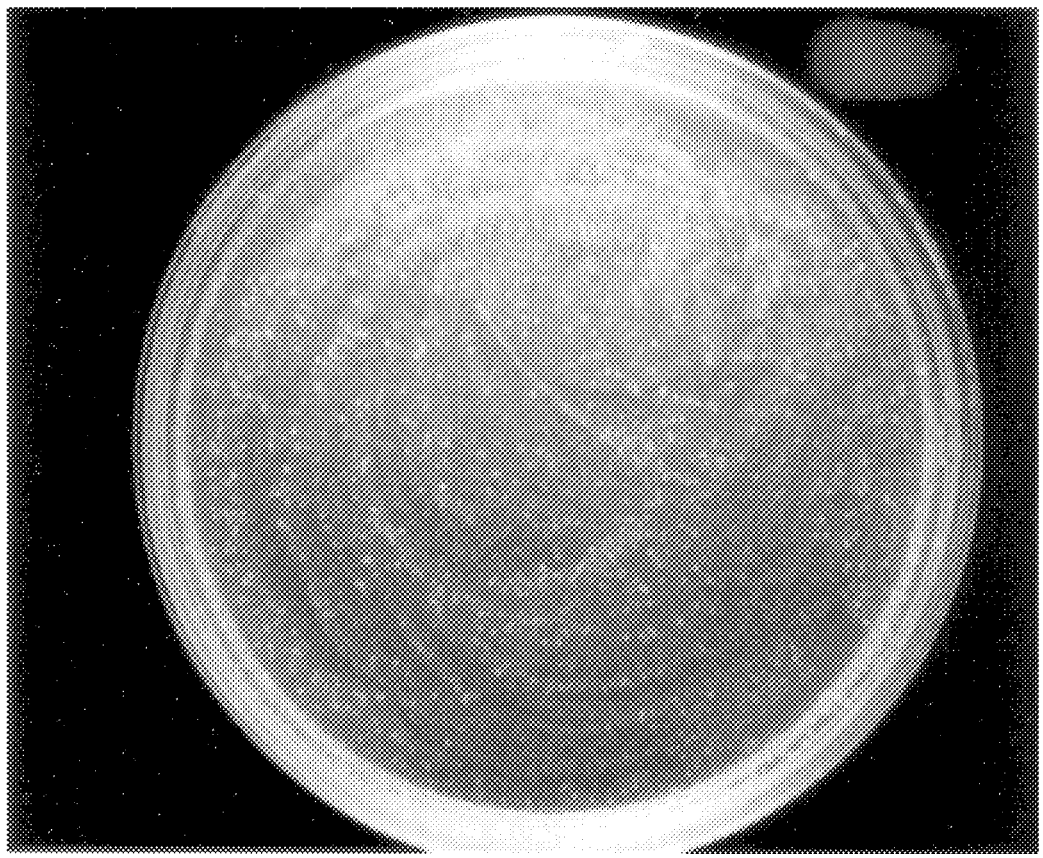
Figure 2:
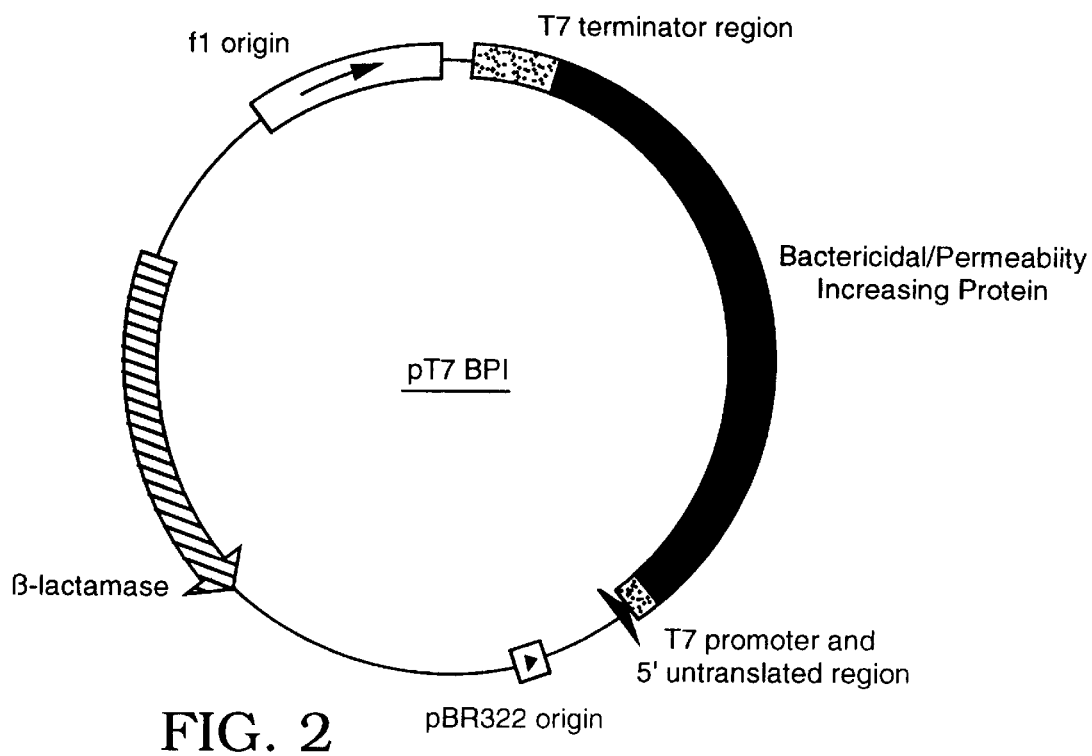

FIG. 2: Schematic of the pT7BPI Protein plasmid construct.

Figure 3:
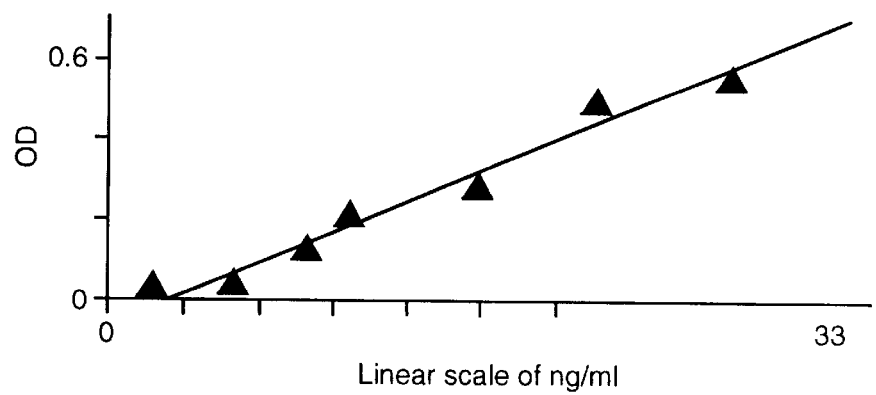

FIG. 3: Standard curve showing BPI Protein activity in ELISA Assay.

Figure 4:
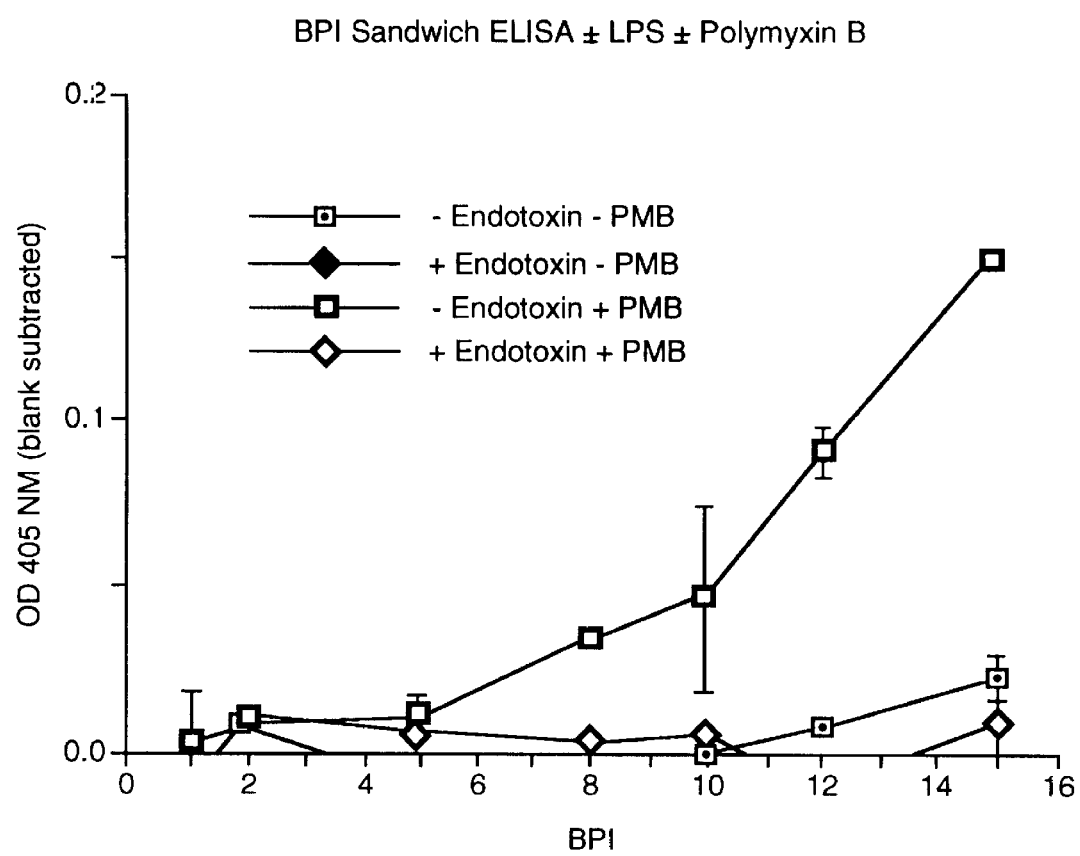

FIG. 4: BPI Protein Sandwich ELISA±endotoxin±Polymyxin B. The protocol is as follows: BPI Protein was performed in the presence and absence of 1 μg/ml of polymyxin B sulfate and the presence or absence of 1 μg/ml E. coli 0111 B4 endotoxin using PBS+1% BSA as diluent.

Figure 5:
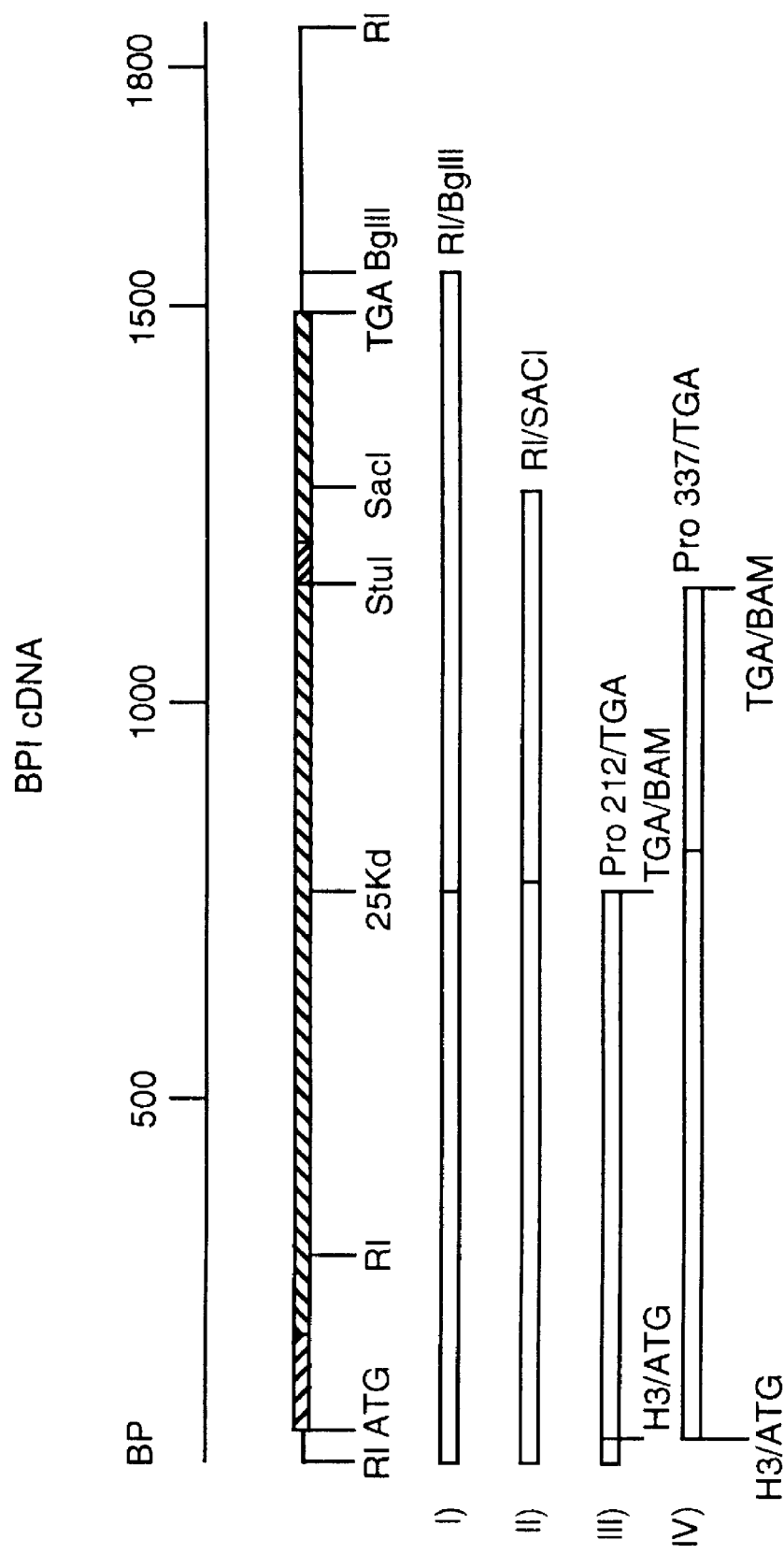

FIG. 5: Schematic drawing of cDNA encoding BPI.

FIG. 6: A nucleotide (SEQ ID NO:2) and amino acid (SEQ ID NO:1) sequence of BPI Protein mutagenic primer 25 kDa Pro 212 TGA which is a C-terminal truncation of BPI Protein.

FIG. 7: A nucleotide (SEQ ID NO:6) and amino acid (SEQ ID NO:5) sequence of BPI Protein mutagenic primer 38 kDa Pro 337 TGA which is a C-terminal truncation of BPI Protein.

FIG. 8: A nucleotide (SEQ ID NO:10) and amino acid (SEQ ID NO:9) sequence of BPI Protein mutagenic primer: Preferred ATG 5' HindIII which is a C-terminal truncation of BPI Protein.

Figure 9:
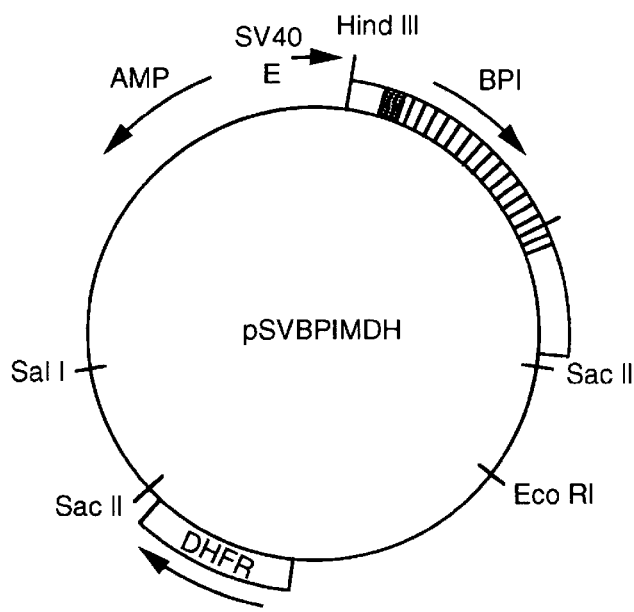

FIG. 9: A schematic drawing of pSVBPIMDH.

FIG. 10A–10B: A schematic drawing of pAc373.

Figure 11:
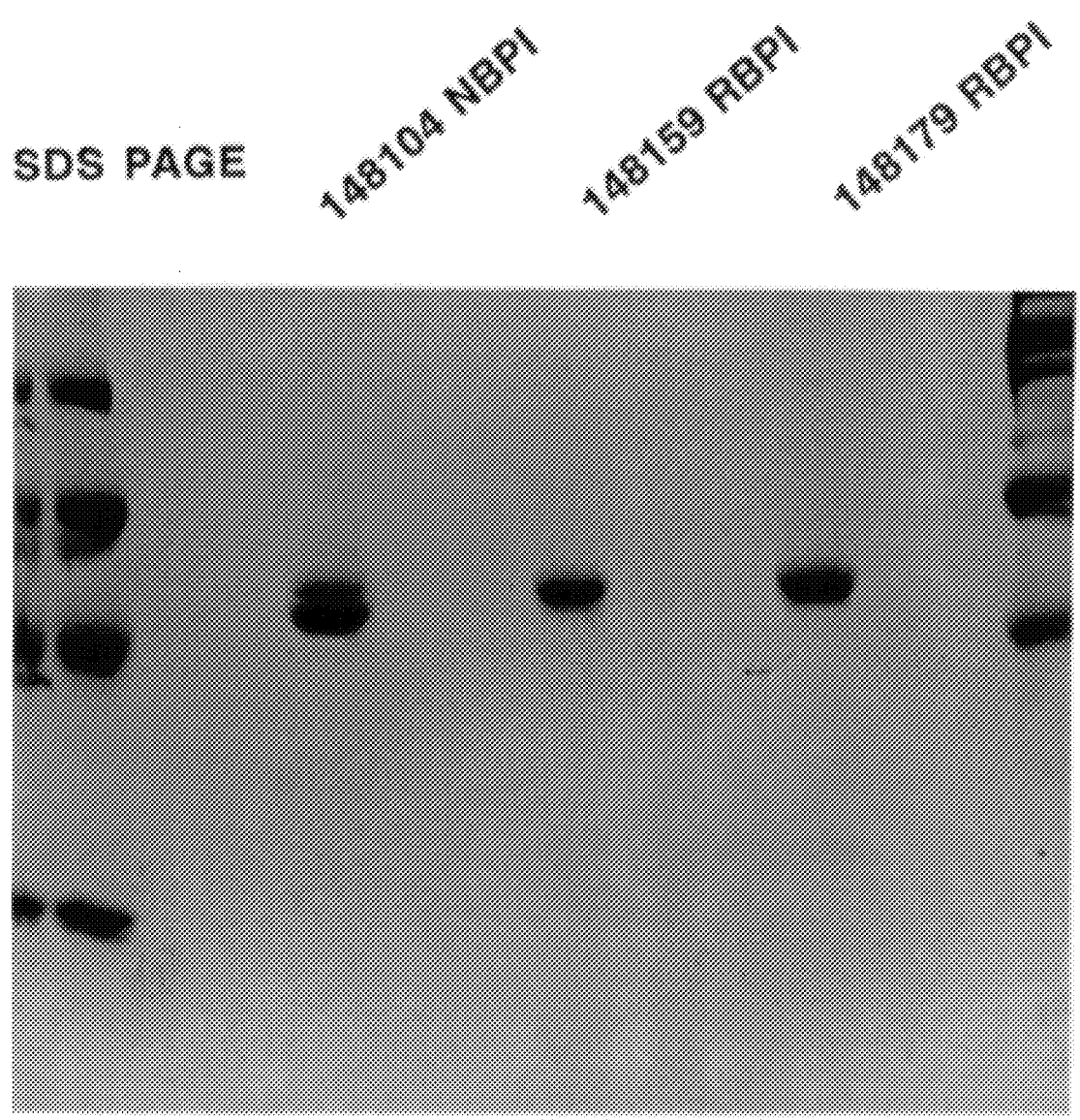

FIG. 11: SDS-PAGE analysis of (1) nBPI Protein (Lot No. #148104), (2) rBPI Protein (Lot No.#148159), and (3) rBPI Protein (Lot No. #148179).

FIG. 12A–12D: cDNA sequence (SEQ ID NO:14) of BPI.

FIG. 13: Protein sequence (SEQ ID NO:15) for p337.

FIG. 14: Protein sequence (SEQ ID NO:16)for p212.

Figure 15:
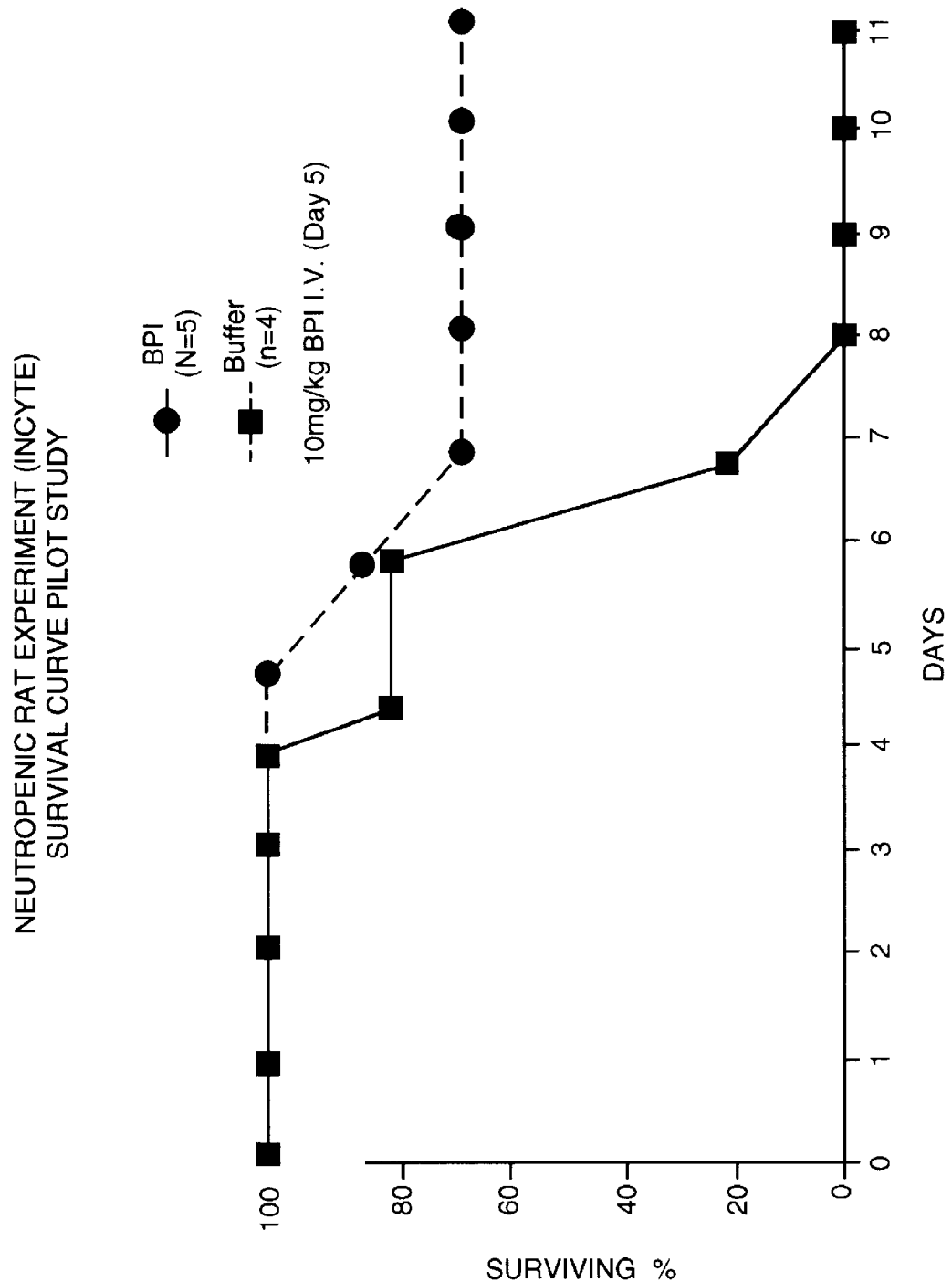

FIG. 15: Line graph showing BPI efficacy using neutropenic rat models.

Figure 16:
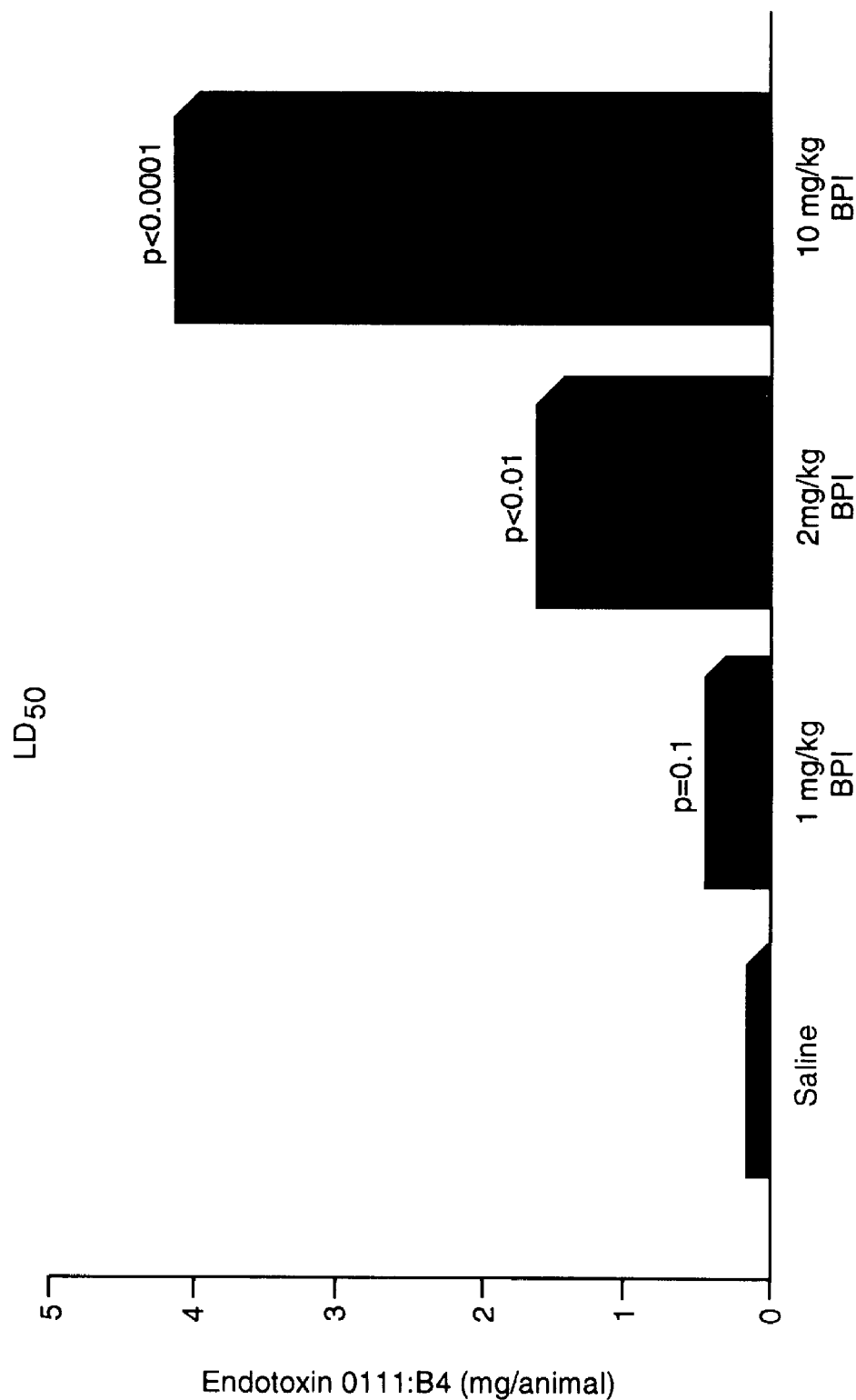

FIG. 16: Bar graph showing BPI efficacy in vivo.

Figure 17:
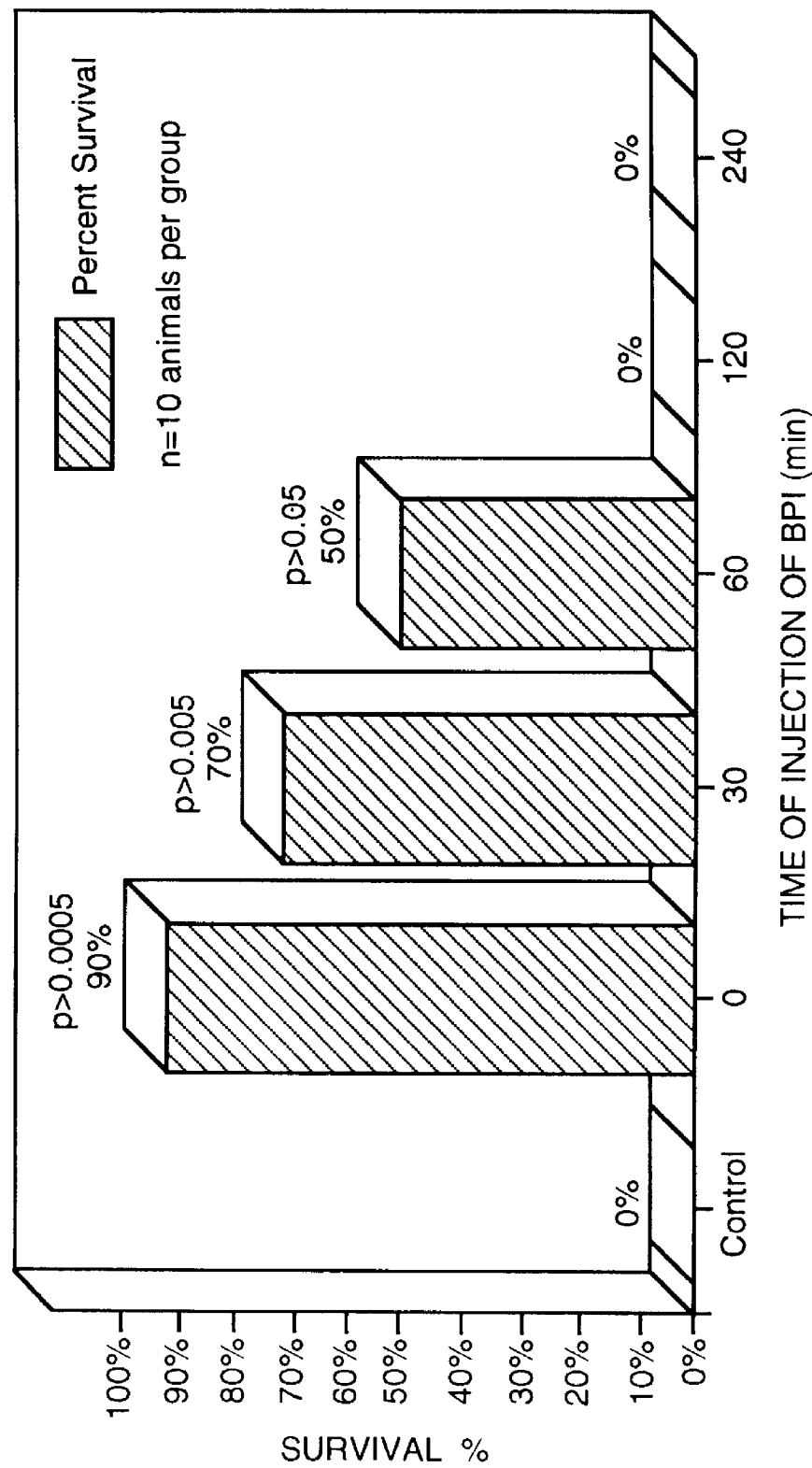

FIG. 17: Bar graph showing BPI efficacy.

Figure 18:
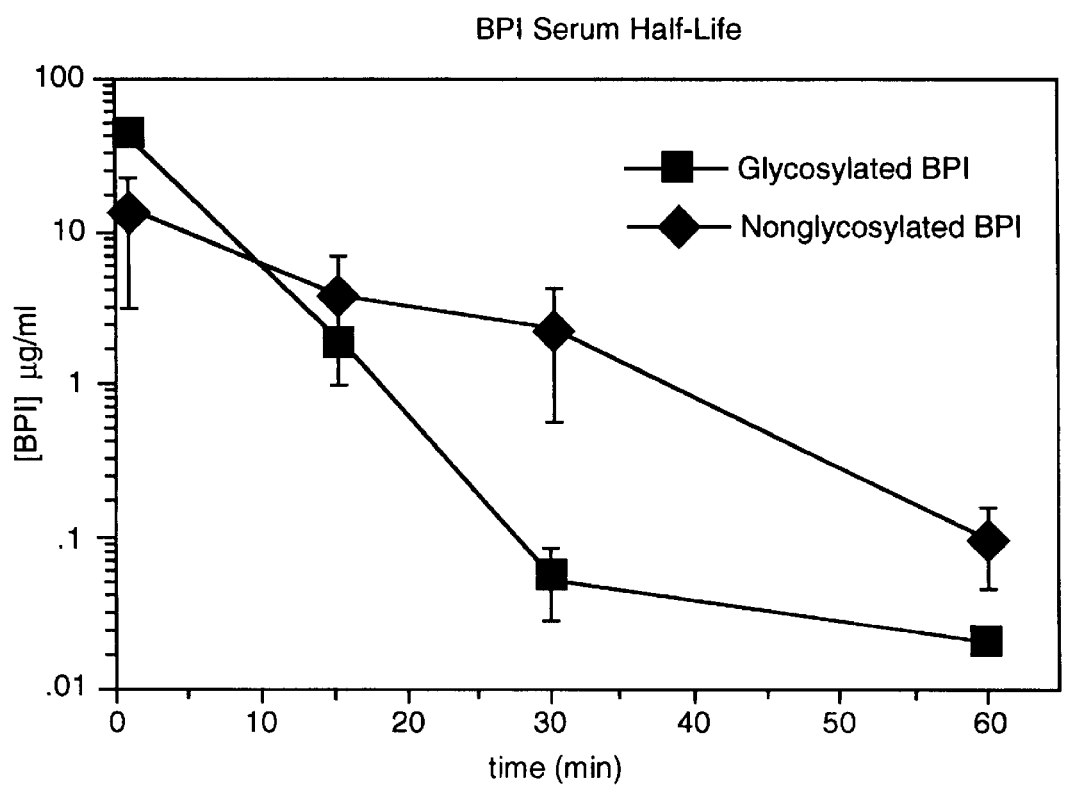

FIG. 18: Line graph showing BPI serum half life.

Figure 19:
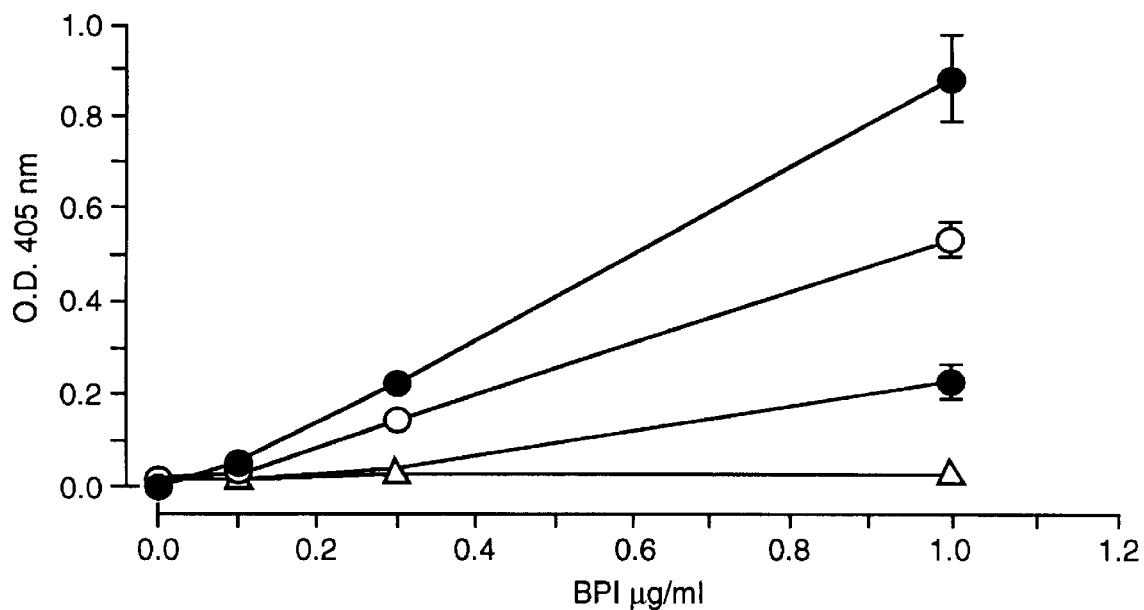

FIG. 19: Line graph showing BPI binding to endotoxin. BPI binding was assayed on endotoxin coated wells which were treated with varying concentrations of polymyxin B sulfate. Results show absorbance (O.D. 405) for buffer control (closed circles). 10 μg/ml polymyxin B (open circles). 100 μg/ml polymyxin B (closed triangles). 1 mg/ml polymyxin B (open triangles). Data is represented as the mean±SK of quadruplicate values.

Figure 20:
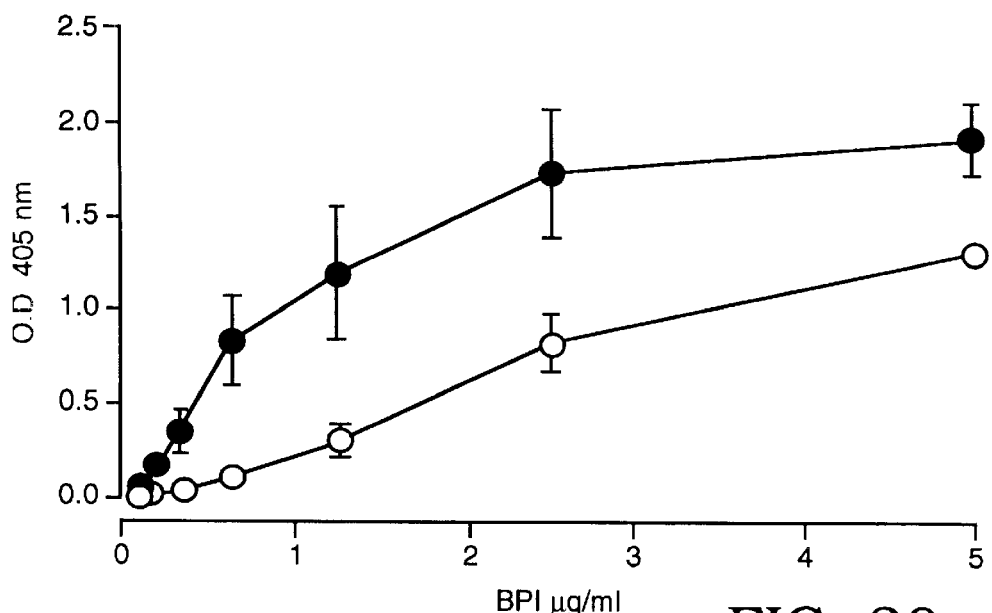

FIG. 20: Line graph showing BPI endotoxin binding. BPI was diluted in buffer (closed circles) or neat plasma (open circles) and assayed for endotoxin binding.

Figure 21:
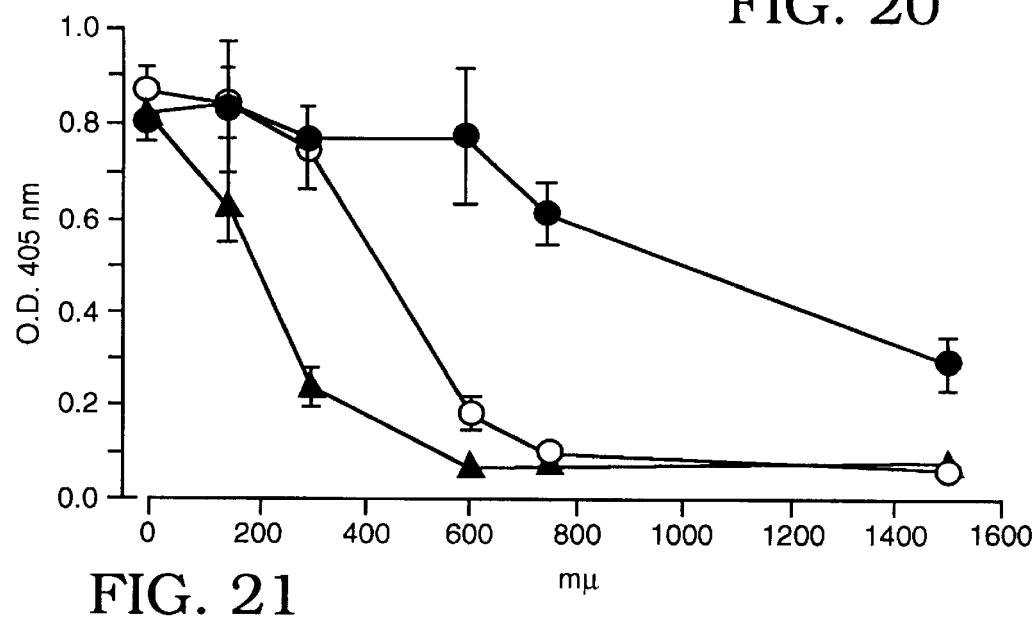

FIG. 21: Line graph showing BPI endotoxin binding. BPI was diluted in increasing concentrations (expressed as ionic strength, mμ) of NaCl (closed circles), MgCl$_2$ (open circles), or CACl$_2$ (closed triangles), and assayed for endotoxin binding as described.

Figure 22:
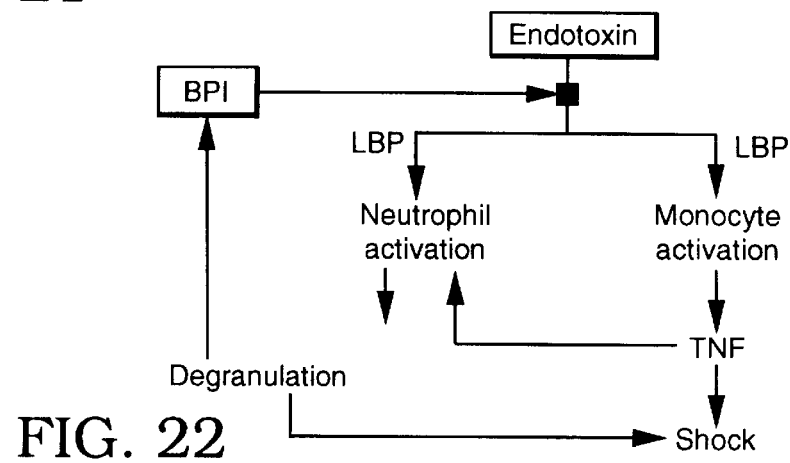

FIG. 22: A schematic diagram showing the role of BPI and LBP in regulating endotoxin activity.

FIG. 23: A biologically active variant designated LBP/BPI Chimera (SEQ ID NO:17).

FIG. 24: A biologically active variant designated CHO-BPI (SEQ ID NO:18).

FIG. 25: A biologically active variant designated BPI (DP linkage) (SEQ ID NO:19).

FIG. 26: A construct (SEQ ID NO:27) for making biologically active variants of BPI.

DETAILED DESCRIPTION OF THE INVENTION

As used in this application, the following words or phrases have the meanings specified.

As used herein, "BPI" means a native or naturally occurring biologically active human 57 kd protein which binds to the outer membrane of susceptible gram negative bacteria.

As used herein, "biologically active polypeptide fragment of BPI" means a polypeptide of molecular weight less than 57 kd, having the biological activity of, and an amino acid sequence present within, BPI.

As used herein, "biologically active polypeptide analogs of BPI" means a polypeptide which has substantially the same amino acid sequence as, and the biological activity of, BPI. Biologically active polypeptide analogs of BPI include polypeptide, the sequence of which varies from the sequence of BPI by a changed amino acid within the BPI sequence, e.g. a mutation, or by the addition of one or more amino acids at the amino- or carboxy- terminus, or both, of the BPI sequence.

As used herein, "biologically active variant of BPI" means a polypeptide that (1) includes a portion of the amino acid sequence which is present within BPI and an amino acid sequence which is not present within BPI, and (2) has substantially the same biological activity, i.e. endotoxin-neutralizing activity, as BPI.

As used herein, "recombinant" means a polypeptide produced by genetic engineering methods. Thus, each of BPI, biologically active polypeptide fragments of BPI, biologically active polypeptide analogs of BPI, and biologically active variants of BPI may be recombinant. However, in the context of this application, BPI is not the same as recombinant BPI, the latter differing in some molecular characteristic from the native or naturally occurring polypeptide, e.g. in glycosylation pattern.

As used herein, BPI Protein means (1) BPI, (2) a biologically active fragment of BPI, (3) a biologically active polypeptide analog of BPI, or (4) a biologically active variant of BPI, each of which may be either recombinant or nonrecombinant.

The present invention provides a composition comprising a BPI Protein and an anionic compound which composition exhibits (1) no bactericidal activity and (2) endotoxin neutralizing activity.

In accordance with the practice of this invention, the anionic compound could be a protein, a proteoglycan (for example heparin) or a synthetic polymer (for example dextran sulfate or polyglutamic acid). Preferably, the anionic compound is a protein such as serum albumin.

This invention also provides a biologically active variant of BPI which (1) specifically binds to endotoxin, (2) competes with BPI Protein for binding to endotoxin, and (3) inhibits endotoxin-induced lethality.

As used in this application the term "endotoxin" means a bacterial toxin which is pyrogenic.

One example of a biologically active fragment of BPI is shown in FIG. 13 (SEQ ID NO:15). Another example of a biologically active fragment of BPI is shown in FIG. 14 (SEQ ID NO:16).

Additionally, examples of a biologically active variant of BPI is shown in FIG. 23 (SEQ ID NO:17). Another example of a biologically active variant of BPI is shown in FIG. 24 (SEQ ID NO:18). Further, yet another example of a biologically active variant of BPI is shown in FIG. 25 (SEQ ID NO:19).

The present invention further provides a method for producing and secreting a recombinant BPI Protein from a cell. This method comprises (a) constructing a vector comprising DNA encoding BPI Protein; (b) transfecting the cell with the vector; and (c) culturing the cell so transfected in culture medium under conditions such that BPI Protein is secreted. In accordance with this invention, the vector further comprises a signal sequence.

In accordance with this method, mammalian cells are preferred. Examples of a mammalian cell includes, but is not limited to, HeLa, CHO, DUX B11, Sp2/0, W138, DHK, HEPG2, and COS-1 cells.

This invention also provides a BPI Protein produced by the above-described method. In one embodiment the BPI Protein is a recombinant BPI Protein designated 148159 rBPI protein shown in FIG. 11. Additionally, the invention provides a recombinant BPI protein designated as 148179 rBPI protein shown in FIG. 11.

Interestingly, recombinant BPI Protein produced in mammalian cells such as Chinese hamster ovary (CHO) cells exhibit a slightly altered migration pattern on sodium dodecyl sulfate polyacrylamide gel electrophoresis (SDS-PAGE) indicating that the molecule may also be processed differently in mammalian cells than in neutrophils or HL60 cells. Such processing may be either responsible for, or a result of, the molecule being secreted rather than packaged into granule membranes.

This invention also provides a glycosylated BPI Protein.

In accordance with the above described method, the BPI Protein so secreted may be a full length soluble BPI Protein.

Also, the present invention provides a method for producing a recombinant BPI Protein from a bacterial cell. This method comprises (a) constructing a vector without a signal sequence and comprising DNA encoding BPI Protein; (b) transfecting the bacterial cell with the vector; and (c) culturing the bacterial cell so transfected in culture medium under conditions such that recombinant BPI Protein is produced. An example of a bacterial cell includes but is not limited to *E. coli*.

BPI Protein has been shown to be toxic to bacteria, however, the toxic effects of the BPI Protein so produced against bacteria may be overcome by deleting the normal leader sequence in the vector comprising the BPI protein cDNA.

Apparently, when the signal sequence is included in the expression plasmid as provided in a full length clone and reported by Gray et al. ((1989) Journ. of Biol. Chem., 2:9505) no bacterial colonies are obtained, whereas, numerous colonies can be obtained if the signal sequence is deleted. Further, the method described hereinabove provides for expression of full length BPI Protein in a nonglycosylated form. The invention further provides for a nonglycosylated form of BPI Protein which is free from glycosylated BPI Protein.

The subject invention further provides a method for producing a recombinant BPI Protein from an insect cell. This method comprises (a) constructing a vector without a signal sequence and comprising DNA encoding BPI Protein; (b) transfecting the insect cell with the vector; and (c) culturing the insect cell so transfected in culture medium under conditions such that BPI Protein is secreted.

In one example of the above-described method, insect cells function as hosts for a baculovirus vector containing a sequence encoding the BPI Protein. Also, BPI protein derived from insect cells exhibit a different migration pattern on SDS-PAGE than that derived from either mammalian cells or the BPI protein found naturally-occurring in neutrophils. Thus, the invention provides for a new molecular species of BPI Protein as processed by baculovirus infected insect cells.

Further, this invention provides a biologically active variant of BPI produced by the above-described method.

Also, this invention provides a method for determining the amount of endotoxin in a sample from a subject which comprises contacting the sample with a BPI Protein under conditions such that an endotoxin-BPI Protein complex is formed, detecting the amount of the complex so formed thereby determining the amount of endotoxin in the sample.

Additionally, the present invention provides a method for determining the amount of endotoxin in a sample containing bound and unbound endotoxin from a subject. This method comprises (a) treating the sample so as to denature any endotoxin binding protein to which the endotoxin may be bound thereby obtaining unbound endotoxin; (b) contacting the treated sample with a BPI Protein under conditions such that the BPI Protein binds to unbound endotoxin of step (a) so that a endotoxin-BPI Protein complex is formed; (c) detecting the amount of the complex so formed thereby determining the amount of endotoxin in the sample.

In accordance with the invention, denaturation in step (a) may be effected using an elevated temperature. For example, the elevated temperature may be 95° degrees centigrade. Alternatively, denaturation may be effected with an acid.

This present invention also provides a method of detecting endotoxin in a sample which comprises contacting the sample with a BPI Protein such that the endotoxin binds to the BPI Protein and forms a complex therewith; and detecting such complex.

In one example of the invention, the sample containing endotoxin is transferred onto a suitable support under conditions permitting endotoxin in the sample to attach to the support prior to contacting the sample with BPI Protein labeled with a detectable moiety.

This invention further provides a method for diagnosing endotoxemia in a subject which comprises obtaining from the subject a biological fluid sample, detecting endotoxin in such sample using the above-described method and thereby diagnosing such disorder. The sample may be a cellular sample. Alternatively, the sample may be a biological fluid sample such as serum, urine, blood, a tissue extract, or sputum.

In accordance with the practice of the invention, the BPI Protein may be labeled with a fluorescent label and detection may be effected by a fluorometer. Alternatively, the BPI Protein may be labeled with a radioactive label and detection may be effected by a radiograph. Further, the BPI Protein may be labeled with an enzyme and detection may be effected by a spectrophotometer.

The present invention further provides a method for coating a surgical tool with a BPI Protein so that the BPI Protein will complex with endotoxin which method comprises attaching BPI Protein onto a surface of the tool which surface is designed for contact with a biological sample.

Also, this invention provides a method for coating an implantable, invasive device with a BPI Protein so that it will form a complex with endotoxin which method comprises attaching BPI Protein onto a surface of the device which surface is designed for contact with a biological sample.

In accordance with the practice of the present invention, the biological sample may be blood. Alternatively, the biological sample may be a tissue sample. Further, the biological sample may be a muscle sample. Also, the biological sample may be cartilage. Additionally, the biological sample may be bone.

Also, in accordance with the practice of this invention, the surgical tool may be a catheter tubing.

Alternatively, the surgical tool may be a surgical staple.

Further, in accordance with the practice of this invention, the device may be a surgical implant.

The present invention further provides a method for decontaminating a fluid containing endotoxin prior to administration of the fluid into a subject which comprises contacting the fluid with BPI Protein prior to administration, under conditions such that endotoxin forms a complex with BPI Protein, thereby decontaminating the fluid. The fluid may be blood, plasma, blood serum, an isotonic solution, a pharmaceutical agent, a cell culture reagent, or bone marrow.

This invention also provides a kit for detecting the presence of BPI Protein in a biological fluid sample which comprises (a) polymyxin B in an assay buffer which binds unbound endotoxin molecules; (b) a first antibody attached to a surface area containing the assay buffer, which antibody (1) binds to a portion of active BPI Protein and (2) does not compete with BPI Protein for an endotoxin binding domain; and (c) a second antibody labeled with a detectable moiety which antibody (1) does not compete with the first antibody for BPI Protein binding and (2) specifically binds to BPI Protein at or near the endotoxin binding site, so that when the biological fluid sample is contacted with the first and second antibody an active BPI Protein contained in the biological fluid sample is bound by the first and second antibody thus forming a first antibody-BPI Protein-second antibody complex, detecting such complex, and thereby detecting BPI Protein in the biological fluid sample.

Also, this invention provides a kit for determining the amount of BPI Protein in a biological fluid sample which comprises (a) polymyxin B in an assay buffer which binds unbound endotoxin molecules; (b) a first antibody attached to a surface area containing the assay buffer, which antibody (1) binds to a portion of active BPI Protein and (2) does not compete with BPI Protein for an endotoxin binding domain; and (c) a second antibody labeled with a detectable moiety which antibody (1) does not compete with the first antibody for BPI Protein binding and (2) specifically binds to BPI Protein at or near the endotoxin binding site, so that when the biological fluid sample is contacted with the first and second antibody an active BPI Protein contained in the biological fluid sample is bound by the first and second antibody thus forming a first antibody-active BPI Protein-second antibody complex, detecting such complex, and determining the amount of active BPI Protein in the biological fluid sample.

Additionally, this invention provides a method for preventing endotoxemia in a subject which comprises administering to the subject an amount of a BPI Protein effective to bind to endotoxin so as to prevent endotoxemia in the subject.

The present invention provides a method for treating a subject suffering from endotoxemia which comprises administering to the subject an amount of a BPI Protein effective to bind endotoxin so as to treat the subject suffering from endotoxemia.

In accordance with the practice of the invention, the effective amount of the BPI Protein for preventing endotoxemia or treating a subject suffering from endotoxemia may be between about 0.1 and about 10 mg/kg body weight of subject. Also, the effective amount may be an amount between about 1 and about 10 mg/kg body weight of subject.

This invention is illustrated in the Experimental Details section which follows. This section is set forth to aid an understand of the invention but is not intended to, and should not be construed to, limit in any way the invention as set forth in the claims which follow.

EXPERIMENTAL DETAILS

EXAMPLE 1

Materials and Methods

Reagents and Solutions: endotoxin from *E. coli* 0111:B4 and from *S. typhimurium* RE mutant were purchased from RIBI Immunochem Research, Inc., Hamilton, MT. FMLP, cytochalasin B and polymyxin B sulfate (7900 U/mg) was purchased from Sigma Chemical Co., St. Louis, Mo. Natural human tumor necrosis factor was purchased from Endogen Inc., Boston, Mass. HBSS without calcium and magnesium and RPMI 1640 were purchased from Gibco BRL, Grand Island, N.Y.

BPI Purification: BPI was purified from neutrophil granule preparations as previously described (Marra, M.N. et al. J. Immunol. 144: 662, 1990) with the exception that the purification was performed under rigorously pyrogen-free conditions using new, pyrogen-free columns and de-pyrogenated buffers. Buffers were deyprogenated using a Pyrosart filter (Sartorius Filters, Hayward, Calif.). Purification of BPI under these conditions resulted in material with approximately four-fold greater activity for neutralizing endotoxin-mediated neutrophil stimulation than previously reported (Marra, M. N. et al. J. Immunol. 144: 662, 1990).

Immunoaffinity purification of anti-BPI antibodies: Sera was collected from rabbits immunized with a 20 amino acid peptide corresponding to the N-Terminal 20 amino acids of the BPI molecule (BPI peptide 1–20). The IgG fraction of pooled sera was purified using Protein A Sepharose (Pharmacia, Piscataway, N.J.). Specific anti-peptide IgG was purified from this fraction using BPI peptide 1–20 coupled to activated CNBr Sepharose (Pharmacia). Bound IgG was collected and pooled, and the adsorbed IgG was further depleted of residual specific antibody by passing over the peptide column three additional times to generate immunoadsorbed negative control. Antibody concentration was determined by optical density at 280 nm. Immunoaffinity purified and adsorbed IgG were tested for specificity by Western blotting. No activity was observed in the immunoadsorbed control IgG, even at concentrations $10^3$-fold greater than that utilized for the immunoaffinity purified antibody.

Endotoxin Binding Assay: BPI binding to endotoxin immobilized on microtiter plates was performed using a modified procedure described by Tobias, P. S. et al. J. Biol. Chem. 264:10867, 1989. Briefly, Immulon 2 96 well microtiter plates (Dynatech Biotechnology Products, Chantilly, Va.) were coated with 4 µg/well glycolipid from *Salmonella typhimurium* RE mutant in 50 mM borate pH 9+20 mM EDTA overnight at 37° C. Plates were then washed extensively under running distilled deionized water, then dried at 37° C. Assay plates were blocked for 30 minutes at 37° C. with 5 mg/ml very low endotoxin BSA (Sigma, St. Louis, Mo.) prepared in pyrogen-free PBS. Plates were flicked, and in some experiments polymyxin B was added to the wells and incubated for an additional 30 minutes at 37° C. Plates were flicked again, and BPI samples were added. All buffers containing BPI or polymyxin B were prepared in pyrogen-free PBS. BPI samples diluted in pyrogen free buffer, or in some experiments, serum or plasma from normal human volunteers, were incubated for 3 hours at 37° C. with shaking. The plates were washed with PBS containing 1 mg/ml pyrogen free BSA, then developed, using rabbit polyclonal anti-BPI peptide IgG antibody as described followed by goat-anti-rabbit IgG-alkaline phosphatase conjugate (Gibco BRL Life Technologies, Inc., Grand Island, N.Y.). Absorbances were read at 405 nm on a Vmax kinetic microplate reader (Molecular Devices Inc., Menlo Park, Calif.).

EPI inhibition of endotoxin mediated TNF induction by human adherent mononuclear cells: Blood collected in acid citrate dextrose containing vacutainer tubes (Becton Dickinson, Rutherford, N.J.) was diluted in Hank's balanced salt solution (HBSS) minus $Ca^{2+}$ and $Mg^{2+}$. Mononuclear cells were separated using Ficol-Paque (Pharmacia Inc., Piscataway, N.J.), collected and washed three time in HBSS, and the proportion of monocytes was estimated by microscopic examination. Cells were brought up to an appropriate volume of RPMI 1640 with glutamine and antibiotics and without serum to give approximately $1 \times 10^6$ monocytes/ml. Cells were plated into 96 well flat bottom tissue culture plates (Costar, Cambridge, Mass.), 200 µl/well, and incubated for 2 hours at 37° C. in a humidified incubator with 7% $O_2$. Cells were then washed three times in warm RPMI 1640 without serum. After the last wash was aspirated, 200 µl/well RPMI 1640 with 10% autologous heat inactivated serum was added. To each well was then added the 22 µl of 10X solution of *E. coli* Endotoxin preincubated in buffer, polymyxin B, or BPI. Cells were incubated with the endotoxin mixture for 4 hours at 37° C., then the supernatants were collected and assayed for TNFA antigen by ELISA (Endogen Inc., Boston, Mass.).

Inhibition of endotoxin-induced TNFA secretion by murine broncheoalveolar macrophages: Normal anesthetized Swiss-Webster mice were challenged by the intranasal route with long E. coli 0111:B4 endotoxin (List, Campbell, Calif.). Twenty minutes before challenge, anesthetized mice were treated by the intranasal route with 50 µl saline, BPI or polymyxin B solution. At one hour after endotoxin challenge, mice were re-anesthetized, and 0.7 ml of saline containing 1% human serum albumin was added to the lungs via the trachea. The lungs were gently kneaded. A 0.5 ml volume bronchoalveolar lavage (BAL) fluid was aspirated, cells were pelleted by centrifugation, and the BAL sample was stored at −70° C. The TNFα level in the BAL fluid was determined by measuring cytotoxicity towards WEHI clone 13 mouse fibrosarcoma cells. Human rTNFα (Chiron, Emeryville, Calif.) was used as the standard.

RESULTS

BPI binds to bacterial lipopolysaccharide: Binding of BPI to endotoxin was demonstrated using a modified ELISA protocol to detect BPI bound to immobilized S. typhimurium Re endotoxin as described in Methods above. BPI had bound endotoxin in a concentration dependent manner and binding was inhibited by polymyxin B/ suggesting that BPI binds at or near lipid A (FIG. 19). Significant binding of BPI to endotoxin was retained in the presence of plasma (FIG. 20) or serum, thus indicating that BPI binds to endotoxin in the presence of blood proteins as well as physiologic salts. This date is consistent with the observation by Mannion, B. A. et al. (J. Clin, Invest. 86:631 1990) that BPI binds to bacteria in the presence of serum albumin, although under these conditions BPI is not bactericidal. Also, concentrations of $Ca^{2+}$ and $Mg^{2+}$ which can rescue bacteria from the lethal actions of BPI (20–80 mM) do not significantly reduce binding of BPI to endotoxin (FIG. 21).

BPI blocks endotoxin-mediated TNF secretion in vitro: Release in TNF in response to endotoxin in vivo may play an important role in pathogenesis of endotoxic shock. To investigate the role of BPI in regulating endotoxin-mediated TNF secretion, we measured TNF secretion by human adherent peripheral blood mononuclear cells in response to endotoxin and to endotoxin preincubated with BPI (Table 1). BPI specifically prevented endotoxinstimulated TNF secretion by these cells in a concentration dependent manner. In addition, inhibition by BPI could be overcome by a large excess of endotoxin (100–1000 ng/ml) or 0.1% killed S. aureus. indicating that BPI did not interfere with monocyte function but rather blocked specific activation of monocytes by endotoxin.

TABLE 1

Inhibition of endotoxin-Induced TNF Production by BPI
TNF (pg/ml)

| Endotoxin ng/ml | Buffer Control | Polymyxin 1.0 µg/ml | BPI 0.4 µg/ml | BPI 0.1 µg/ml |
|---|---|---|---|---|
| 100 | 823 ± 67 | 400 ± 148 | 530 ± 16 | 746 ± 48 |
| 10 | 756 ± 116 | 76 ± 25 | 60 ± 9 | 182 ± 42 |
| 1 | 598 ± 89 | 0 | 0 | 0 |

Human peripheral blood mononuclear cells were stimulated with E. coli 0111:B4 endotoxin wh ich had been preincubated for 30 minutes at 37° C. with buffer, BPI or polymyxin B. Supernatants were harvested four hours after endotoxin mixtures were added. Secretion of TNFA was quantitated by ELISA.

BPI blocks in vivo pyrogenicity of endotoxin: Cytokines released in response to experimental endotoxin infusion cause physiologic changes including fever induction. We studied the effects of BPI on endotoxin pyrogenicity by injecting rabbits with endotoxin or endotoxin preincubated with BPI. Resulting changes in temperature were monitored at three one-hour intervals post injection. The greatest temperature increase was used to calculate $\Sigma(\Delta T)$ for the three animals test in each group. A value of $\geq 1.4°$ C. is considered pyrogenic (U.S. Pharmacopeal Convention, Inc., 1990 Rockville, Md., Test 151, p. 1515). While a total temperature rise of 3.9° C. was observed in the group injected with 400EU of FDA reference standard endotoxin alone, endotoxin pre-treated with 2 µg BPI was not pyrogenic, showing a total temperature rise of only 1.1° C. No response was observed in buffer treated control animals or BPI treated animals.

BPI blocks endotoxin-mediated TNF secretion in vivo: To determine whether BPI could inhibit endotoxin-mediated TNFα secretion in vivo. we tested BPI neutralization of endotoxin in the murine lung. Administration of BPI into the lung twenty minutes prior to endotoxin challenge significantly reduced the amount of TNF secreted into bronchoalveolar lavage fluid by alveolar macrophages (Table 2). Four out of five saline treated mice had TNFA levels greater than 1,000 pg/ml, versus one of five for BPI. Overall, BPI reduces endotoxin-mediated TNFα secretion by murine lung alveolar macrophages by 8.2-fold. Relative to the saline control, reduction of TNF secretion by BPI was significant (using the Student's t-test) at the $p<0.05$ level. (Geometric mean±SD of saline control: 3.364±0.402, BPI treated group= 2.109±0.764). Polymyxin B was slightly more effective in reducing TNFα secretion relative to the saline control ($p<0.02$) although the dose of PMB was 50-fold greater on a molar basis than that used for BPI. These data indicate the soluble BPI neutralizes endotoxin in vivo.

TABLE 2

Effect of BPI on endotoxin-Mediated TNF Secretion by Murine BAL
TNF (pg/ml)

| Mouse | Saline Control | BPI 0.86 µg (15 pmol) | Polymyxin B 1.0 µg (782 pmol) |
|---|---|---|---|
| 1 | 1200 | 15 | 74 |
| 2 | 675 | 63 | 50 |
| 3 | 5560 | 425 | 132 |
| 4 | 2800 | 67 | 370 |
| 5 | 5250 | 1310 | 640 |
| Mean ± SD | 3097 ± 2250 | 376 ± 547 | 253 ± 251 |

Normal anesthetized mice were challenged by the intranasal route with 10 ng E. coli 0111:B4 endotoxin. Twenty minutes before challenge, anesthetized mice were treated by the intranasal route with 50 µl saline, BPI or polymyxin B solution. Bronchoalveolar lavage (BAL) fluid was assayed for TNFα by measuring cytotoxicity towards WEHI as clone 13 mouse fibrosarcoma cells. Human rTNFα was used at the standard.

Our data show that BPI specifically prevented endotoxin-stimulated TNF secretion in vitro by human adherent mononuclear cells in a concentration dependent manner. Inhibition of endotoxin-induced TNF secretion distinguishes BPI from LBP. LBP, a 60 kDa acute phase protein synthesized by hepatocytes, has 44% amino acid sequence homology to BPI and binds to endotoxin in vivo and in vitro (Tobias, P. S., K. Soldau, and R. J. Ulevitch. 1986. Isolation of a lipopolysaccharidebinding acute phase reactant from rabbit serum. J. Exp. Med. 164:777) (Schuman, R. R., S. R. Leong, G. W. Flaggs, P. W. Gray, S. D. Wright, J. C. Mathison, P. S. Tobias, and R. J. Ulevitch. 1990. Structure and function of lipopolysacchride binding protein. Science. 249:1429). Despite their structural similarities, BPI and LBP are functionally antagonistic. LBP-endotoxin complexes prime neutrophils for the oxidative burst response to FMLP and cause accelerated and increased TNF production by monocytes in vitro (Vosbeeck, K., L. Sklar, H. Muller, C. Lundberg, C. Hanson, K. Arfors, R. Ulevitch, and P. Tobias. 1988. Modulation of lipopolysaccharide (LPS) induced neutrophil priming by an acute phase reactant, lipopolysaccharide binding protein, LBP. Eur. J. Clin Invest. 18A50) (Wright. S. D., R. A. Ramos, P. S. Tobias, R. J. Ulevitch, and J. C. Mathison. CD14, a receptor for complexes of lipopolysaccharide (LPS) and LPS binding protein. Science. 249:1931) (Tobias, P. S., J. C., Mathison, and R. J. Ulevitch. 1988. A family of lipopolysaccharide binding proteins involved in responses to Gram-negative sepsis. J. Biol. Chem. 263:13479). In contrast, BPI blocks LPS-mediated stimulation of both neutrophils (Marra, M. N., C. G. Wilde, J. E. Griffith, J. L. Snable and R. W. Scott. 1990. Bactericidal/permeability increasing protein has endotoxin-neutralizing activity. J. Immunol. 144:662) and macrophages in vitro. Since BPI-endotoxin complexes fail to stimulate inflammatory cells in vitro. one would not expect such complexes to elicit a pyrogenic response when administered in vivo. Small quantities of endotoxin alone induce a strong pyrogenic response resulting from the release of endogenous pyrogens such as TNF, IL-1, and gamma IFN (Farley, M. M., W. M. Shafer, and J. K. Spitznagel. 1988. Lipopolysaccharide structure determines ionic and hydrophobic binding of a cationic antimicrobial neutrophil granule protein. Infect. Immun. 56:1589). Rabbits are exquisitely sensitive to trace quantities of endotoxin, and respond with a dose dependent and reproducible elevation of core temperature. In complex with BPI, endotoxin was unable to stimulate a pyrogenic response in rabbits. Thus, BPI is an effective inhibitor of endotoxin in vivo presumably a result of BPI blocking endotoxin-mediated cytokine secretion.

The bactericidal and permeability increasing activities of BPI in vitro are associated with the N-terminal half of the molecule which shares extensive homology with LBP (Schuman, R. R., S. R. Leong, G. W. Flaggs, P. W. Gray, S. D. Wright, J. C. Mathison P. S. Tobias, and R. J. Ulevitch. 1990. Structure and function of lipopolysaccharide binding protein. Science. 249:1429). No function has been ascribed to the carboxy-terminal region, other than a membrane spanning domain. Gray and colleagues (Gray, P. W., G. Flaggs, S. R. Leong, R. J. Gumina, J. Weiss, C. E. Ooi, and P. Elsbach. 1989. Cloning of the cDNA of a human neutrophil bactericidal protein. Structural and functional correlations. J. Biol. Chem. 264:9505) suggest that the carboxy-terminal half of BPI is associated with the azurophil granule membrane. In their model, when neutrophils are stimulated, proteolytic enzymes such as elastase cleave the molecule releasing the active, bactericidal N-terminal half into the phagolysosome. Several lines of evidence, however, argue against BPI as an integral membrane protein. BPI can be extracted from isolated azurophil granules in the absence of detergents. BPI is soluble in aqueous solutions and soluble BPI is active in tests for both endotoxin binding and inhibition. Also, BPI is released by FMLP/cytochalasin B stimulated neutrophils (71% of total cellular BPI) as a full-length, protein, arguing against release of the N-terminus by neutrophil proteases upon degranulation.

In vivo, BPI likely functions to suppress endotoxin toxicity and not as a bactericidal protein. Endotoxin binding proteins such as LBP and BPI may function respectively as a receptor/receptor-antagonist system to regulate the host response to endotoxin (FIG. 22). LBP acts as a soluble receptor for endotoxin and amplifies the effects of endotoxin on both neutrophils and macrophages. The ability of BPI to limit the host response to endotoxin indicates that BPI may have an important role in blocking lethal effects of endotoxin in vivo. Preliminary results in animals (see Example 4) show that treatment with recombinant BPI markedly reduces endotoxin-induced lethality. Thus, use of BPI to neutralize endotoxin, in conjunction with conventional antibiotics to limit bacterial growth, may be a useful therapy against endotoxic shock.

EXAMPLE 2

Expression of BPI Proteins and BPI-Truncated Forms

A. Genetically Engineered Mammalian Cells Express BPI

In order to produce BPI protein and/or BPI protein variants in mammalian cells, the cDNA sequences must be inserted into a suitable plasmid vector. A suitable vector for such an application is pSV-1, which contains the origin of replication and early and late promoters of SV40, followed by multiple insert cloning sites, followed by the termination sequences from the hepatitis B surface antigen gene. Also contained within the plasmid are an origin of bacterial DNA replication, and the genes encoding ampicillin resistance and dihydrofolate reductase. Similar vectors have been used to express other foreign genes (McGrogan, et.al. Biotechnology 6, 172–177). Vector DNA was prepared for acceptance of BPI protein cDNA sequences by digestion with HindIII and Bam HI, and dephosphorylation with alkaline phosphatase.

Several BPI protein cDNA-containing inserts were prepared for insertion into pSV-1. First, an insert encoding full-length BPI protein was prepared by digestion of the parent plasmid with appropriate restriction enzymes for ex. EcoRI and Bgl II, yielding two DNA fragments containing portions of the BPI protein coding sequence. These two fragments were ligated together into prepared SV-1, and the recombinant clones obtained were screened by restriction enzyme digestion for the presence of the two inserts in the proper orientation. Two cDNAs encoding truncated forms of BPI protein were generated using oligonucleotide-directed DNA amplification of the parent BPI protein insert DNA. The amplifying oligos were designed to replace codons 212 (oligo 459) (SEQ ID NO:4) (FIG. 6) and 337 (oligo 460) (SEQ ID NO:8) (FIG. 7) with stop codons, in addition to a BamHI cloning site (FIG. 5). At the 5' end of both constructs, oligo 458 (SEQ ID NO:11) was used in the amplifications to create a HindIII site immediately upstream of the translational start codon ATG (FIG. 8). Thus, three BPI-encoding inserts were created, each encoding 55 kDa, 38 kDa, and 25 kDa forms of BPI, and each was ligated separately into prepared vector DNA.

Each of the three constructs was verified by restriction digest analysis, and then prepared in amounts sufficient for transfection into CHO cell line DUXB11 cells. Transfection was performed using lipofectin, and the resulting transformed cells were selected in the presence of increasing amounts of methotrexate using standard protocols (FIG. 3).

Supernatants from either transfected pools or clones derived from the pools were assayed for the presence of endotoxin binding activity by inhibition of TNr release. BPI was negligible in the vast majority of the selected cell lines. We found that only cell lines established from a 500 nM methotrexate bulk amplification produced commercially reasonable quantities of BPI. Two such cell lines are designated 3A1 and 4D6. It was unexpected that only the bulk amplification resulted in such cell lines.

B. Baculovirus Expression of rBPI in Insect Cells

Figure 10:
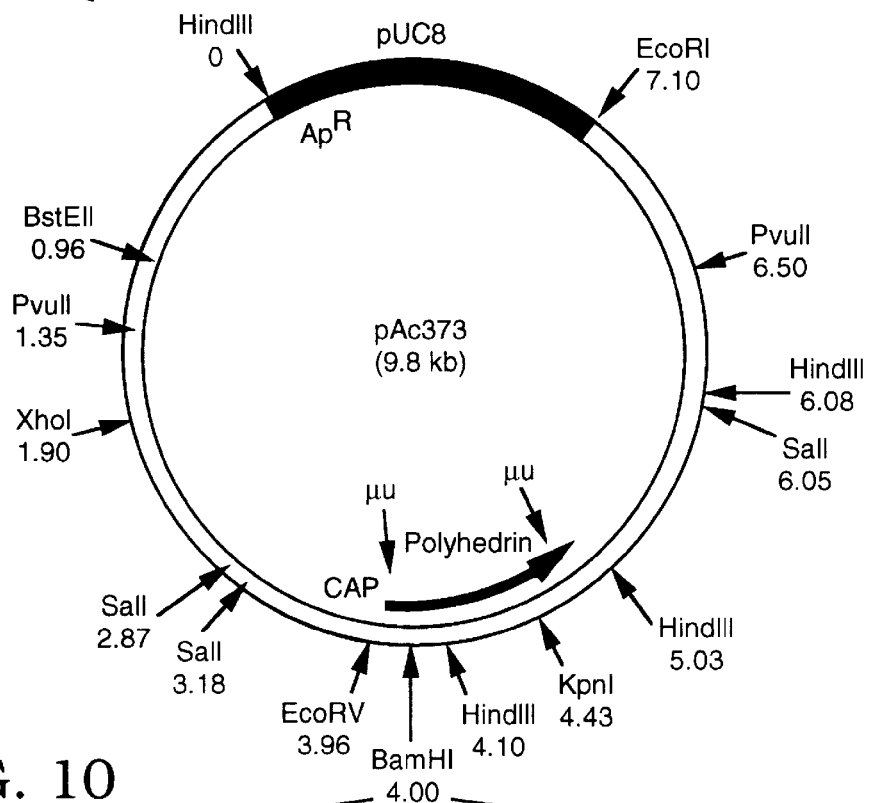

Construction of plasmid expression vector: In order to produce BPI protein and/or BPI protein variants in insect cells, the cDNA sequence must first be inserted into a suitable plasmid expression vector, such as pAC373 (FIG. 10). Appropriate restriction sites for this insertion were created by standard site-directed mutagenesis procedures. The essential properties of a suitable expression vector include a transcriptional promoter such as the polyhedron gene promoter of pAC373, and flanking homologous sequences to direct recombination into the baculovirus genome. A polyadenylation signal, such as the one from the polyhedron gene present in this plasmid vector, may or may not be necessary for expression of the recombinant gene. A marker gene such as the beta-galactosidase gene of *E. coli*, juxtaposed to regulatory sequences including a transcriptional promoter and possibly a polyadenylation signal, may be included in the vector but is not essential for BPI protein expression. A typical vector for such purposes pAC373, is shown in FIG. 10.

Creation of recombinant baculavirus: A chimeric baculovirus was created by homologous recombination between the expression plasmid containing the BPI protein target gene (or truncations thereof derived as described in Section A) and wild type baculovirus DNA. Plasmid and wild type baculovirus DNA were co-precipitated by the calcium phosphate technique and added to uninfected Spodoptera frugiperda (Sf9) insect cells. Four to seven days following transfection, cells exhibited a cytopathic morphology and contained the nuclear occlusion bodies typically produced by viral infection. The cell-free culture media containing both wild type and recombinant virus was harvested and assayed for BPI activity.

Identification and isolation of chimeric baculavirus: Clonal isolates of virus was obtained from this co-transfection stock by plaque purification on Sf9 cell monolayers overlaid with agarose. Candidate plaques for analysis will be identified by a plaque morphology negative for occlusion bodies. If the expression plasmid contains a marker gene such as beta galactosidase, recombinant plaques will be indicated by the blue color produced from a chromogenic substrate such as 5-bromo-4-chloryl-3-indolyl-β-D-galactopyranoside (X-gal) in the agarose plating medium. Picked plaques will be used for inoculation of cells in multiwell dishes. The resulting cell lysates and infected cell supernatants can be evaluated for expression of recombinant BPI, using standard activity or immunological assays. Positive wells may require additional rounds of plaque purification to obtain pure recombinant virus stocks free from wild type contamination.

Batch production of BPI: Sf9 cells are adapted to growth in serum-free, low protein medium such as ExCell (J. R. Scientific). Cells are collected from suspension culture by gentle centrifugation and resuspended in fresh medium containing the viral inoculum at a concentration of ten million cells per ml, using a multiplicity of infection of one virus plaque forming unit per cell. After a period of two hours, the culture is diluted five fold with fresh medium and incubated two to three days. At the end of that time, the cells were pelleted by centrifugation and the conditioned medium was harvested. BPI protein was purified from the cell-free supernatant by standard means.

Characterization of insect cell derived BPI: BPI protein produced in insect cells using a baculovirus expression system is a glycosylated protein of approximate molecular weight of 55,000 kd. The N-terminal amino acid sequence is identical to that of mature mammalian cell BPI, indicating correct processing of the signal sequence. The specific activity of endotoxin binding of recombinant protein was indistinguishable from BPI.

Construction of pT7BPI protein Plasmids: Oligonucleotides were prepared on an Applied Biosystems 380B DNA Synthesizer for use in oligonucleotide directed DNA amplification. The oligonucleotides created Nde I and BamHI restriction sites at the 5' and 3' ends, respectively, of the BPI protein DNA. In addition, another oligonucleotide containing a BamHI restriction site was used to create the truncated proline-212 version of the BPI protein DNA.

Following the amplification reactions, fragments were purified and digested with Nde I and BamHI. The plasmid, pGEMEX-1, (available from Promega) was selected as the vector for the constructions. pGEMEX-1 contains a T7 promoter which can be used for the expression of downstream sequences when placed into the proper host. The vector was cleaved with BamHI and, following purification, partially digested with Nde I to generate a vector with a single Nde I site and a single BamHI site. The fragments were ligated and transformed into the *E. coli* strain JM101 using the Hanahan transformation protocol (DNA Cloning Volume I, A Practical Approach, Edited by D. M. Glover, IRL Press). The transformed bacteria were plated on LB plates containing carbamicillin and incubated overnight at 37° C. Resistant colonies were selected and analyzed by preparing mini-plasmid preparations and digesting with the appropriate restriction enzymes. Digests were analyzed on both 1% agarose gels and 5% polyacrylamide gels.

The expression host, *E. coli* strain JM109(DE3), was transformed using 1 $\mu$l of the mini-plasmid preparation and the Hanahan transformation protocol. JM109(DE3) contains a chromosomal copy of the gene for T7 RNA polymerase which can be induced with IPTG. The transformed bacteria were plated on LB plates containing carbamicillin and incubated overnight at 37° C. Results are shown in FIGS. 1A–1E.

Since the full-length and proline-212 truncated forms of BPI protein containing the signal peptide do not give colonies while those forms that do not contain the signal peptide do give colonies, the BPI protein was expressed in an active form and is processed correctly, sending the protein to the periplasmic space of the bacteria (the location in bacteria that proteins possessing a signal peptide are sent to) where the bactericidal activity kills the cell. This also implies that both the fulllength form and the proline-212 truncated form are active and capable of bactericidal activity.

Whether the forms of BPI protein which do not contain the signal peptide are active or are prevented from exhibiting their bactericidal activity by being sequestered in the cell (either by the formation of inclusion bodies or by the inability to gain access to the plasma membrane due to the absence of the signal peptide or both) is not known.

rBPI was purified as follows: Conditioned media containing recombinant BPI (rBPI) was purified to 95% homogeneity in a single step over CM-Sepharose. The CM-Sepharose column (Pharmacia, Piscataway, N.J.) was first washed in five column volumes of 0.5M NaOH followed by rinsing with pyrogen free buffers or water until no pyrogen could be detected by the Limulus Amebocyte Lysate Assay (Whittaker, Walkersville, Md.). The column was then equilibrated in 50 mM Tris pH 7.4. The conditioned media was then loaded and the bound protein was eluted in 50 mM Tris 1M NaCl pH 7.4. rBPI was concentrated and further purified by loading onto a second CM-Sepharose column equilibrated in 50 mM Tris pH 7.4 and eluted using a gradient of 0.0–1.0M NaCl. BPI elutes at approximately 0.75M NaCl. rBPI thus purified appeared as a single band on SDS-polyacrylamide gel electrophoresis and as a single peak on reverse phase HPLC.

EXAMPLE 3
Inhibition of Endotoxin-Induced TNF Production by BPI

Human peripheral blood mononuclear cells were isolated on Ficoll-Paque (Pharmacia) gradients, washed 2X in pyrogen free HBSS (Hazelton), and resuspended at $5 \times 10^6$/ml in RPMI (Gibco) media without serum. Two hundred $\mu$l of this cell suspension was incubated in each well of flat-bottom 96 well tissue culture dishes (Costar) for 2 hours at 37° C. Nonadherent cells were removed by washing 2X with RPMI+10% autologous heat inactivated serum. Adherent mononuclear cells were stimulated with *E. coli* 0111:B4 endotoxin which had been preincubated for 30 minutes at 37° C. with buffer, BPI protein or polymyxin B (Gibco; 7900 U/ml). Supernatants were harvested four hours after endotoxin mixtures were added. Secretion of TNFα was quantitated by ELISA (Endogen) (results at Table 3). Several lots of natural and recombinant BPI from CHO cells were tested.

TABLE 3

| | ENDOTOXIN DOSE | | | | | | | |
|---|---|---|---|---|---|---|---|---|
| | 10 ng/ml endotoxin | | | | 1 ng/ml endotoxin | | | 0 ng/ml endotoxin |
| BPI Protein (nM): | 0 | 7.3 | 1.4 | 0.3 | 0 | 7.3 | 1.4 | 0.3 | 0 |
| Control | 626 | — | — | — | 334 | — | — | — | 113 |
| 78038n | — | 129 | 159 | 203 | — | 153 | 187 | 165 | — |
| 148104n | — | 98 | 104 | 162 | — | 98 | 119 | 162 | — |
| 148113n | — | 92 | 114 | 151 | — | 71 | 129 | 155 | — |
| 148159r | — | 82 | 158 | 155 | — | 87 | 136 | 147 | — |
| 148165r | — | 124 | 128 | 138 | — | 116 | 129 | 146 | — |
| 148179r | — | 85 | 139 | 134 | — | 93 | 131 | 166 | — | n = natural
r = recombinant

EXAMPLE 4

The pathophysiologic consequences of gram negative sepsis are primarily mediated by the release of bacterial endotoxin (LPS). Since BPI Protein has endotoxin neutralizing activity in vitro, the effects of BPI Protein in vivo were studied in experimental models of endotoxic shock.

Specifically, in one experiment one group of 8 rats (Sprague Dawley rats) was given a single, bolus injection of 1 mg BPI Protein per kg body weight four hours before a single intravenous bolus of 0.5 mg/kg body weight 0111:B4 endotoxin obtained from Sigma. In the same experiment, a second group of 8 rats was given a single bolus injection of 1 mg BPI Protein per kg body weight simultaneously with a single intravenous bolus of 0.5 mg/kg body weight 0111:B4 LPS. Further, a third group of 5 rats was given a single bolus injection of 1 mg BPI Protein per kg body weight four hours after a single intravenous bolus of 0.5 mg/kg body weight 011:B4 LPS. Finally, a fourth group of 10 rats was treated with endotoxin alone. The rats were observed for 48 hours and the survival recorded for each group. The results of this experiment are shown in Table 4. Rats to which endotoxin alone was administered exhibited a mortality rate of 80%. Rats which received both BPI Protein and endotoxin showed a significantly reduced mortality rate.

The results set forth in Table 4 establish BPI Protein is useful in vivo both to prevent and to treat disorders associated with the presence of endotoxin. High dose BPI Protein toxicity studies revealed no evidence of toxicity when the animals were sacrificed at 7 days. We conclude BPI is a non-toxic naturally occurring protein which binds LPS, inhibits release of TNF and reduces mortality in both endotoxin and GNB experimental sepsis models (FIG. 17). We believe BPI Protein offers a novel immunotherapeutic approach to the management of septic shock.

TABLE 4

INVESTIGATION OF THE POTENTIAL PROTECTIVE EFFICACY OF BPI IN THE RAT ENDOTOXIN CHALLENGE MODEL

| Endotoxin Dose Survival | BPI Protein Dose | BPI Protein Administration Regimen | % |
|---|---|---|---|
| 0.5 mg/kg (2/10) | — | — | 0 |
| 0.5 mg/kg (6/8) | 1 mg/kg | 4 hr pre-injection | 5 |
| 0.5 mg/kg | 1 mg/kg | simultaneous | 5 |

TABLE 4-continued

INVESTIGATION OF THE POTENTIAL PROTECTIVE EFFICACY OF BPI IN THE RAT ENDOTOXIN CHALLENGE MODEL

| Endotoxin Dose Survival | BPI Protein Dose | BPI Protein Administration Regimen | % |
|---|---|---|---|
| (4/8) 0.5 mg/kg (4/5) | 1 mg/kg | 4 hr post-injection | 8 |

Additionally, in a second experiment with Bactericidal/Permeability Increasing Protein (BPI) neutropenic rats were challenged with Pseudomonas (PA1244) during a period of neutropenia. One group of rats was treated with 10 mg BPI/kg of body weight by intravenous administration at the onset of fever at day 5 and observed through day 11. A second group of rats was treated at the onset of fever with buffer containing saline at day 5 and observed until day 11. After day 8, the rat group treated with buffer was found dead; however, the rat group treated with BPI Protein exhibited 60% survival. The rats were observed for 11 days and the survival recorded for each group. At day 11, no additional deaths occurred for the rat group treated with BPI. The results of this experiment are shown in FIG. 15. FIG. 15 is a line graph showing that (1) during and after day 8 the rat group treated with buffer experienced a 100% mortality rate and (2) during and after day 7 the rat group treated with BPI Protein exhibited about a 40% mortality rate. The rats which received BPI Protein showed a significantly reduced mortality rate.

Human BPI Protein at does up to 10 mg/kg intravenously (IV) produced no acute hexatologic, biochemical, or pathologic abnormalities in outbred CD-1 mice or Sprague-Dawley rats (Table 5). Infusion of 1 mg/kg of *E. coli* 0111:B4 endotoxin IV in 6 CD-1 mice resulted in a 100% (6/6) survival rate in control CD-1 mice. The survival rate in BPI Protein treated mice infused with 1 mg/kg of *E. coli* 0111:B4 endotoxin IV at 1 mg/kg BPI Protein IV, 2 mg/kg BPI Protein IV, and 10 mg/kg BPI Protein IV was 100% (4/4), 100% (4/4) and 100 (5/5), respectively.

Infusion of 10 mg/kg of *E. coli* 0111:B4 endotoxin IV in 6 CD-1 mice resulted in a 17% (1/6) survival rate in control CD-1 mice. The survival rate in BPI Protein treated mice infused with 1 mg/kg of *E. coli* 0111:B4 endotoxin IV at 1 mg/kg BPI Protein IV, 2 mg/kg BPI Protein IV, and 10 mg/kg BPI Protein IV was 50% (2/4), 100% (4/4) and 100 (5/5), respectively.

TABLE 5

BPI PROTEIN PROTECTS AGAINST LETHALITY FROM ENDOTOXIC SHOCK (CD-1MICE)

| Endotoxin Challenge (*E. coli* 0111:B4) | % SURVIVAL (NO. SURVIVORS/TOTAL NO. ANIMALS TESTED | | | |
|---|---|---|---|---|
| | Control (Saline) | BPI 1 mg/kg IV | BPI 2 mg/kg IV | BPI 10 mg/kg IV |
| * 1 mg/kg IV | 100 (6/6) | 100 (4/4) | 100 (4/4) | 100 (5/5) |
| * 10 mg/kg IV | 17 (1/6) | 50 (2/4) | 100 (4/4) | 100 (5/5) |
| * 50 mg/kg IV | 0 (0/6) | 25 (2/40) | 25 (1/4) | 100 (5/5) |
| * 100 mg/kg IV | 0 (0/6) | 0 (0/4) | 0 (0/4) | 80 (4/5) |
| * 200 mg/kg IV | 0 (0/6) | 0 (0/4) | 0 (0/4) | 20 (1/5) |

Infusion of 50 mg/kg of *E. coli* 0111:B4 endotoxin IV in 6 CD-1 mice resulted in a 0% (0/6) survival rate in control CD-1 mice. The survival rate in BPI Protein treated mice infused with 1 mg/kg of *E. coli* 0111:B4 endotoxin IV at 1 mg/kg BPI Protein IV, 2 mg/kg BPI Protein IV, and 10 mg/kg BPI Protein IV was 25% (1/4), 25% (1/4) and 25 (5/5), respectively.

Infusion of 100 mg/kg of *E. coli* 0111:B4 endotoxin IV in 6 CD1mice resulted in a 0% (0/6) survival rate in control CD1mice. The survival rate in BPI Protein treated mice infused with 1 mg/kg of *E. coli* 0111:B4 endotoxin IV at 1 mg/kg BPI Protein IV, 2 mg/kg BPI Protein IV, and 10 mg/kg BPI Protein IV was 0% (0/4), 0% (0/4) and 80% (4/5), respectively.

Infusion of 200 mg/kg of *E. coli* 0111:B4 endotoxin IV in 6 CD1mice resulted in a 0% (0/6) survival rate in control CD1mice. The survival rate in BPI Protein treated mice infused with 1 mg/kg of *E. coli* 0111:B4 endotoxin IV at 1 mg/kg BPI Protein IV, 2 mg/kg BPI Protein IV, and 10 mg/kg BPI Protein IV was 0% (0/4), 0% (0/4) and 20% (1/5), respectively.

In conclusion, Table 5 demonstrates that BPI Protein is non-toxic in experimental animals and provides significant protection from lethality following endotoxin challenge (FIG. 16). This naturally occurring, neutrophil derived, antimicrobial protein provides a new therapeutic strategy in the treatment of septic-shock.

Human BPI Protein at does up to 10 mg/kg intravenously (IV) produced no acute hexatologic, biochemical, or pathologic abnormalities in outbred CD1mice (Table 6). Using CD-1 mice, the in vivo efficacy of BPI Protein against endotoxin was tested by infusing 50 mg/kg of *E. coli* 0111:B4 endotoxin IV in 10 mice resulted in a 100% (0/10) survival rate in control CD1mice. The survival rate for BPI Protein treated mice infused with 50 mg/kg of *E. coli* 0111:B4 endotoxin IV at 10 mg/kg BPI Protein IV was 0% (0/10). The p value is p<0.001. Further, 5 mice were infused with 50 mg/kg of 055 IV (as control) which resulted in a 0% (0/5) survival rate. The survival rate for BPI Protein treated mice infused with of 50 mg/kg 055 IV at 10 mg/kg BPI Protein IV was 100% (5/5). The p value is p<0.01. Additionally, 5 mice were infused with 25 mg/kg of Rc rough mutant (core glycolipid) IV (as control) which resulted in a 0% (0/5) survival rate. The survival rate for BPI Protein treated mice infused with 25 mg/kg of Rc rough mutant (core glycolipid)IV at 10 mg/kg BPI Protein IV was 100% (5/5). The p value is p<0.01. Also, 4 mice were infused with 25 mg/kg of Lipid A IV (as control) which resulted in a 0% (0/4) survival rate. The survival rate for BPI Protein treated mice infused with 25 mg/kg of Lipid A IV at 10 mg/kg BPI Protein IV was 100% (5/5). The p value is p<0.05.

BPI is a non-toxic naturally occurring protein with endotoxin neutralizing activity which reduces mortality in both endotoxic and bacteremic models of sepsis syndrome and may be a useful immunotherapeutic approach to the management of the septic shock.

TABLE 6

EFFECT OF BPI PROTEIN ON LETHALITY OF VARIOUS ENDOTOXIN PHENOTYPES

| endotoxin Phenotype | % Survival (No. Surviving/No. Animals Tested) | | |
|---|---|---|---|
| | BPI 10 mg/kg | Control | p Value |
| * 0111:B4 50 mg/kg | 100 (10/10) | 0 (1/10) | p < 0.001 |
| * 055 50 mg/kg | 100 (5/5) | 0 (0/5) | p = 0.01 |
| * Rc Rough mutant 25 mg/kg | 100 (5/5) | 0 (0/5) | p = 0.01 |
| * Lipid A 25 mg/kg | 100 (5/5) | 0 (0/4) | p < 0.05 |

In order to generate a non-glycosylated form of the BPI molecule, the (CHO) cell line which normally expresses glycosylated recombinant BPI Protein (clone 3A1), was grown to confluence in roller bottles (Costar, Cambridge, Mass.) in REM 020 (Hazelton, Inc. Denver, Pa.) containing 7.5% dialyzed bovine serum (Gibco)+2 μg/ml tunicamycin (Boehringer Mannheim, Indianapolis, Ind.). After 24 hours, the medium was discarded, and replaced with fresh complete medium containing 2 μ/ml tunicamycin. Conditioned medium was collected and replaced every 24 hours for three days. Non-glycosylated recombinant BPI Protein was purified as described in Example 3 above for recombinant BPI Protein and further separated from residual glycosylated recombinant BPI Protein by Superose 12 (Pharmacia) size exclusion chromatography in 20 mM glycine+100 mM NaCl at PH 2. Fractions containing nonglycosylated BPI Protein (identified by polyacrylamide gel electrophoresis) were pooled.

Glycosylated or nonglycosylated recombinant BPI Protein was injected into mice at 10 mg/kg. Blood was collected at the indicated times through the retroorbital plexus. Blood samples were then allowed to clot, the fibrin clot was removed by centrifugation, and the recombinant BPI Protein levels were determined by ELISA assay (results are shown in FIG. 18).

ELISA ASSAY

EQUIPMENT

Immulon-2 96 well plates (Dynatech) 12-channel 50–200 µl pipettor P20, P200, P1000 pipettors Reagent reservoirs (Costar) Racked 1 ml tubes (BioRad) polypropylene 15 ml conical tubes

REAGENTS

SOLUTIONS

25 Mm Borate pH 9.5

Blocking solution=5% BSA (Sigma Fraction V, Low Endotoxin) in PBS

| Wash/Sample Buffer: | 50 mM Tris pH 7.4 |
| --- | --- |
| | 500 mM NaCl |
| | 1 mg/ml BSA |
| | 0.05% Tween 20 |
| | 1 µ/ml Polymyxin B Sulfate |
| | (Gibco/BRL, 7900 U/mg) |

BPI standard (aliquots stored @-70° C.)

NOTE: BPI standards and samples should be diluted in polypropylene

Standard and sample diluent=appropriate solution for unknowns
  (e.g. if testing tissue culture supernatants, use REM+ 7.5% dFBS)

Substrate Buffer: (makes 500 ml)
  24.5 mg $MgCl_2$
  48 ml ethanolamine
  bring up to -400 ml with Lab V $H_2O$
  Adjust to pH 9.8
  Bring up to 500 ml with Lab V $H_2O$
PNPP substrate tablets (5 mg/tablet: Sigma)

ANTIBODIES

Capture (1st) Antibody (100 µl/well)
  A. INVN 1–2 (rabbit polyclonal anti-human BPI Protein) IgG 1 µg/ml, or,
  B. MM-1 (rabbit anti N-terminal 20 amino acid BPI peptide) 3 µg/ml.

Reporter (2nd) Antibody
  A. INVN 1–2-Biotin (Use @ 1:1000)
  B. PIG8 (murine monoclonal anti-BPI which blocks BPI binding to bacteria Third (developing) reagent
  A. Streptavidin/Alkaline Phosphatase (BioRad) (use @ 1:2000)
  B. Goat anti-mouse Ig/Alkaline Phosphatase conjugate (BioRad) (use @ 1:2000)

PROCEDURE

1. COATING PLATES
  Note: Coat plates up to 1 month in advance. Store plates at 4° C. until needed.
  Dilute capture antibody as directed in 25mM Na Borate pH 9.5 (10 ml/plate).
  Add 100 µl to each well of 96 well plate (Immulon-2). Incubate overnight at 37° C. Refrigerate until used.

2. BLOCKING
  Flick coating antibody out of plates. Add 200 µl 5% BSA in PBS to each well. Incubate 2–4 hours 37° C.

or overnight at 4° C. Wash 4X with wash solution and blot on paper towels.

3. BPI STANDARDS AND UNKNOWNS STANDARDS
  Thaw new standard aliquot (0.5 ml @ 1 mg/ml) every 2 months.
   1. Make 1ml stock solution of purified or BPI at 100 ng/ml
   2. Make 500 µl of each of the following standard concentrations as follows:

| µl 100 ng/ml BPI | µ diluent | final [BPI] ng/ml |
| --- | --- | --- |
| 150 | 350 | 30 |
| 100 | 400 | 20 |
| 75 | 425 | 15 |
| 50 | 450 | 10 |
| 40 | 460 | 8 |
| 25 | 475 | 5 |
| 10 | 490 | 2 |
| 0 | 50 | 0 |

Add 100 µl standard (unknown)/well and incubate at RT for 2–4 hours, or overnight at 4° C.
wash 4X 2nd ANTIBODY
After final wash, blot plate vigorously, and add 100 µl of INVN1–2-Biotinylated @ 1:1000 (=10 µl in 10 ml of wash/sample buffer) to each well.
Incubate 37° C. 1 hour
Wash 4X 3rd ANTIBODY
After final wash, blot plate vigorously, and add 100 µl developing reagent to each well.
Incubate 37° C. 30 minutes
Wash 4X SUBSTRATE
NOTE: Add substrate tablets to substrate buffer just before adding to plate.
After final wash, blot plate vigorously, and add 100 µl substrate solution (2X 5 mg PNPP substrate tablet/10 ml substrate buffer)
Read plate at 405 nm. Keep plate in the dark between readings.

EXAMPLE 5

Biologically Active Variants of BPI: Several classes of variants of BPI were constructed to alter some of the different properties of the native molecule(SEQ ID NOS:13 and 14). In the first type of construct, variants were designed to extend the molecular half-life in serum. In one of such constructs, the single glycosylation site at Ser351 was altered by making a single base pair change at position 1175 (FIG. 12) so that it encodes Ala and would not support N-glycosylation (i.e. Ser351->AlaBPI(nonglycosylated) (SEQ ID NO:18) at Table 7). This change was made by amplifying this particular segment of the molecule by PCR using amplimers containing the desired sequence, and then replacing the native segment with the corrected segment by virtue of convenient restriction sites (the SphI site at base 1202 in this case). Such a molecule was expected to possess similar properties as BPI but may be cleared less rapidly by the liver since it would lack the mannose residues recognized by hepatic clearance receptors. Other constructs were designed to take advantage of the apparent high stability of LBP, a homolog of BPI. For instance, the amino-terminal 25 kDa segment (presumably the endotoxin-binding domain) of LBP was combined with the carboxy-terminal 30 kDa portion of BPI to create a chimeric molecule with the greater serum half-life of LBP but the functionality of BPI (i.e. LBP25K/BPI30K chimeric (SEQ ID NO:17) at Table 7).

A third type of construct utilized the extraordinary serum stability of immunoglobin to extend the stability of BPI. The amino-terminal 25 kDa (LPS-binding) portion of BPI was linked to cDNA encoding the constant domain of IgG$_1$. The resultant chimeric molecule could be expected to bind endotoxin and inactivate it like the anti-endotoxin antibodies currently under development.

A second class of molecules were designed to enhance the therapeutic index of BPI Protein. For example, the amino terminal domain of BPI Protein contains a very high proportion of positively-charged residues (approximately 14%). In several of the variants, one or more of the amino terminal cationic residues were changed to neutral or negatively charged residues by the methods described below. Such redesigned molecules may prove less disruptive to biological membranes and therefore be less cationic. Also, the LBP/BPI Protein chimeric molecule described below (i.e. LBP25K/BP130K chimeric at Table 7) may also be less toxic due to the reduced cationicity of the LBP amino terminal domain relative to BPI.

A third class of variants were intended to increase the affinity, specificity, and/or valency of endotoxin binding to BPI. For example, recombinant BPI Protein containing single base pair changes within the 25 kDA portion were produced and tested for their ability to bind endotoxin in vitro. Changing certain key amino acids, particularly cationic residues, may enhance the affinity of BPI Protein for its ligand, i.e. endotoxin. Also, the LBP/BPI Protein chimeric molecule designated LBP25K/BPI30K chimeric may have the affinity of LPB for endotoxin, while possessing the functionality of BPI. Other constructs added a second endotoxin-binding domain to BPI, under the expectation that it may bind twice the amount of endotoxin per BPI Protein.

A fourth class of mutants were designed to modify the binding affinity of BPI and/or BPI/endotoxin complexes for the receptors with which it normally interacts to downregulate macrophage activation. Examples of this include BPI Protein with single amino acid changes within the 30 kDa portion of BPI, created by in vitro mutagenesis as described below. One such mutant designated BPI25K/DP/BPI30K (SEQ ID NO:19) (Table 7) created a variant from which the intact 25 kDA domain could be liberated by treatment with formic acid.

Methods used to create the biologically active variants of BPI were standard as practiced in the art. Relevant portions of key molecules were recombined to form chimeric molecules through commonly used methods. For example, the amino-terminal 25 kDa portion of LBP was linked to the carboxy-terminal portion of BPI Protein by virtue of an engineered ClaI site within the coding sequence (SEQ ID NO:27), as shown in FIG. 26. Oligonucleotide amplimers (SEQ ID NOS:20–25 and 27) containing cloning sites as well as a segment of DNA sufficient to hybridize to stretches at both ends of the target cDNA (25 bases) were synthesized chemically by standard methods. These primers were then used to amplify the desired gene segments by Polymerase Chain Reaction. The resulting new gene segments were digested with the corresponding restriction enzyme under standard conditions, and were isolated by gel electrophoresis. Alternately, similar gene segments were produced by digestion of the cDNA itself with appropriate restriction enzymes, and filling in missing gene segments with chemically synthesized oligonucleotides. These segments of coding sequence were ligated together and cloned into appropriate expression vectors which would allow recombinant production of the encoded sequence. Relevant expression systems for such chimeric molecules include but are not limited to mammalian cells such as CHO, fungi such as yeast, insect viruses such as baculavirus, and bacteria such as E. coli. For each of these systems, a useful expression vector would include antibiotic resistance gene such as ampicillin which would allow selection of recombinant clones; a second antibiotic resistance gene to allow selection on the host cells, such as neomycin; a bacterial replication origin to allow propagation in bacteria; a high level promoter upstream of the gene insertion site, such as the MMTV, SV40, or metallothionine promoter for CHO cells, the trp, lac, tac or T7 promoter for bacterial hosts, or the alpha factor, gal, or PGDH promoters in yeast; transcription enhancers for the mammalian hosts, such as the RSV enhancer; and a polyadenylation site, AATAAA, if one does not exist within the CDNA sequence. Once homogeneous cultures of recombinant cells were obtained through standard culture methods, large quantities of recombinant chimeric molecules were recovered and analyzed from the conditioned medium through standard chromatographic methods.

As examples, three of the constructs described above were constructed in vector pMamNeo, a commercially available expression vector (Clontech, Mountain View, Calif.), and used to transform mammalian cell host DUXB11. After transformation using lipofectin, a commercially available reagent (BRL/Gibco Gaithersberg, Md.), the cells were cultured in standard tissue culture medium to allow recovery and phenotypic expression of neomycin resistance. After 24 hours of recovery, the selective agent G418 was added to the medium to select for cells expressing the introduced genes. After three weeks of culture in selective media, drug resistant cell pools were obtained and grown to confluent densities. At this time, media was removed and assayed for the presence of immunoreactivity to anti-BPI Protein by ELISA, and for binding to endotoxin prebound to multiwell plates. In some cases, 160 nM dexamethasone was added to the medium to enhance expression because the vector also contained a glucocorticoid binding site in the promoter region. The levels of BPI Protein produced were monitored in each supernatant sample taken, and representative date is shown below:

TABLE 7

| Culture Description | ELISA ng/ml | Endotoxin Binding ng/ml |
| --- | --- | --- |
| A LBP25K/BP130K chimeric | 4.3 | 7.8 |
| B Ser182 -> AlaBPI (nonglycosylated) | 8.3 | 10.8 |
| C BP125K/DP/BPI30K | 5.8 | 5.2 |
| D BPI | 3.9 | 3.7 |

Therefore, these three biologically active variants of BPI were shown to be produced in CHO hosts, were immunologically crossreactive with anti-BPI Antibody, and able to bind endotoxin at levels similar to BPI. The same vector was transfected into alternate cell host lines to see of improved levels could be achieved. Constructs from which large quantities of recombinant protein was desired were also recloned into an amplifyable vector such as pSE, containing the gene encoding dihydrofolate reductase.

What is claimed is:

1. A biologically active recombinant variant of bactericidal/permeability increasing protein (BPI) as shown in FIG. 23 (SEQ ID NO:17).

2. A biologically active recombinant variant according to claim 1, wherein the variant (1) specifically binds to endotoxin, (2) competes with BPI Protein for binding to endotoxin, and (3) inhibits endotoxin-induced lethality.

* * * * *

SEQUENCE LISTING ( 1 ) GENERAL INFORMATION:

( i i i ) NUMBER OF SEQUENCES: 27

( 2 ) INFORMATION FOR SEQ ID NO:1:

( i ) SEQUENCE CHARACTERISTICS:
  ( A ) LENGTH: 8 amino acids
  ( B ) TYPE: amino acid
  ( C ) STRANDEDNESS: Not Relevant
  ( D ) TOPOLOGY: linear ( i i ) MOLECULE TYPE: protein ( x i ) SEQUENCE DESCRIPTION: SEQ ID NO:1:

Ile  Asn  Tyr  Gly  Leu  Val  Ala  Pro
 1                   5

( 2 ) INFORMATION FOR SEQ ID NO:2:

( i ) SEQUENCE CHARACTERISTICS:
  ( A ) LENGTH: 36 base pairs
  ( B ) TYPE: nucleic acid
  ( C ) STRANDEDNESS: single
  ( D ) TOPOLOGY: linear ( i i ) MOLECULE TYPE: DNA ( x i ) SEQUENCE DESCRIPTION: SEQ ID NO:2:

TAGAACTATG GTCTGGTGGC ACCTTGAGGA TCCGCG        36

( 2 ) INFORMATION FOR SEQ ID NO:3:

( i ) SEQUENCE CHARACTERISTICS:
  ( A ) LENGTH: 30 base pairs
  ( B ) TYPE: nucleic acid
  ( C ) STRANDEDNESS: single
  ( D ) TOPOLOGY: linear ( i i ) MOLECULE TYPE: DNA ( x i ) SEQUENCE DESCRIPTION: SEQ ID NO:3:

CGCGGATCCT CAAGGTGCCA CCAGACCATA        30

( 2 ) INFORMATION FOR SEQ ID NO:4:

( i ) SEQUENCE CHARACTERISTICS:
  ( A ) LENGTH: 30 base pairs
  ( B ) TYPE: nucleic acid
  ( C ) STRANDEDNESS: single
  ( D ) TOPOLOGY: linear ( i i ) MOLECULE TYPE: DNA ( x i ) SEQUENCE DESCRIPTION: SEQ ID NO:4:

CGCGGATCCT CAAGGTGCCA CCAGACCATA        30

( 2 ) INFORMATION FOR SEQ ID NO:5:

( i ) SEQUENCE CHARACTERISTICS:
  ( A ) LENGTH: 8 amino acids
  ( B ) TYPE: amino acid
  ( C ) STRANDEDNESS: Not Relevant
  ( D ) TOPOLOGY: linear ( i i ) MOLECULE TYPE: protein ( x i ) SEQUENCE DESCRIPTION: SEQ ID NO:5:

```
       Pro  Thr  Gly  Leu  Thr  Phe  Tyr  Pro
       1                   5
```

( 2 ) INFORMATION FOR SEQ ID NO:6:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:6:

```
CCCACCGGCC  TTACCTTCTA  CCCTTGAGGA  TCCGCG                                    36
```

( 2 ) INFORMATION FOR SEQ ID NO:7:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:7:

```
CGCGGATCCT  CAAGGGTAGA  AGGTAAGGCC                                            30
```

( 2 ) INFORMATION FOR SEQ ID NO:8:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:8:

```
CGCGGATCCT  CAAGGGTAGA  AGGTAAGGCC                                            30
```

( 2 ) INFORMATION FOR SEQ ID NO:9:

( i ) SEQUENCE CHARACTERISTICS:
        ( A ) LENGTH: 6 amino acids
        ( B ) TYPE: amino acid
        ( C ) STRANDEDNESS: Not Relevant
        ( D ) TOPOLOGY: linear ( i i ) MOLECULE TYPE: protein ( x i ) SEQUENCE DESCRIPTION: SEQ ID NO:9:

```
       Met  Arg  Glu  Asn  Met  Arg
       1                   5
```

( 2 ) INFORMATION FOR SEQ ID NO:10:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:10:

```
CCCAAGCTTG  CCACCATGAG  AGAGAACATG  GCC                                       33
```

( 2 ) INFORMATION FOR SEQ ID NO:11:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:11:

CCCAAGCTTG CCACCATGAG AGAGAACATG GCC     33

( 2 ) INFORMATION FOR SEQ ID NO:12:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:12:

AAAAAAACCC GAGATCCGCG GATCCTTTCC T     31

( 2 ) INFORMATION FOR SEQ ID NO:13:

( i ) SEQUENCE CHARACTERISTICS:
        ( A ) LENGTH: 487 amino acids
        ( B ) TYPE: amino acid
        ( D ) TOPOLOGY: linear ( i i ) MOLECULE TYPE: protein ( x i ) SEQUENCE DESCRIPTION: SEQ ID NO:13:

```
Met Arg Glu Asn Met Ala Arg Gly Pro Cys Asn Ala Pro Arg Trp Val
  1               5                  10                  15
Ser Leu Met Val Leu Val Ala Ile Gly Thr Ala Val Thr Ala Ala Val
             20                  25                  30
Asn Pro Gly Val Val Val Arg Ile Ser Gln Lys Gly Leu Asp Tyr Ala
         35                  40                  45
Ser Gln Gln Gly Thr Ala Ala Leu Gln Lys Glu Leu Lys Arg Ile Lys
 50                  55                  60
Ile Pro Asp Tyr Ser Asp Ser Phe Lys Ile Lys His Leu Gly Lys Gly
 65                  70                  75                  80
His Tyr Ser Phe Tyr Ser Met Asp Ile Arg Glu Phe Gln Leu Pro Ser
                 85                  90                  95
Ser Gln Ile Ser Met Val Pro Asn Val Gly Leu Lys Phe Ser Ile Ser
             100                 105                 110
Asn Ala Asn Ile Lys Ile Ser Gly Lys Trp Lys Ala Gln Lys Arg Phe
         115                 120                 125
Leu Lys Met Ser Gly Asn Phe Asp Leu Ser Ile Glu Gly Met Ser Ile
130                 135                 140
Ser Ala Asp Leu Lys Leu Gly Ser Asn Pro Thr Ser Gly Lys Pro Thr
145                 150                 155                 160
Ile Thr Cys Ser Ser Cys Ser Ser His Ile Asn Ser Val His Val His
                 165                 170                 175
Ile Ser Lys Ser Lys Val Gly Trp Leu Ile Gln Leu Phe His Lys Lys
             180                 185                 190
Ile Glu Ser Ala Leu Arg Asn Lys Met Asn Ser Gln Val Cys Glu Lys
         195                 200                 205
```

| Val | Thr | Asn | Ser | Val | Ser | Ser | Lys | Leu | Gln | Pro | Tyr | Phe | Gln | Thr | Leu |
|---|---|---|---|---|---|---|---|---|---|---|---|---|---|---|---|
| | 210 | | | | 215 | | | | | 220 | | | | | |

| Pro | Val | Met | Thr | Lys | Ile | Asp | Ser | Val | Ala | Gly | Ile | Asn | Tyr | Gly | Leu |
|---|---|---|---|---|---|---|---|---|---|---|---|---|---|---|---|
| 225 | | | | | 230 | | | | | 235 | | | | | 240 |

| Val | Ala | Pro | Pro | Ala | Thr | Thr | Ala | Glu | Thr | Leu | Asp | Val | Gln | Met | Lys |
|---|---|---|---|---|---|---|---|---|---|---|---|---|---|---|---|
| | | | | 245 | | | | | 250 | | | | | 255 | |

| Gly | Glu | Phe | Tyr | Ser | Glu | Asn | His | His | Asn | Pro | Pro | Pro | Phe | Ala | Pro |
|---|---|---|---|---|---|---|---|---|---|---|---|---|---|---|---|
| | | | 260 | | | | | 265 | | | | | 270 | | |

| Pro | Val | Met | Glu | Phe | Pro | Ala | Ala | His | Asp | Arg | Met | Val | Tyr | Leu | Gly |
|---|---|---|---|---|---|---|---|---|---|---|---|---|---|---|---|
| | | 275 | | | | | 280 | | | | | 285 | | | |

| Leu | Ser | Asp | Tyr | Phe | Phe | Asn | Thr | Ala | Gly | Leu | Val | Tyr | Gln | Glu | Ala |
|---|---|---|---|---|---|---|---|---|---|---|---|---|---|---|---|
| | 290 | | | | | 295 | | | | | 300 | | | | |

| Gly | Val | Leu | Lys | Met | Thr | Leu | Arg | Asp | Asp | Met | Ile | Pro | Lys | Glu | Ser |
|---|---|---|---|---|---|---|---|---|---|---|---|---|---|---|---|
| 305 | | | | | 310 | | | | | 315 | | | | | 320 |

| Lys | Phe | Arg | Leu | Thr | Thr | Lys | Phe | Phe | Gly | Thr | Phe | Leu | Pro | Glu | Val |
|---|---|---|---|---|---|---|---|---|---|---|---|---|---|---|---|
| | | | | 325 | | | | | 330 | | | | | 335 | |

| Ala | Lys | Lys | Phe | Pro | Asn | Met | Lys | Ile | Gln | Ile | His | Val | Ser | Ala | Ser |
|---|---|---|---|---|---|---|---|---|---|---|---|---|---|---|---|
| | | | 340 | | | | | 345 | | | | | 350 | | |

| Thr | Pro | Pro | His | Leu | Ser | Val | Gln | Pro | Thr | Gly | Leu | Thr | Phe | Tyr | Pro |
|---|---|---|---|---|---|---|---|---|---|---|---|---|---|---|---|
| | | 355 | | | | | 360 | | | | | 365 | | | |

| Ala | Val | Asp | Val | Gln | Ala | Phe | Ala | Val | Leu | Pro | Asn | Ser | Ser | Leu | Ala |
|---|---|---|---|---|---|---|---|---|---|---|---|---|---|---|---|
| | 370 | | | | | 375 | | | | | 380 | | | | |

| Ser | Leu | Phe | Leu | Ile | Gly | Met | His | Thr | Thr | Gly | Ser | Met | Glu | Val | Ser |
|---|---|---|---|---|---|---|---|---|---|---|---|---|---|---|---|
| 385 | | | | | 390 | | | | | 395 | | | | | 400 |

| Ala | Glu | Ser | Asn | Arg | Leu | Val | Gly | Glu | Leu | Lys | Leu | Asp | Arg | Leu | Leu |
|---|---|---|---|---|---|---|---|---|---|---|---|---|---|---|---|
| | | | | 405 | | | | | 410 | | | | | 415 | |

| Leu | Glu | Leu | Lys | His | Ser | Asn | Ile | Gly | Pro | Phe | Pro | Val | Glu | Leu | Leu |
|---|---|---|---|---|---|---|---|---|---|---|---|---|---|---|---|
| | | | 420 | | | | | 425 | | | | | 430 | | |

| Gln | Asp | Ile | Met | Asn | Tyr | Ile | Val | Pro | Ile | Leu | Val | Leu | Pro | Arg | Val |
|---|---|---|---|---|---|---|---|---|---|---|---|---|---|---|---|
| | | 435 | | | | | 440 | | | | | 445 | | | |

| Asn | Glu | Lys | Leu | Gln | Lys | Gly | Phe | Pro | Leu | Pro | Thr | Pro | Ala | Arg | Val |
|---|---|---|---|---|---|---|---|---|---|---|---|---|---|---|---|
| | 450 | | | | | 455 | | | | | 460 | | | | |

| Gln | Leu | Tyr | Asn | Val | Val | Leu | Gln | Pro | His | Gln | Asn | Phe | Leu | Leu | Phe |
|---|---|---|---|---|---|---|---|---|---|---|---|---|---|---|---|
| 465 | | | | | 470 | | | | | 475 | | | | | 480 |

| Gly | Ala | Asp | Val | Val | Tyr | Lys |
|---|---|---|---|---|---|---|
| | | | | 485 | | |

( 2 ) INFORMATION FOR SEQ ID NO:14:

( i ) SEQUENCE CHARACTERISTICS:
        ( A ) LENGTH: 1813 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:14:

```
CAGGCCTTGA  GGTTTTGGCA  GCTCTGGAGG  ATGAGAGAGA  ACATGGCCAG  GGGCCCTTGC      60

AACGCGCCGA  GATGGGTGTC  CCTGATGGTG  CTCGTCGCCA  TAGGCACCGC  CGTGACAGCG     120

GCCGTCAACC  TGGCGTCGT   GGTCAGGATC  TCCCAGAAGG  GCCTGGACTA  CGCCAGCAG      180

CAGGGGACGG  CCGCTCTGCA  GAAGGAGCTG  AAGAGGATCA  AGATTCCTGA  CTACTCAGAC     240

AGCTTTAAGA  TCAAGCATCT  TGGGAAGGGG  CATTATAGCT  TCTACAGCAT  GGACATCCGT     300

GAATTCCAGC  TTCCCAGTTC  CCAGATAAGC  ATGGTGCCCA  ATGTGGGCCT  TAAGTTCTCC     360
```

| | | | | | |
|---|---|---|---|---|---|
| ATCAGCAACG | CCAATATCAA | GATCAGCGGG | AAATGGAAGG | CACAAAAGAG | ATTCTTAAAA | 420 |
| ATGAGCGGCA | ATTTTGACCT | GAGCATAGAA | GGCATGTCCA | TTTCGGCTGA | TCTGAAGCTG | 480 |
| GGCAGTAACC | CCACGTCAGG | CAAGCCCACC | ATCACCTGCT | CCAGCTGCAG | CAGCCACATC | 540 |
| AACAGTGTCC | ACGTGCACAT | CTCAAAGAGC | AAAGTCGGGT | GGCTGATCCA | ACTCTTCCAC | 600 |
| AAAAAAATTG | AGTCTGCGCT | TCGAAACAAG | ATGAACAGCC | AGGTCTGCGA | GAAAGTGACC | 660 |
| AATTCTGTAT | CCTCCAAGCT | GCAACCTTAT | TTCCAGACTC | TGCCAGTAAT | GACCAAAATA | 720 |
| GATTCTGTGG | CTGGAATCAA | CTATGGTCTG | GTGGCACCTC | CAGCAACCAC | GGCTGAGACC | 780 |
| CTGGATGTAC | AGATGAAGGG | GGAGTTTTAC | AGTGAGAACC | ACCACAATCC | ACCTCCCTTT | 840 |
| GCTCCACCAG | TGATGGAGTT | TCCCGCTGCC | CATGACCGCA | TGGTATACCT | GGGCCTCTCA | 900 |
| GACTACTTCT | TCAACACAGC | CGGGCTTGTA | TACCAAGAGG | CTGGGGTCTT | GAAGATGACC | 960 |
| CTTAGAGATG | ACATGATTCC | AAAGGAGTCC | AAATTTCGAC | TGACAACCAA | GTTCTTTGGA | 1020 |
| ACCTTCCTAC | CTGAGGTGGC | CAAGAAGTTT | CCCAACATGA | AGATACAGAT | CCATGTCTCA | 1080 |
| GCCTCCACCC | CGCCACACCT | GTCTGTGCAG | CCCACCGGCC | TTACCTTCTA | CCCTGCCGTG | 1140 |
| GATGTCCAGG | CCTTTGCCGT | CCTCCCCAAC | TCCTCCCTGG | CTTCCTCTT | CCTGATTGGC | 1200 |
| ATGCACACAA | CTGGTTCCAT | GGAGGTCAGC | GCCGAGTCCA | ACAGGCTTGT | TGGAGAGCTC | 1260 |
| AAGCTGGATA | GGCTGCTCCT | GGAACTGAAG | CACTCAAATA | TTGGCCCCTT | CCCGGTTGAA | 1320 |
| TTGCTGCAGG | ATATCATGAA | CTACATTGTA | CCCATTCTTG | TGCTGCCCAG | GGTTAACGAG | 1380 |
| AAACTACAGA | AAGGCTTCCC | TCTCCCGACG | CCGGCCAGAG | TCCAGCTCTA | CAACGTAGTG | 1440 |
| CTTCAGCCTC | ACCAGAACTT | CCTGCTGTTC | GGTGCAGACG | TTGTCTATAA | ATGAAGGCAC | 1500 |
| CAGGGGTGCC | GGGGGCTGTC | AGCCGCACCT | GTTCCTGATG | GGCTGTGGGG | CACCGGCTGC | 1560 |
| CTTTCCCCAG | GGAATCCTCT | CCAGATCTTA | ACCAAGAGCC | CCTTGCAAAC | TTCTTCGACT | 1620 |
| CAGATTCAGA | AATGATCTAA | ACACGAGGAA | ACATTATTCA | TTGGAAAAGT | GCATGGTGTG | 1680 |
| TATTTTAGGG | ATTATGAGCT | TCTTTCAAGG | GCTAAGGCTG | CAGAGATATT | TCCTCCAGGA | 1740 |
| ATCGTGTTTC | AATTGTAACC | AAGAAATTTC | CATTTGTGCT | TCATGAAAAA | AAACTTCTGG | 1800 |
| TTTTTTTCAT | GTG | | | | | 1813 |

( 2 ) INFORMATION FOR SEQ ID NO:15:

( i ) SEQUENCE CHARACTERISTICS:
        ( A ) LENGTH: 368 amino acids
        ( B ) TYPE: amino acid
        ( C ) STRANDEDNESS: Not Relevant
        ( D ) TOPOLOGY: linear ( i i ) MOLECULE TYPE: protein ( x i ) SEQUENCE DESCRIPTION: SEQ ID NO:15:

```
Met Arg Glu Asn Met Ala Arg Gly Pro Cys Asn Ala Pro Arg Trp Val
 1               5                  10                  15

Ser Leu Met Val Leu Val Ala Ile Gly Thr Ala Val Thr Ala Ala Val
                20                  25                  30

Asn Pro Gly Val Val Val Arg Ile Ser Gln Lys Gly Leu Asp Tyr Ala
                35                  40                  45

Ser Gln Gln Gly Thr Ala Ala Leu Gln Lys Glu Leu Lys Arg Ile Lys
        50                  55                  60

Ile Pro Asp Tyr Ser Asp Ser Phe Lys Ile Lys His Leu Gly Lys Gly
65                  70                  75                  80

His Tyr Ser Phe Tyr Ser Met Asp Ile Arg Glu Phe Gln Leu Pro Ser
                85                  90                  95
```

```
Ser  Gln  Ile  Ser  Met  Val  Pro  Asn  Val  Gly  Leu  Lys  Phe  Ser  Ile  Ser
               100                      105                      110

Asn  Ala  Asn  Ile  Lys  Ile  Ser  Gly  Lys  Trp  Lys  Ala  Gln  Lys  Arg  Phe
          115                      120                      125

Leu  Lys  Met  Ser  Gly  Asn  Phe  Asp  Leu  Ser  Ile  Glu  Gly  Met  Ser  Ile
     130                      135                      140

Ser  Ala  Asp  Leu  Lys  Leu  Gly  Ser  Asn  Pro  Thr  Ser  Gly  Lys  Pro  Thr
145                           150                      155                      160

Ile  Thr  Cys  Ser  Ser  Cys  Ser  Ser  His  Ile  Asn  Ser  Val  His  Val  His
                    165                      170                      175

Ile  Ser  Lys  Ser  Lys  Val  Gly  Trp  Leu  Ile  Gln  Leu  Phe  His  Lys  Lys
                    180                      185                      190

Ile  Glu  Ser  Ala  Leu  Arg  Asn  Lys  Met  Asn  Ser  Gln  Val  Cys  Glu  Lys
               195                      200                      205

Val  Thr  Asn  Ser  Val  Ser  Ser  Lys  Leu  Gln  Pro  Tyr  Phe  Gln  Thr  Leu
     210                      215                      220

Pro  Val  Met  Thr  Lys  Ile  Asp  Ser  Val  Ala  Gly  Ile  Asn  Tyr  Gly  Leu
225                      230                      235                           240

Val  Ala  Pro  Pro  Ala  Thr  Thr  Ala  Glu  Thr  Leu  Asp  Val  Gln  Met  Lys
               245                      250                      255

Gly  Glu  Phe  Tyr  Ser  Glu  Asn  His  His  Asn  Pro  Pro  Pro  Phe  Ala  Pro
               260                      265                      270

Pro  Val  Met  Glu  Phe  Pro  Ala  Ala  His  Asp  Arg  Met  Val  Tyr  Leu  Gly
          275                      280                      285

Leu  Ser  Asp  Tyr  Phe  Phe  Asn  Thr  Ala  Gly  Leu  Val  Tyr  Gln  Glu  Ala
     290                      295                      300

Gly  Val  Leu  Lys  Met  Thr  Leu  Arg  Asp  Asp  Met  Ile  Pro  Lys  Glu  Ser
305                      310                      315                           320

Lys  Phe  Arg  Leu  Thr  Thr  Lys  Phe  Phe  Gly  Thr  Phe  Leu  Pro  Glu  Val
                    325                      330                      335

Ala  Lys  Lys  Phe  Pro  Asn  Met  Lys  Ile  Gln  Ile  His  Val  Ser  Ala  Ser
                    340                      345                      350

Thr  Pro  Pro  His  Leu  Ser  Val  Gln  Pro  Thr  Gly  Leu  Thr  Phe  Tyr  Pro
          355                      360                      365
```

( 2 ) INFORMATION FOR SEQ ID NO:16:

( i ) SEQUENCE CHARACTERISTICS:
        ( A ) LENGTH: 243 amino acids
        ( B ) TYPE: amino acid
        ( C ) STRANDEDNESS: Not Relevant
        ( D ) TOPOLOGY: linear ( i i ) MOLECULE TYPE: protein ( x i ) SEQUENCE DESCRIPTION: SEQ ID NO:16:

```
Met  Arg  Glu  Asn  Met  Ala  Arg  Gly  Pro  Cys  Asn  Ala  Pro  Arg  Trp  Val
1                   5                        10                      15

Ser  Leu  Met  Val  Leu  Val  Ala  Ile  Gly  Thr  Ala  Val  Thr  Ala  Ala  Val
          20                       25                       30

Asn  Pro  Gly  Val  Val  Val  Arg  Ile  Ser  Gln  Lys  Gly  Leu  Asp  Tyr  Ala
          35                       40                       45

Ser  Gln  Gln  Gly  Thr  Ala  Ala  Leu  Gln  Lys  Glu  Leu  Lys  Arg  Ile  Lys
     50                       55                       60

Ile  Pro  Asp  Tyr  Ser  Asp  Ser  Phe  Lys  Ile  Lys  His  Leu  Gly  Lys  Gly
65                       70                       75                            80
```

```
His  Tyr  Ser  Phe  Tyr  Ser  Met  Asp  Ile  Arg  Glu  Phe  Gln  Leu  Pro  Ser
                    85                  90                       95

Ser  Gln  Ile  Ser  Met  Val  Pro  Asn  Val  Gly  Leu  Lys  Phe  Ser  Ile  Ser
               100                 105                      110

Asn  Ala  Asn  Ile  Lys  Ile  Ser  Gly  Lys  Trp  Lys  Ala  Gln  Lys  Arg  Phe
          115                      120                 125

Leu  Lys  Met  Ser  Gly  Asn  Phe  Asp  Leu  Ser  Ile  Glu  Gly  Met  Ser  Ile
     130                      135                 140

Ser  Ala  Asp  Leu  Lys  Leu  Gly  Ser  Asn  Pro  Thr  Ser  Gly  Lys  Pro  Thr
145                      150                      155                      160

Ile  Thr  Cys  Ser  Ser  Cys  Ser  Ser  His  Ile  Asn  Ser  Val  His  Val  His
                    165                      170                      175

Ile  Ser  Lys  Ser  Lys  Val  Gly  Trp  Leu  Ile  Gln  Leu  Phe  His  Lys  Lys
               180                      185                      190

Ile  Glu  Ser  Ala  Leu  Arg  Asn  Lys  Met  Asn  Ser  Gln  Val  Cys  Glu  Lys
          195                      200                      205

Val  Thr  Asn  Ser  Val  Ser  Ser  Lys  Leu  Gln  Pro  Tyr  Phe  Gln  Thr  Leu
     210                      215                      220

Pro  Val  Met  Thr  Lys  Ile  Asp  Ser  Val  Ala  Gly  Ile  Asn  Tyr  Gly  Leu
225                      230                      235                      240

Val  Ala  Pro
```

(2) INFORMATION FOR SEQ ID NO:17:

(i) SEQUENCE CHARACTERISTICS:
        (A) LENGTH: 454 amino acids
        (B) TYPE: amino acid
        (C) STRANDEDNESS: Not Relevant
        (D) TOPOLOGY: linear (ii) MOLECULE TYPE: protein (xi) SEQUENCE DESCRIPTION: SEQ ID NO:17:

```
Ala  Asn  Pro  Gly  Leu  Val  Ala  Arg  Ile  Thr  Asp  Lys  Gly  Leu  Gln  Tyr
1               5                   10                      15

Ala  Ala  Gln  Glu  Gly  Leu  Leu  Ala  Leu  Gln  Ser  Glu  Leu  Leu  Arg  Ile
               20                  25                       30

Thr  Leu  Pro  Asp  Phe  Thr  Gly  Asp  Leu  Arg  Ile  Pro  His  Val  Gly  Arg
               35                  40                       45

Gly  Arg  Tyr  Glu  Phe  His  Ser  Leu  Asn  Ile  His  Ser  Cys  Glu  Leu  Leu
     50                       55                  60

His  Ser  Ala  Leu  Arg  Pro  Val  Pro  Gly  Gln  Gly  Leu  Ser  Leu  Ser  Ile
65                       70                  75                            80

Ser  Asp  Ser  Ser  Ile  Arg  Val  Gln  Gly  Arg  Trp  Lys  Val  Arg  Lys  Ser
                    85                  90                       95

Phe  Phe  Lys  Leu  Gln  Gly  Ser  Phe  Asp  Val  Ser  Val  Lys  Gly  Ile  Ser
               100                      105                      110

Ile  Ser  Val  Asn  Leu  Leu  Leu  Gly  Ser  Glu  Ser  Ser  Gly  Arg  Pro  Thr
          115                      120                      125

Gly  Tyr  Cys  Leu  Ser  Cys  Ser  Ser  Asp  Ile  Ala  Asp  Val  Glu  Val  Asp
     130                      135                      140

Met  Ser  Gly  Asp  Ser  Gly  Trp  Leu  Leu  Asn  Leu  Phe  His  Asn  Gln  Ile
145                      150                      155                      160

Glu  Ser  Lys  Phe  Gln  Lys  Val  Leu  Glu  Ser  Arg  Ile  Cys  Glu  Met  Ile
               165                      170                      175

Gln  Lys  Ser  Val  Ser  Ser  Asp  Leu  Gln  Pro  Tyr  Leu  Gln  Thr  Leu  Pro
          180                      185                      190
```

```
Val  Thr  Thr  Glu  Ile  Asp  Ser  Val  Ala  Gly  Ile  Asn  Tyr  Gly  Leu  Val
          195                      200                      205

Ala  Pro  Pro  Ala  Thr  Thr  Ala  Glu  Thr  Leu  Asp  Val  Gln  Met  Lys  Gly
          210                      215                      220

Glu  Phe  Tyr  Ser  Glu  Asn  His  His  Asn  Pro  Pro  Phe  Ala  Pro  Pro
225                           230                 235                      240

Val  Met  Glu  Phe  Pro  Ala  Ala  His  Asp  Arg  Met  Val  Tyr  Leu  Gly  Leu
                    245                      250                 255

Ser  Asp  Tyr  Phe  Phe  Asn  Thr  Ala  Gly  Leu  Val  Tyr  Gln  Glu  Ala  Gly
                    260                 265                      270

Val  Leu  Lys  Met  Thr  Leu  Arg  Asp  Asp  Met  Ile  Pro  Lys  Glu  Ser  Lys
               275                 280                      285

Phe  Arg  Leu  Thr  Thr  Lys  Phe  Phe  Gly  Thr  Phe  Leu  Pro  Glu  Val  Ala
          290                      295                 300

Lys  Lys  Phe  Pro  Asn  Met  Lys  Ile  Gln  Ile  His  Val  Ser  Ala  Ser  Thr
305                           310                 315                      320

Pro  Pro  His  Leu  Ser  Val  Gln  Pro  Thr  Gly  Leu  Thr  Phe  Tyr  Pro  Ala
                    325                      330                 335

Val  Asp  Val  Gln  Ala  Phe  Ala  Val  Leu  Pro  Asn  Ser  Ser  Leu  Ala  Ser
                    340                      345                 350

Leu  Phe  Leu  Ile  Gly  Met  His  Thr  Thr  Gly  Ser  Met  Glu  Val  Ser  Ala
               355                 360                      365

Glu  Ser  Asn  Arg  Leu  Val  Gly  Glu  Leu  Lys  Leu  Asp  Arg  Leu  Leu  Leu
          370                      375                 380

Glu  Leu  Lys  His  Ser  Asn  Ile  Gly  Pro  Phe  Pro  Val  Glu  Leu  Leu  Gln
385                      390                      395                      400

Asp  Ile  Met  Asn  Tyr  Ile  Val  Pro  Ile  Leu  Val  Leu  Pro  Arg  Val  Asn
                    405                      410                      415

Glu  Lys  Leu  Gln  Lys  Gly  Phe  Pro  Leu  Pro  Thr  Pro  Ala  Arg  Val  Gln
                    420                      425                 430

Leu  Tyr  Asn  Val  Val  Leu  Gln  Pro  His  Gln  Asn  Phe  Leu  Leu  Phe  Gly
               435                 440                      445

Ala  Asp  Val  Val  Tyr  Lys
          450
```

( 2 ) INFORMATION FOR SEQ ID NO:18:

( i ) SEQUENCE CHARACTERISTICS:
        ( A ) LENGTH: 456 amino acids
        ( B ) TYPE: amino acid
        ( C ) STRANDEDNESS: Not Relevant
        ( D ) TOPOLOGY: linear ( i i ) MOLECULE TYPE: protein ( x i ) SEQUENCE DESCRIPTION: SEQ ID NO:18:

```
Val  Asn  Pro  Gly  Val  Val  Arg  Ile  Ser  Gln  Lys  Gly  Leu  Asp  Tyr
1                   5                      10                      15

Ala  Ser  Gln  Gln  Gly  Thr  Ala  Ala  Leu  Gln  Lys  Glu  Leu  Lys  Arg  Ile
               20                      25                      30

Lys  Ile  Pro  Asp  Tyr  Ser  Asp  Ser  Phe  Lys  Ile  Lys  His  Leu  Gly  Lys
          35                      40                      45

Gly  His  Tyr  Ser  Phe  Tyr  Ser  Met  Asp  Ile  Arg  Glu  Phe  Gln  Leu  Pro
     50                      55                      60

Ser  Ser  Gln  Ile  Ser  Met  Val  Pro  Asn  Val  Gly  Leu  Lys  Phe  Ser  Ile
65                       70                      75                       80
```

-continued

```
Ser  Asn  Ala  Asn  Ile  Lys  Ile  Ser  Gly  Lys  Trp  Lys  Ala  Gln  Lys  Arg
               85                  90                       95
Phe  Leu  Lys  Met  Ser  Gly  Asn  Phe  Asp  Leu  Ser  Ile  Glu  Gly  Met  Ser
         100                      105                      110
Ile  Ser  Ala  Asp  Leu  Lys  Leu  Gly  Ser  Asn  Pro  Thr  Ser  Gly  Lys  Pro
         115                      120                      125
Thr  Ile  Thr  Cys  Ser  Ser  Cys  Ser  Ser  His  Ile  Asn  Ser  Val  His  Val
    130                      135                      140
His  Ile  Ser  Lys  Ser  Lys  Val  Gly  Trp  Leu  Ile  Gln  Leu  Phe  His  Lys
145                      150                      155                      160
Lys  Ile  Glu  Ser  Ala  Leu  Arg  Asn  Lys  Met  Asn  Ser  Gln  Val  Cys  Glu
                   165                 170                      175
Lys  Val  Thr  Asn  Ser  Val  Ser  Ser  Lys  Leu  Gln  Pro  Tyr  Phe  Gln  Thr
              180                      185                      190
Leu  Pro  Val  Met  Thr  Lys  Ile  Asp  Ser  Val  Ala  Gly  Ile  Asn  Tyr  Gly
              195                      200                 205
Leu  Val  Ala  Pro  Pro  Ala  Thr  Thr  Ala  Glu  Thr  Leu  Asp  Val  Gln  Met
         210                      215                 220
Lys  Gly  Glu  Phe  Tyr  Ser  Glu  Asn  His  His  Asn  Pro  Pro  Phe  Ala
225                           230                 235                      240
Pro  Pro  Val  Met  Glu  Phe  Pro  Ala  Ala  His  Asp  Arg  Met  Val  Tyr  Leu
                   245                      250                      255
Gly  Leu  Ser  Asp  Tyr  Phe  Phe  Asn  Thr  Ala  Gly  Leu  Val  Tyr  Gln  Glu
              260                      265                      270
Ala  Gly  Val  Leu  Lys  Met  Thr  Leu  Arg  Asp  Asp  Met  Ile  Pro  Lys  Glu
              275                      280                 285
Ser  Lys  Phe  Arg  Leu  Thr  Thr  Lys  Phe  Phe  Gly  Thr  Phe  Leu  Pro  Glu
     290                      295                      300
Val  Ala  Lys  Lys  Phe  Pro  Asn  Met  Lys  Ile  Gln  Ile  His  Val  Ser  Ala
305                           310                 315                      320
Ser  Thr  Pro  Pro  His  Leu  Ser  Val  Gln  Pro  Thr  Gly  Leu  Thr  Phe  Tyr
                   325                      330                      335
Pro  Ala  Val  Asp  Val  Gln  Ala  Phe  Ala  Val  Leu  Pro  Asn  Ser  Ala  Leu
              340                      345                 350
Ala  Ser  Leu  Phe  Leu  Ile  Gly  Met  His  Thr  Thr  Gly  Ser  Met  Glu  Val
         355                      360                 365
Ser  Ala  Glu  Ser  Asn  Arg  Leu  Val  Gly  Glu  Leu  Lys  Leu  Asp  Arg  Leu
    370                      375                 380
Leu  Leu  Glu  Leu  Lys  His  Ser  Asn  Ile  Gly  Pro  Phe  Pro  Val  Glu  Leu
385                      390                      395                      400
Leu  Gln  Asp  Ile  Met  Asn  Tyr  Ile  Val  Pro  Ile  Leu  Val  Leu  Pro  Arg
              405                      410                      415
Val  Asn  Glu  Lys  Leu  Gln  Lys  Gly  Phe  Pro  Leu  Pro  Thr  Pro  Ala  Arg
              420                      425                      430
Val  Gln  Leu  Tyr  Asn  Val  Val  Leu  Gln  Pro  His  Gln  Asn  Phe  Leu  Leu
         435                      440                 445
Phe  Gly  Ala  Asp  Val  Val  Tyr  Lys
    450                      455
```

( 2 ) INFORMATION FOR SEQ ID NO:19:

( i ) SEQUENCE CHARACTERISTICS:
        ( A ) LENGTH: 456 amino acids
        ( B ) TYPE: amino acid
        ( C ) STRANDEDNESS: Not Relevant
        ( D ) TOPOLOGY: linear ( i i ) MOLECULE TYPE: protein ( x i ) SEQUENCE DESCRIPTION: SEQ ID NO:19:

| Val | Asn | Pro | Gly | Val | Val | Arg | Ile | Ser | Gln | Lys | Gly | Leu | Asp | Tyr |
|-----|-----|-----|-----|-----|-----|-----|-----|-----|-----|-----|-----|-----|-----|-----|
| 1   |     |     |     | 5   |     |     |     |     | 10  |     |     |     |     | 15  |
| Ala | Ser | Gln | Gln | Gly | Thr | Ala | Ala | Leu | Gln | Lys | Glu | Leu | Lys | Arg | Ile |
|     |     |     | 20  |     |     |     |     | 25  |     |     |     |     | 30  |     |     |
| Lys | Ile | Pro | Asp | Tyr | Ser | Asp | Ser | Phe | Lys | Ile | Lys | His | Leu | Gly | Lys |
|     |     | 35  |     |     |     |     | 40  |     |     |     |     | 45  |     |     |     |
| Gly | His | Tyr | Ser | Phe | Tyr | Ser | Met | Asp | Ile | Arg | Glu | Phe | Gln | Leu | Pro |
|     | 50  |     |     |     |     | 55  |     |     |     |     | 60  |     |     |     |     |
| Ser | Ser | Gln | Ile | Ser | Met | Val | Pro | Asn | Val | Gly | Leu | Lys | Phe | Ser | Ile |
| 65  |     |     |     |     | 70  |     |     |     |     | 75  |     |     |     |     | 80  |
| Ser | Asn | Ala | Asn | Ile | Lys | Ile | Ser | Gly | Lys | Trp | Lys | Ala | Gln | Lys | Arg |
|     |     |     |     | 85  |     |     |     |     | 90  |     |     |     |     | 95  |     |
| Phe | Leu | Lys | Met | Ser | Gly | Asn | Phe | Asp | Leu | Ser | Ile | Glu | Gly | Met | Ser |
|     |     |     | 100 |     |     |     |     | 105 |     |     |     |     | 110 |     |     |
| Ile | Ser | Ala | Asp | Leu | Lys | Leu | Gly | Ser | Asn | Pro | Thr | Ser | Gly | Lys | Pro |
|     |     | 115 |     |     |     |     | 120 |     |     |     |     | 125 |     |     |     |
| Thr | Ile | Thr | Cys | Ser | Ser | Cys | Ser | Ser | His | Ile | Asn | Ser | Val | His | Val |
|     | 130 |     |     |     |     | 135 |     |     |     |     | 140 |     |     |     |     |
| His | Ile | Ser | Lys | Ser | Lys | Val | Gly | Trp | Leu | Ile | Gln | Leu | Phe | His | Lys |
| 145 |     |     |     |     | 150 |     |     |     |     | 155 |     |     |     |     | 160 |
| Lys | Ile | Glu | Ser | Ala | Leu | Arg | Asn | Lys | Met | Asn | Ser | Gln | Val | Cys | Glu |
|     |     |     |     | 165 |     |     |     |     | 170 |     |     |     |     | 175 |     |
| Lys | Val | Thr | Asn | Ser | Val | Ser | Ser | Lys | Leu | Gln | Pro | Tyr | Phe | Gln | Thr |
|     |     |     | 180 |     |     |     |     | 185 |     |     |     |     | 190 |     |     |
| Leu | Pro | Val | Met | Thr | Lys | Ile | Asp | Pro | Val | Ala | Gly | Ile | Asn | Tyr | Gly |
|     |     | 195 |     |     |     |     | 200 |     |     |     |     | 205 |     |     |     |
| Leu | Val | Ala | Pro | Pro | Ala | Thr | Thr | Ala | Glu | Thr | Leu | Asp | Val | Gln | Met |
|     | 210 |     |     |     |     | 215 |     |     |     |     | 220 |     |     |     |     |
| Lys | Gly | Glu | Phe | Tyr | Ser | Glu | Asn | His | His | Asn | Pro | Pro | Phe | Ala |
| 225 |     |     |     |     | 230 |     |     |     |     | 235 |     |     |     |     | 240 |
| Pro | Pro | Val | Met | Glu | Phe | Pro | Ala | Ala | His | Asp | Arg | Met | Val | Tyr | Leu |
|     |     |     |     | 245 |     |     |     |     | 250 |     |     |     |     | 255 |     |
| Gly | Leu | Ser | Asp | Tyr | Phe | Phe | Asn | Thr | Ala | Gly | Leu | Val | Tyr | Gln | Glu |
|     |     |     | 260 |     |     |     |     | 265 |     |     |     |     | 270 |     |     |
| Ala | Gly | Val | Leu | Lys | Met | Thr | Leu | Arg | Asp | Asp | Met | Ile | Pro | Lys | Glu |
|     |     | 275 |     |     |     |     | 280 |     |     |     |     | 285 |     |     |     |
| Ser | Lys | Phe | Arg | Leu | Thr | Thr | Lys | Phe | Phe | Gly | Thr | Phe | Leu | Pro | Glu |
|     | 290 |     |     |     |     | 295 |     |     |     |     | 300 |     |     |     |     |
| Val | Ala | Lys | Lys | Phe | Pro | Asn | Met | Lys | Ile | Gln | Ile | His | Val | Ser | Ala |
| 305 |     |     |     |     | 310 |     |     |     |     | 315 |     |     |     |     | 320 |
| Ser | Thr | Pro | Pro | His | Leu | Ser | Val | Gln | Pro | Thr | Gly | Leu | Thr | Phe | Tyr |
|     |     |     |     | 325 |     |     |     |     | 330 |     |     |     |     | 335 |     |
| Pro | Ala | Val | Asp | Val | Gln | Ala | Phe | Ala | Val | Leu | Pro | Asn | Ser | Ser | Leu |
|     |     |     | 340 |     |     |     |     | 345 |     |     |     |     | 350 |     |     |
| Ala | Ser | Leu | Phe | Leu | Ile | Gly | Met | His | Thr | Thr | Gly | Ser | Met | Glu | Val |
|     |     | 355 |     |     |     |     | 360 |     |     |     |     | 365 |     |     |     |
| Ser | Ala | Glu | Ser | Asn | Arg | Leu | Val | Gly | Glu | Leu | Lys | Leu | Asp | Arg | Leu |
|     | 370 |     |     |     |     | 375 |     |     |     |     | 380 |     |     |     |     |
| Leu | Leu | Glu | Leu | Lys | His | Ser | Asn | Ile | Gly | Pro | Phe | Pro | Val | Glu | Leu |
| 385 |     |     |     |     | 390 |     |     |     |     | 395 |     |     |     |     | 400 |

| | | | | | | | | | | | | | | |
|---|---|---|---|---|---|---|---|---|---|---|---|---|---|---|
|Leu|Gln|Asp|Ile|Met<br>405|Asn|Tyr|Ile|Val|Pro<br>410|Ile|Leu|Val|Leu|Pro<br>415|Arg|
|Val|Asn|Glu|Lys<br>420|Leu|Gln|Lys|Gly|Phe<br>425|Pro|Leu|Pro|Thr|Pro<br>430|Ala|Arg|
|Val|Gln|Leu<br>435|Tyr|Asn|Val|Val|Leu<br>440|Gln|Pro|His|Gln|Asn<br>445|Phe|Leu|Leu|
|Phe|Gly|Ala<br>450|Asp|Val|Val|Tyr<br>455|Lys|

( 2 ) INFORMATION FOR SEQ ID NO:20:

( i ) SEQUENCE CHARACTERISTICS:
        ( A ) LENGTH: 11 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:20:

TATCATGCTA G                          11

( 2 ) INFORMATION FOR SEQ ID NO:21:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:21:

CAGGCCTTGA GGTTTTGGCA G                21

( 2 ) INFORMATION FOR SEQ ID NO:22:

( i ) SEQUENCE CHARACTERISTICS:
        ( A ) LENGTH: 39 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:22:

CTGCCAGTAA TGACCAAAAT CGATCCTGTG GCTGGAATC        39

( 2 ) INFORMATION FOR SEQ ID NO:23:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:23:

GATTCTGTGG CTGGAATC                      18

( 2 ) INFORMATION FOR SEQ ID NO:24:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:24:

GTCTGCAACA GATATTTACT TGAGCTCATG CAG 33

( 2 ) INFORMATION FOR SEQ ID NO:25:

( i ) SEQUENCE CHARACTERISTICS:
( A ) LENGTH: 103 amino acids
( B ) TYPE: amino acid
( D ) TOPOLOGY: linear ( i i ) MOLECULE TYPE: protein ( x i ) SEQUENCE DESCRIPTION: SEQ ID NO:25:

| Met | Arg | Glu | Asn | Met | Ala | Arg | Gly | Pro | Cys | Asn | Ala | Pro | Arg | Trp | Val |
| 1 | | | | 5 | | | | | 10 | | | | | 15 | |
| Ser | Leu | Met | Val | Leu | Val | Asn | Lys | Met | Asn | Ser | Gln | Val | Cys | Glu | Lys |
| | | | 20 | | | | 25 | | | | | 30 | | | |
| Val | Thr | Asn | Ser | Val | Ser | Ser | Lys | Leu | Gln | Pro | Tyr | Phe | Gln | Thr | Leu |
| | | 35 | | | | | 40 | | | | | 45 | | | |
| Pro | Val | Met | Thr | Lys | Ile | Asp | Ser | Val | Ala | Gly | Ile | Asn | Tyr | Gly | Leu |
| | 50 | | | | | 55 | | | | | 60 | | | | |
| Val | Ala | Pro | Pro | Ala | Thr | Thr | Ala | Glu | Thr | Leu | Asp | Val | Gln | Met | Lys |
| 65 | | | | | 70 | | | | 75 | | | | | | 80 |
| Gly | Glu | Phe | Tyr | Ser | Glu | Leu | Gln | Pro | His | Gln | Asn | Phe | Leu | Leu | Phe |
| | | | | 85 | | | | | 90 | | | | | 95 | |
| Gly | Ala | Asp | Val | Val | Tyr | Lys |
| | | | 100 | | | |

( 2 ) INFORMATION FOR SEQ ID NO:26:

( i ) SEQUENCE CHARACTERISTICS:
( A ) LENGTH: 432 base pairs
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:26:

CAGGCCTTGA GGTTTTGGCA GCTCTGGAGG ATGAGAGAGA ACATGGCCAG GGGCCCTTGC 60

AACGCGCCGA GATGGGTGTC CCTGATGGTG CTCGTCAACA AGATGAACAG CCAGGTCTGC 120

GAGAAAGTGA CCAATTCTGT ATCCTCCAAG CTGCAACCTT ATTTCCAGAC TCTGCCAGTA 180

ATGACCAAAA TAGATTCTGT GGCTGGAATC AACTATGGTC TGGTGGCACC TCCAGCAACC 240

ACGGCTGAGA CCCTGGATGT ACAGATGAAG GGGGAGTTTT ACAGTGAGCT TCAGCCTCAC 300

CAGAACTTCC TGCTGTTCGG TGCAGACGTT GTCTATAAAT GAAGGCACCA GGGGTGCCGG 360

GGGCTGTCAG CCGCACCTGT TCCTGATGGG CTGTGGGGCA CCGGCTGCCT TTCCCCAGGG 420

AATCCTCTCC AG 432

( 2 ) INFORMATION FOR SEQ ID NO:27:

( i ) SEQUENCE CHARACTERISTICS:
( A ) LENGTH: 21 base pairs
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:27:

CTGCCAGTAA TGACCAAAAT C 21